(12) United States Patent
Rothenberg et al.

(10) Patent No.: US 10,155,985 B2
(45) Date of Patent: Dec. 18, 2018

(54) EVALUATION OF EOSINOPHILIC ESOPHAGITIS

(71) Applicant: CHILDREN'S HOSPITAL MEDICAL CENTER, Cincinnati, OH (US)

(72) Inventors: Marc E. Rothenberg, Cincinnati, OH (US); Carine Blanchard, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 15 days.

(21) Appl. No.: 15/340,282

(22) Filed: Nov. 1, 2016

(65) Prior Publication Data

US 2017/0067111 A1 Mar. 9, 2017

Related U.S. Application Data

(63) Continuation of application No. 12/492,456, filed on Jun. 26, 2009, now abandoned, which is a continuation-in-part of application No. 11/721,127, filed as application No. PCT/US2005/044456 on Dec. 7, 2005, now Pat. No. 8,030,003.

(60) Provisional application No. 60/633,909, filed on Dec. 7, 2004.

(51) Int. Cl.
  *C12Q 1/68* (2018.01)
  *C12Q 1/6883* (2018.01)
  *G01N 33/68* (2006.01)
  *A61K 31/56* (2006.01)

(52) U.S. Cl.
  CPC ........... *C12Q 1/6883* (2013.01); *A61K 31/56* (2013.01); *G01N 33/6893* (2013.01); *C12Q 2600/158* (2013.01); *C12Q 2600/16* (2013.01); *G01N 2800/06* (2013.01); *G01N 2800/24* (2013.01)

(58) Field of Classification Search
  CPC ........... G01N 2800/06; G01N 2800/24; G01N 33/6893
  USPC ...................................................... 435/6.11
  See application file for complete search history.

(56) References Cited

U.S. PATENT DOCUMENTS

| | | | |
|---|---|---|---|
| 5,530,101 | A | 6/1996 | Queen et al. |
| 5,888,510 | A | 3/1999 | Kishimoto et al. |
| 6,403,782 | B1 | 6/2002 | Luster et al. |
| 6,780,973 | B1 | 8/2004 | Luster et al. |
| 8,030,003 | B2 | 10/2011 | Rothenberg |
| 2003/0157479 | A1 | 8/2003 | Bachmann |
| 2003/0194404 | A1 | 10/2003 | Greenfeder |
| 2004/0141951 | A1 | 7/2004 | Rothenberg |
| 2009/0233275 | A1 | 9/2009 | Rothenberg |
| 2009/0269774 | A1 | 10/2009 | Rothenberg et al. |
| 2011/0195500 | A1 | 8/2011 | Rothenberg |

FOREIGN PATENT DOCUMENTS

| | | |
|---|---|---|
| EP | 0949271 A1 | 10/1999 |
| WO | WO-2005/106492 A2 | 11/2005 |
| WO | WO-2005/106492 A3 | 11/2005 |

OTHER PUBLICATIONS

Blanchard et al. (2006), (Journal of Clinical investigation (2006) vol. 116, pp. 536-547).*
Markowitz et al. (2003), ( American Journal of Gastroenterology (2003) vol. 98, pp. 777-782).*
Berkman, et al., Am. J. Respir. Cell Mol. Biol., 2004, vol. 24, pp. 682-687.
Blanchard, C., et al., inhibition of Human Interleukin-13-Induced Respiratory and Oesophageal Inflammation by Anti-Human-Interleukin-13 Antibody (CAT-354), Clin Exp Allergy, 2005, vol. 35, pp. 1096-1103.
Blanchard et al (Journal of Clinical investigation (2006) vol. 116, pp. 536-547) and supplemental data.
Blanchard et al., Eosinophilic esophagitis: Pathogenesis, genetics, and therapy, J. Allergy Clin. Immunol. vol. 188 No. 5. 1059 (2006).
Blanchard et al. Eotaxin-3 and a uniquely conserved gene-expression profile in eosinophilic esophagitis, Journal of Clinical Investigation vol. 116 No. 2 536-547 (2006).
Blanchard et al. IL-13 involvement in eosinophilic esophagitis: Transcriptome analysis and reversibility with glucocorticoids J. Allergy Clin Immunol. vol. 120 No. 6 1292-1300 (2007).
Blanchard et al. *IL—13 Is Overexpressed in Eosinophilic Esophagitis and Induces Eotaxin-3 Expression. In Esophageal Epithelial Cells*. J. Allergy Clin Immunol (2007).
Blanchard et al., Basics Pathogenesis of Eosinophilic Esophagitis, Gastrointest Endosc Clin N. Am. 18(1) 133-143(2008).
Eisner, Jam, et al., "The CC Chemokine Antagonist Met-RANTES Inhibits Eosinophil Effector Functions Through the Chemokine Receptors CCR1 and CCR3," European Journal of Immunology, 1997, vol. 27, pp. 2892-2898.
Faubion, William A., Jr., et al., "Treatment of Eosinophilic Esophagitis with Inhaled Corticosteroids," Journal of Pediatric Gastroenterology and Nutrition, 1998, vol. 27, pp. 90-93.
Garrett, Jennifer K., et al., "Anti-Interleukin-5 (Mepolizumab) Therapy for Hypereosinophilic Syndromes," J Allerby Clin Immunol, 2004, vol. 113, No. 1, pp. 115-119.
Hogan, S. P., et al., "Review Article: The Eosinophil as a Therapeutic Target in Gastrointestinal Disease," Aliment Pharmacol Ther, 2004, vol. 20, pp. 1231-1240.
Kledal, Thomas N., et al., A Broad-Spectrum Chemokine Antagonist Encoded by Kaposl's Sarcoma-Associated Herpesvirus, Science, 1997, vol. 277, pp. 1656-1659.
Komiya, Akiko, et al., "Concerted Expression of Eotaxin-1, Eotaxin-2, and Eotaxin-3 in Human Bronchial Epithelial Cells," Cellular Immunology, 2003, vol. 225, pp. 91-100.
Markowitz et al ( American Journal of Gastroenterology (2003) vol. 98, pp. 777-782).

(Continued)

*Primary Examiner* — Janet L Epps-Smith
(74) *Attorney, Agent, or Firm* — Mintz Levin Cohn Ferris Glovsky and Popeo, P.C.; Muriel Liberto, Esq.

(57) ABSTRACT

A method to evaluate eosinophilic esophagitis based on information in an eosinophilic esophagitis transcriptome.

5 Claims, 4 Drawing Sheets
Specification includes a Sequence Listing.

(56) References Cited

OTHER PUBLICATIONS

Milgrom, et al., N. Engl. J. Med., 1999,vol. 341, pp. 1966-1973.
Mishra, Anil, et al., "An Etiological Role for Aeroallergens and Eosinophils in Experimental Esophagitis," The Journal of Clinical Investigation, 2001, vol. 107, pp. 83-90.
Naya, Akira, et al., "Discovery of a Novel CCR3 Selective Antagonist," Bioorganic & Medicinal Chemistry Letters, 2001, vol. 11, pp. 1219-1223.
Naya, Akira, et al., "Structure-Activity Relationships of 2-(Benzothiazolylthio)acetamide Class of CCR3 Selective Antagonist" Chem. Pharm. Bull., 2003, vol. 51, No. 6, pp. 697-701.
Notes from 5th International Eosinophil Symposium (Jul. 2007).
Proudfoot, Amanda E. I., et al., "Amino-terminally Modified RANTES Analogues Demonstrate Differential Effects on RANTES Receptors," The Journal of Biological Chemistry, 1999, vol. 274, No. 45, pp. 32478-32485.
Sabroe, Ian, et al., "A Small Molecule Antagonist of Chemokine Receptors CCR1 and CCR3," The Journal of Biological Chemistry, 2000, vol. 275, No. 34, pp. 25985-25992.
Saeki, Toshihiko, et al., "Identification of a Potent and Nonpeptidyl CCR3 Antagonist," Biochemical and Biophysical Research Communications, 2001, vol. 281, pp. 779-782.
Shinkai, A. et al. (Nov. 2002). "N-terminal domain of eotaxin-3 is important for activation of CC chemokine receptor 3," Protein Eng 15(11):923-929.
Teitelbaum, Jonathan E., et al., "Eosinophilic Esophagitis in Children: Immunopathological Analysis and Response to Fluticasone Propionate," Gastroenterology, 2002, vol. 122, pp. 1216-1225.
Varnes, Jeffrey G., et al., "Discovery of N-propyiurea 3-benzylpiperidines as Selective CC Chemokine Receptor-3 (CCR3) Antagonists," Bioorganic & Medicinal Chemistry Letters, 2004, vol. 14, pp. 1645-1649.
Wacker, Dean A., et al., "CCR3 Antagonists: A Potential New Therapy for the Treatment of Asthma. Discovery and Structure-Activity Relationships," Bioorganic & Medicinal Chemistry Letters, 2002, vol. 12, pp. 1785-1789.
Whites, John R., et al., "Identification of Potent, Selective Nonpeptide CC Chemokine Receptor-3 Antagonist That Inhibits Eotaxin-, Eotaxin-2-, and Monocyte Chemotactic Protein-4-Induced Eosinophil Migration," The Journal of Biological Chemistry, 2000, vol. 275, No. 47, pp. 36626-36631.
Zimmerman, Nives, et al., "Chemokines in Asthma: Cooperative Interaction Between Cemokines and IL-13," J. Allergy Clin Immunol, 2003, vol. 111, No. 2, pp. 227-242.
International Search Report received in connection with PCT/US2005/044456, dated Dec. 7, 2006, pp. 1-7.
United States Patent and Trademark Office (USPTO), Office Action, issued in corresponding U.S. Appl. No. 13/051,873, dated Jan. 10, 2012, dated Jan. 10, 2012, 25 pages.
Final Office Action dated Jan. 22, 2014, for U.S. Appl. No. 12/492,456, 35 pages.
Mayer, M.R. et al. (Apr. 27, 2001, e-published Jan. 31, 2001). "Identification of receptor binding and activation determinants in the N-terminal and N-loop regions of the CC chemokine eotaxin," J Biol Chem 276(17):13911-13916.
Zimmerman, N. et al. (Apr. 30, 1999). "CC chemokine receptor-3 undergoes prolonged ligand-induced internalization," J Biol Chem 274(18):12611-12618.

* cited by examiner

| EE RESPONDERS | EE | NL | FOLD CHANGES | GENE SYMBOL | SEQ ID NUMBER | GENEBANK ID NUMBER |
|---|---|---|---|---|---|---|
| | | | 4.11 | UPK1B | 61 | NM_006952 |
| | | | 2.906 | CDH26 | 6 | NM_021810 |
| | | | 2.41 | SH2D1B | 129 | NM_053282 |
| | | | 2.173 | IF | 35 | NM_000204 |
| | | | 2.106 | | 43 | CA314541 |
| | | | 0.5 | EML1 | 1441 | NM_001008707 |
| | | | 0.5 | AADACL2 | 1515 | NM_207365 |
| | | | 0.496 | CHI3L1 | 1620 | AK125406 |
| | | | 0.473 | SNX19 | 1358 | NM_001276 |
| | | | 0.469 | ARG1 | 1615 | NM_014758 |
| | | | 0.395 | PNLIPRP3 | 1538 | NM_000045 |
| | | | 0.393 | DSG1 | 1584 | NM_001101709 |
| | | | 0.249 | | 1618 | NM_001942 |

FIG. 6

EVALUATION OF EOSINOPHILIC ESOPHAGITIS

RELATED APPLICATION

This is a Continuation of U.S. application Ser. No. 12/492,456 filed Jun. 26, 2009, which is a Continuation in Part of U.S. application Ser. No. 11/721,127 filed Jun. 7, 2007, now U.S. Pat. No. 8,030,003 granted Oct. 4, 2011, which claims priority from PCT/US2005/044456 filed Dec. 7, 2005, which claims priority from U.S. application Ser. No. 60/633,909 filed Dec. 7, 2004, each of which is expressly incorporated by reference herein in its entirety.

This invention was made with government support under AI045898 awarded by the National Institutes of Health. The government has certain rights in this invention.

FIELD OF THE INVENTION

The invention is directed generally to evaluating and mitigating eosinophilic esophagitis.

BACKGROUND

Patients with eosinophilic esophagitis may have symptoms that include abdominal pain, difficulty swallowing, vomiting, failure to thrive and weight loss. In addition, allergy, particularly food allergy, is an associated finding in most patients, and many have concomitant asthma or other chronic respiratory disease. Diagnosis requires endoscopy, and diseased tissue shows characteristic punctuate white surface dots associated with erythema, loss of vascular pattern, ulcers, or ringed trachea-like appearance.

Patients with eosinophilic esophagitis typically have elevated levels of eosinophils in esophageal tissue and peripheral blood. Eosinophils are one type of granulocytic leukocyte (white blood cell) or granulocyte that normally appears in the peripheral blood at a concentration of about 1-3% of total leukocytes. Their presence in tissues is normally primarily restricted to the gastrointestinal mucosa, i.e. the stomach and intestines. Eosinophil accumulation in the peripheral blood and tissues is a hallmark feature of an allergic response, and may cause potent pro-inflammatory effects or tissue remodeling. Because eosinophilic esophagitis is marked by infiltration of eosinophils, this condition may be linked to allergen exposure. Eosinophil accumulation occurs in other allergic diseases such as allergic rhinitis, asthma, and eczema as well as parasitic infections, certain types of malignancies, chronic inflammatory disorders such as inflammatory bowel disease, specific syndromes such as eosinophilic gastroenteritis, eosinophilic colitis, eosinophilic cellulitis, eosinophilic fascitis, and systemic diseases such as Churg Strauss syndrome, eosinophilic pneumonia, and the idiopathic hypereosinophilic syndrome.

Numerous mediators have been identified as eosinophil chemoattractants. These include diverse molecules such as lipid mediators (platelet activating factor (PAF), leukotrienes) and chemokines such as the eotaxin subfamily of chemokines. Chemokines are small secreted proteins produced by tissue cells and leukocytes that regulate leukocyte homing during homeostatic and inflammatory states. Two main subfamilies (CXC and CC chemokines) are distinguished depending upon the arrangement of the first two cysteine amino acids, either separated by one amino acid (CXC), or adjacent (CC).

Due to the increasing incidence of eosinophilic esophagitis, methods to mitigate eosinophilic esophagitis would be beneficial. In addition, because eosinophilic esophagitis is often confused with other disorders such as gastroesophageal reflux disease (GERD), but does not typically respond to anti-GERD therapy, it is important to develop diagnostic features that distinguish between eosinophilic esophagitis and GERD. Diagnosis currently requires endoscopy with subsequent biopsy and analysis of the excised tissue by a pathologist based on manual microscopic analysis, so that less invasive methods of diagnosing eosinophilic esophagitis would also be beneficial.

SUMMARY OF THE INVENTION

The terms normal individuals, individuals without eosinophilic esophagitis (EE), control group or controls, patients without EE, and normal patients are used synonymously. The terms individuals with EE, treated groups, EE patients, and patients with EE are used synonymously.

One embodiment of the invention is a method of assessing eosinophilic esophagitis (EE) in a patient by comparing the patients blood concentration of eotaxin-3 to a normal concentration of eotaxin-3, where an increased concentration of eotaxin-3 indicates EE.

Another embodiment of the invention is a diagnostic assay for EE. One embodiment of the assay may include a test strip containing an anti-eotaxin-3 antibody and at least one reagent that indicates binding of the anti-eotaxin-3 antibody to eotaxin-3 present in a supranormal level in a biological sample. Detection may be by visual inspection for a chromogen, fluorogen, colloidal gold agglutination, luminescence, etc.

Another embodiment of the invention is a diagnostic method for EE where eotaxin-3 DNA, eotaxin-3 mRNA, and/or eotaxin-3 protein is present over a normal amount in a patient tissue, as an indicator of EE in the patient.

Another embodiment of the invention is a diagnostic method for EE where a frequency of single nucleotide polymorphisms (SNPs) in the eotaxin-3 gene above normal frequency is an indicator of EE or a marker of disease risk, prognosis, and/or a response to therapy.

Another embodiment of the invention is a method to mitigate EE by providing an inhibitor to eotaxin-3 and/or a receptor, such as CCR3, for binding eotaxin-3 in a cell, such as a mast cell or an eosinophil, under conditions sufficient to inhibit eotaxin-3 binding to the receptor.

Another embodiment of the invention is a gene expression profile for EE comprising SEQ. ID NOS. 1-1620.

Another embodiment of the invention is a method to evaluate EE by gene expression profiles, where evaluation encompasses assessment of disease propensity, of disease severity, of therapy efficacy, of therapy compliance, etc. In one embodiment, EE is evaluated by determining an expression profile of at least one gene in the esophagus of the patient, where the gene is selected from SEQ ID NOS. 1-1620. In one embodiment, EE is evaluated by determining an expression profile of at least one gene in the patient, where the gene is selected from group consisting of SEQ ID NOS. 1-1620. The expression profile of the selected gene(s) is then compared to the expression profile of that same gene in an individual that does not have EE. The patient's propensity for EE is evaluated by determining if the gene in the patient is either over-expressed ≥1.5 times or is under-expressed ≥1.5 times compared to the same gene in the expression profile in the individual without EE. This propensity is evaluated by determining the extent that over-expression or under-expression exceeds 1.5, the identify of the gene over-expressed or under-expressed, and/or the number of genes that are over-expressed or under-expressed. The patient's propensity for EE is higher based on at least one of the farther the over-expression or under-expression is from 1.5, the gene is from SEQ ID NO. 1-42, and/or the greater the number of genes that are over-expressed or under-expressed. In one embodiment the gene is SEQ ID NO. 1. In one embodiment, the patient lacks at least one clinical and/or physical symptoms of EE. In one embodiment, the cell is an esophageal cell.

Another embodiment of the invention is a method to evaluate a compound's contribution to the pathophysiology of EE. At least one cell, referred to as the test cell, is exposed to the compound, and an expression profile of at least one gene selected from the group consisting of SEQ ID NOS. 1-1620 in the cell(s) is compared to an expression profile of at least one gene selected from the group consisting of SEQ ID NOS. 1-1620 in a cell of an individual without EE, referred to as the control cell. The contribution of the compound to the pathophysiology of EE is evaluated by determining if the at least one gene in the test cell is either over-expressed ≥1.5 times or is under-expressed ≥1.5 times compared to the same gene in the expression profile of the control cell. The compound's contribution to the pathophysiology of EE is evaluated by determining the extent that over-expression or under-expression exceeds 1.5, the identify of the gene over-expressed or under-expressed, and/or the number of genes that are over-expressed or under-expressed. The compound contributes more to the pathophysiology of EE based on at least one of the farther the over-expression or under-expression is from 1.5, the gene is from SEQ ID NO. 1-42, and/or the greater the number of genes that are over-expressed or under-expressed. In one embodiment, the cell is an esophageal cell. In one embodiment, based on the extent that the compound contributes to EE, therapeutics that antagonize the action of the compound may be used to treat EE.

Another embodiment of the invention is a method to evaluate an individual's response to therapy for EE. An expression profile of at least one gene selected from the group consisting of SEQ ID NOS. 1-1620 in an esophagus of an individual exposed to therapy is compared to an expression profile of the same gene(s) from an individual without EE. The individual's response to therapy for EE is evaluated by determining if the at least one gene is either over-expressed ≥1.5 times or is under-expressed ≥1.5 times compared to the same gene in the expression profile from the individual without EE. The individual's response to therapy for EE is evaluated based on the extent that over-expression or under-expression exceeds 1.5, the identify of the gene over-expressed or under-expressed, and/or the number of genes that are over-expressed or under-expressed. The individual is less responsive to therapy for EE based on at least one of the farther the over-expression or under-expression is from 1.5, the gene is from SEQ ID NO. 1-42, and/or the greater the number of genes that are expressed or under-expressed.

Another embodiment of the invention is a method to evaluate an individual's compliance with therapy for EE. An expression profile of at least one gene selected from the group consisting of SEQ ID NOS. 1-1620 in an esophagus of an individual prescribed therapy for EE is compared to an expression profile of the same gene(s) from an individual without EE. The individual's compliance with therapy is evaluated by determining if the at least one gene is either over-expressed ≥1.5 times or is under-expressed ≥1.5 times compared to the same gene in the expression profile from the individual without EE. The individual's compliance with therapy is determined based on the extent that over-expression or under-expression exceeds 1.5, the identify of the gene over-expressed or under-expressed, and/or the number of genes that are over-expressed or under-expressed. The individual is less compliant with therapy for EE based on at least one of the father the over-expression or under-expression is from 1.5, the gene is from SEQ ID NO. 1-42, and/or the greater the number of genes that are over-expressed or under-expressed. That is, the gene expression is more like an individual with EE than a normal EE without EE.

Another embodiment of the invention is a method to evaluate whether an individual had EE prior to a current assessment. An expression profile of at least one gene selected from the group consisting of SEQ ID NOS. 6, 35, 43, 61, 129, 1358, 1441, 1515, 1538, 1584, 1615, 1618, and 1620 in an esophagus of an individual is compared to the expression profile of the same gene(s) from an individual without EE. The individual's prior EE is evaluated by determining if the at least one gene is either over-expressed ≥1.5 times or is under-expressed ≥1.5 times compared to the same gene in the expression profile from the individual without EE. The likelihood of the individual having EE prior to the current assessment is determined based on the extent that over-expression or under-expression exceeds ≥1.5, the identity of the gene over-expressed or under-expressed, and/or the number of genes that are over-expressed or under-expressed. The individual is more likely to have had prior EE based on at least one of the farther the over-expression or under-expression is from 1.5, and/or the greater the number of genes that are over-expressed or under-expressed. In one embodiment, the individual does not have active EE when the method is performed.

These and other advantages will be apparent in light of the following figures and detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 shows fluticasone propionate treatment-resistant genes within the EE transcriptome.

DETAILED DESCRIPTION

Figure 1:
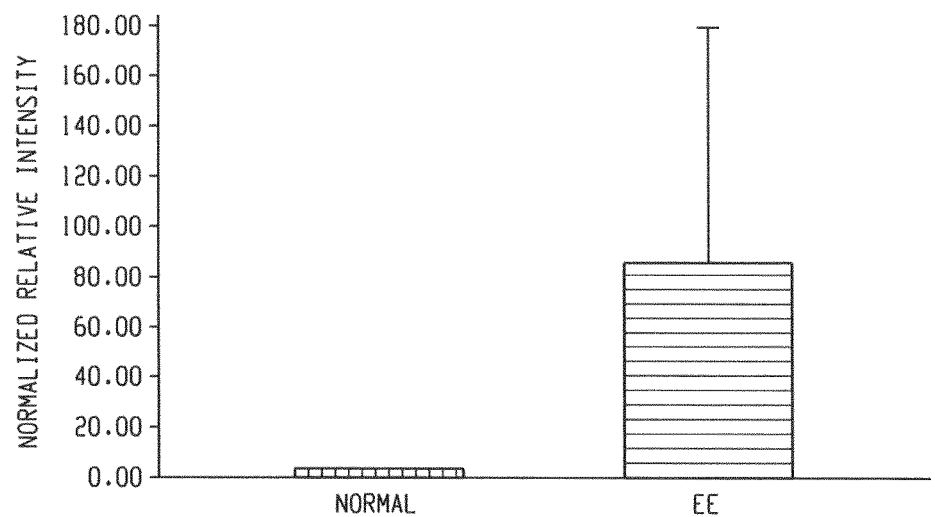
FIG. 1 shows DNA microarray data of eotaxin-3 mRNA levels in esophageal tissue of normal patients and patients with eosinophilic esophagitis (EE).

Methods of diagnosing, assessing, and mitigating eosinophilic esophagitis (EE) by modulating levels and activity of eotaxin-3 and by evaluating gene expression profiles are disclosed.

Eotaxin-3 is a CC chemokine with selective activity on eosinophils. For example, eotaxin-3 recruits and directs eosinophils to sites in the body, such as the esophagus, via chemoattraction. Additional chemokines have been identified in the genome that encode for CC chemokines with eosinophil-selective chemoattractant activity, and have been designated eotaxin-1 and eotaxin-2.

The activity of eotaxin-3 is mediated by the selective expression of an eotaxin receptor, CCR3, on eosinophils. CCR3 is a promiscuous receptor; it interacts with multiple ligands including macrophage chemoattractant proteins (MCP)-2, -3, and -4, RANTES (regulated upon activation normal T-cell expressed and secreted), and HCC-2 (MIP-5, leukotactin). The only ligands that signal exclusively through this receptor, however, are eotaxins-1, -2, and -3, accounting for the cellular selectivity of the eotaxins.

Esophageal tissue obtained from patients previously diagnosed with EE was analyzed. Diagnosis was based on analysis of excised tissue from endoscopic biopsy. Tissues from patients with EE, as well as patients not having EE (controls) were subjected to genome-wide microarray transcript profiling (Affymetrix GeneChip). All work was performed at the Core facility at Children's Hospital Medical Center (Cincinnati Ohio).

Briefly, RNA quality was first assessed using the Agilent bioanaiyzer (Agilent Technologies, Palo Alto Calif.). Only mRNA having a ratio of 28S/18S between 1.3 and 2 were subsequently used. RNA was converted to cDNA with Superscript choice for cDNA synthesis (Invitrogen, Carlsbad Calif.) and subsequently converted to biotinylated cRNA with Enzo High Yield RNA Transcript labeling kit (Enzo Diagnostics, Farmingdale N.Y.). After hybridization to the GeneChip (Affymetrix, Santa Clara Calif.), the chips were automatically washed and stained with streptavidin-phycoerythrin using a fluidics system. The chips were scanned with a Hewlett Packard GeneArray Scanner. Over 30,000 unique genes were screened.

Levels of gene transcripts were determined from data image files, using algorithms in the Microarray Analysis Suite software (Affymetrix). Levels from chip to chip were compared by global scaling. Each gene was typically represented by a probe set of 16 to 20 probe pairs. Each probe pair consisted of a perfect match oligonucleotide and a mismatch oligonucleotide that contained a one base mismatch at a central position. Two measures of gene expression were used, absolute call and average difference. Absolute call is a qualitative measure in which each gene is assigned a call of present, marginal or absent, based on the hybridization of the RNA to the probe set. Average difference is a quantitative measure of the level of gene expression, calculated by taking the difference between mismatch and perfect match of every probe pair and averaging the differences over the entire probe set. Data were normalized and an EE transcriptome gene list was created with results having p<0.01 (Welch t-test with or without false rate discovery) and ≥1.5-fold change.

FIG. 1 shows the normalized relative average difference of the gene encoding eotaxin-3 from normal patients and patients with EE. The microarray analysis identified eotaxin-3 as the top gene induced, indicating a role in EE. Eotaxin-1 and eotaxin-2 mRNA levels were not significantly increased in EE patients.

Figure 2:
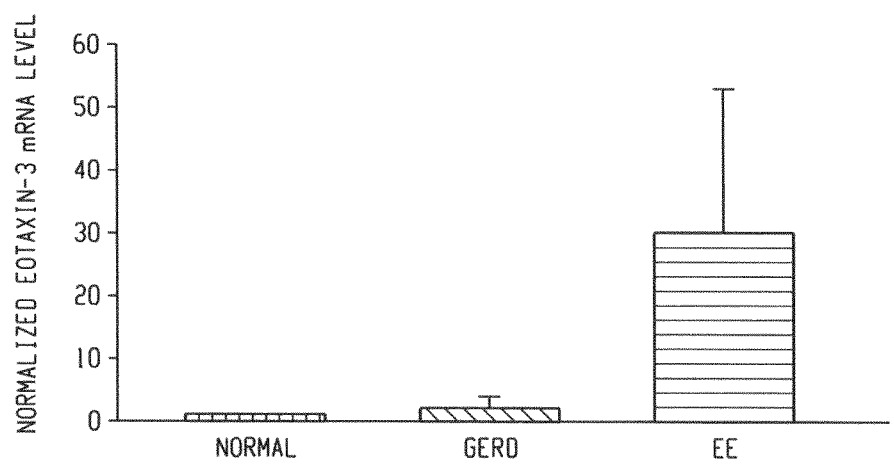
FIG. 2 shows data from quantitative polymerase chain reaction analysis showing normalized eotaxin-3 mRNA levels in normal patients, patients with gastroesophageal reflux disease (GERD), and patients with EE.

Quantitative polymerase chain reaction (PCR) using LightCycler technology (Roche Diagnostics Corp. Indianapolis Ind.) which involves a competitive amplification of cDNA prepared from esophageal RNA, known to one skilled in the art, was further utilized to validate the microarray analysis results. Levels of eotaxin-3 mRNA from normal patients, patients with gastroesophageal reflux disease (GERD), and patients with EE were compared. As shown in FIG. 2, eotaxin-3 mRNA was induced nearly 100-fold in patients with EE when normalized to a housekeeping gene GAPDH. Patients with GERD showed only slightly increased levels compared to normal patients. Levels of the other two eotaxin mRNA species (eotaxin-1 and eotaxin-2) were not increased in patient esophageal samples (data not shown), validating the specific role of eotaxin-3.

A murine model of EE was evaluated to determine the role of the eotaxin-3 receptor, CCR3. The model is disclosed in Mishra et al., *J. Clin. Invest.* (2001) 107, 83, which is expressly incorporated by reference herein in its entirety. Because EE is marked by infiltration of eosinophils, this condition may be linked to exposure to allergens. In support of this, animals models of EE were induced by allergen exposure to the respiratory tract. In brief, mice were exposed to repeated doses of intranasal *Aspergillus fumigatus* antigen (three doses a week) for three weeks. Subsequently, the mice were euthanized 18 hours after the last dose of allergen or saline control, and the esophagus was analyzed for the occurrence of EE.

Figure 3:
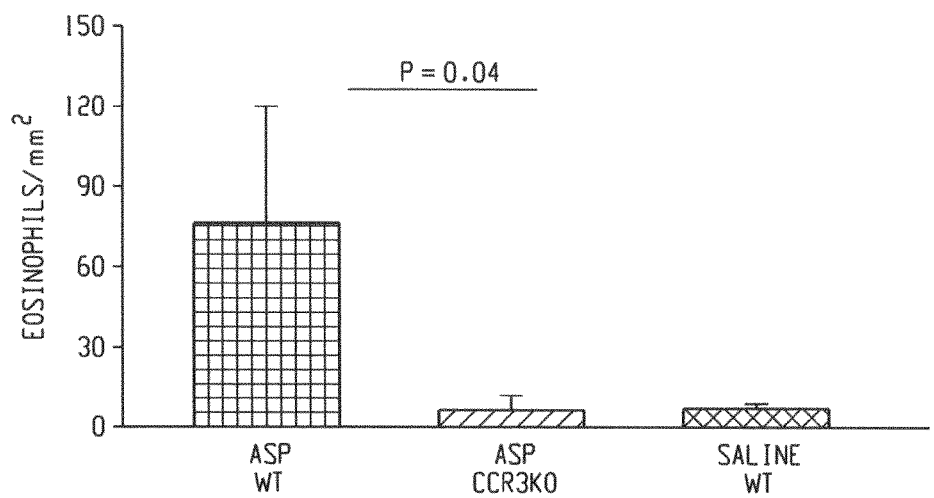
FIG. 3 shows esophageal eosinophil concentration in control and allergen-induced wild-type mice, and allergen-induced mice lacking the gene encoding the CCR3 receptor.

Specifically, asthma was experimentally induced in wild-type and CCR3 knockout (KO) mice (a gift of Drs. Craig Gerard and Allison Humbles at Harvard Medical School) using *Aspergillus fumigatus* (ASP) as an allergen. Wild-type control mice received saline. The concentration of eosinophils was determined in the esophagus of allergen-induced wild-type mice (ASP wt), control wild-type mice (saline wt), and allergen-induced mice lacking the gene encoding CCR3 (ASP CCR3KO). The results are shown in FIG. 3.

The concentration of eosinophils in allergen-induced wild-type mice (ASP wt) was about 75 eosinophils per $mm^2$. The concentration of eosinophils in allergen-induced CCR3KO mice (ASP CCR3KO) was about 4 eosinophils per $mm^2$, similar to the eosinophil concentration in control wild-type mice (saline wt). The decreased concentration of eosinophils in allergen-induced CCR3KO mice compared to allergen-induced wild-type mice was statistically significant (p=0.04; Students T-test).

EE-related symptoms and/or pathology may be mitigated by mediating eosinophil chemotactic events using techniques such as those disclosed in U.S. Pat. No. 6,780,973, which is expressly incorporated by reference herein in its entirety. One example is a recombinant polypeptide capable of mediating eosinophil chemotactic events where the polypeptide includes a domain having a sequence which has at least 70% identity to full length murine eotaxin cDNA, full length guinea pig eotaxin cDNA, and/or human eotaxin DNA. Another example is reducing eotaxin activity using an antagonist such as an antieotaxin-3 antibody or eotaxin-1, -2, or -3 fragment, a purified antibody which binds specifically to a murine or human eotaxin-3 protein indicating an intact monoclonal or polyclonal antibody, an immunologically active antibody fragment, or a genetically engineered fragment. The antagonist may be an eotaxin-1, -2, or -3 polypeptide having a deletion of 1-10 N-terminal amino acids, or having an addition of 3-10 amino acids on the amino terminus.

Figure 4:
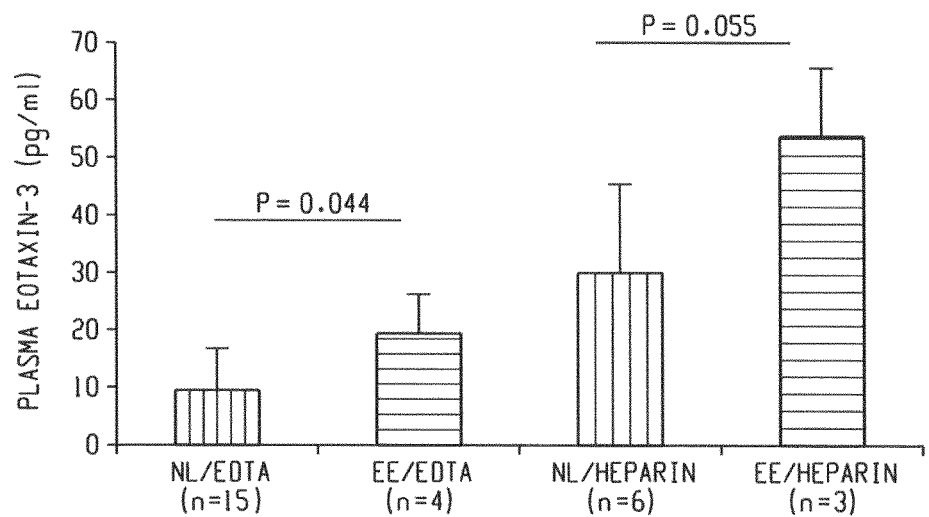
FIG. 4 shows plasma concentrations of eotaxin-3 in normal patients and patients with EE.

The concentration of eotaxin-3 protein in plasma was elevated in patients with EE, compared to normal controls. Concentrations were determined using a commercially purchased sandwich ELISA kit (R&D Quantikine CCL-26 kit, R&D Systems Inc., Minneapolis Minn.). In blood anticoagulated with heparin, eotaxin-3 concentrations in plasma of normal patients were 29.43 pg/ml±15.4 pg/ml (n=6), and eotaxin-3 concentration in patients with eosinophilic esophagitis were 52.97 pg/ml±12 pg/ml (n=3) (p=0.055). In blood anticoagulated with ethylenediamine tetraacetic acid (EDTA), eotaxin-3 concentrations in plasma of normal patients were 8.3 pg/ml±7 pg/ml (n=15), and eotaxin-3 concentration in patients with eosinophilic esophagitis were 18.19 pg/ml±7 (n=4) (p=0.044). These data are shown in FIG. 4.

Therefore, the blood concentration of eotaxin-3 in an individual may be compared to a normal level as a relatively non-invasive or minimally invasive indication of eosinophilic esophagitis. In one embodiment, a plasma concentration of eotaxin-3 of about 52.97 pg/ml±12 pg/ml in blood anticoagulated with heparin is indicative of EE. In another embodiment, a plasma concentration of eotaxin-3 of about 18.19 pg/ml±7 pg/ml in blood anticoagulated with EDTA is indicative of EE. These blood concentrations of eotaxin-3 may serve as a diagnostic marker, for which a less invasive diagnostic test for EE may be used, as further discussed below, to replace or serve as a preliminary indicator or whether a more invasive test, e.g. endoscopic biopsy, is warranted. The level of eotaxin-3 may also serve to determine if a specific therapy is mitigating EE, and thus may be used to monitor therapy. Similarly, the concentration or amount of eotaxin-3 DNA, eotaxin-3 mRNA, or eotaxin-3 protein over a normal amount in a patient tissue, such as blood or esophageal tissue, can be utilized further as an indicator of EE in the patient.

For evaluation of EE using clinical and/or physical assessment, biopsy tissues (obtained from the distal esophagus during routine endoscopy) were submerged in formalin for routine pathological analysis with hematoxylin and eosin staining. Diagnosis was established based on the maximum eosinophil count per high power field (hpf) and basal layer expansion according to method known in the art (e.g., established criteria in Rothenberg et al., Pathogenesis and clinical features of eosinophilic esophagitis. J Allergy Clin Immunol 108 (2001) 891; Attwood et al., Esophageal eosinophilia with dysphagia. A distinct clinicopathologic syndrome. Dig Dis Sci 38 (1993)109; Fox et al., Eosinophilic esophagitis: its not just kid's stuff. Gastrointest Endosc 56 (2002) 26, each of which is expressly incorporated by reference herein in its entirety. Normal individuals (NL), n=13, served as a control and were defined as having 0 eosinophils/hpf and no basal layer expansion. Individuals with EE (n=76) were defined as having >24 eosinophils/hpf and extensive basal layer hyperplasia (expansion to about >⅓ of epithelium).

Figure 5:
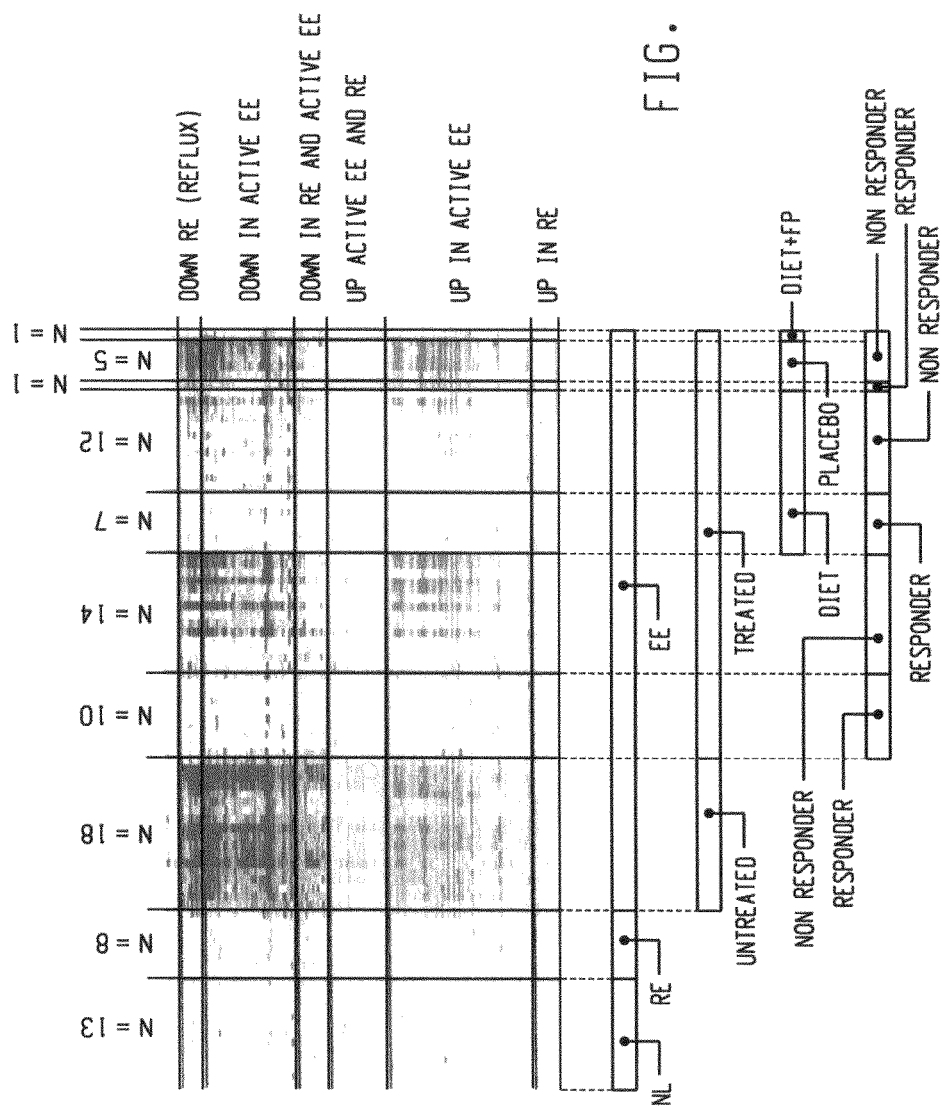
FIG. 5 shows hierarchical cluster analysis of transcripts expressed in normal (NL), reflux (RE), and EE esophageal biopsies.

Whole genome wide expression analysis demonstrated an EE transcriptome comprising 1620 genes. That is, 1620 genes were expressed significantly differently in EE patients compared to normal individuals, meaning that, at p<0.01, these 1620 genes from EE patients, using a patient pool size of 89, of which 76 patients had been diagnosed with EE, and 13 patients were individuals without EE, were either up-regulated or down-regulated by ≥1.5 fold, compared to normal individuals (NL). The data were analyzed by cluster analysis and ordered (standard correlation (A) and distance (B)) using Genespring software. Results are shown in FIG. 5 and Table 1. In FIG. 5, down-regulated genes were depicted in blue; and up-regulated genes were depicted in red, with the magnitude of the gene change proportional to the intensity of the blue and/or red colors. Each column represented a separate individual and each line a gene. RNA from each patient was subjected to chip analysis using Affymetrix Human Genome U133 GeneChip plus 2.

TABLE 1

The EE transcriptome

| Common Name | Description | Fold Change | Genbank Accession number | SEQ ID NO |
|---|---|---|---|---|
| CCL26 | Chemokine (C-C motif) ligand 26 | 62.73 | NM_006072 | 1 |
| TNFAIP6 | Tumor necrosis factor, alpha-induced protein 6 | 42.94 | NM_007115 | 2 |
| ALOX15 | Arachidonate 15-lipoxygenase | 36.11 | NM_001140 | 3 |
| APOBEC3A | Apolipoprotein B mRNA editing enzyme, catalytic polypeptide-like 3A | 24.37 | NM_145699 | 4 |
| POSTN | Periostin, osteoblast specific factor | 23.42 | NM_006475 | 5 |
| CDH26 | Cadherin-like 26 | 23.28 | NM_021810 | 6 |
| CXCL1 | Chemokine (C-X-C motif) ligand 1 (melanoma growth stimulating activity, alpha) | 20.89 | NM_001511 | 7 |
| NEFL | Neurofilament, light polypeptide 68 kDa | 17.68 | NM_006158 | 8 |
| TMEM16A | Transmembrane protein 16A | 17.5 | NM_018043 | 9 |
| SEQ_ID_#10 | | 16.93 | XM_293626 | 10 |
| PMCH | Pro-melanin-concentrating hormone | 16.04 | NM_002674 | 11 |
| TMEM71 | Hypothetical protein FLJ33069 | 15.06 | NM_144649 | 12 |
| CPA3 | Carboxypeptidase A3 (mast cell) | 14.51 | NM_001870 | 13 |
| LRRC31 | Leucine rich repeat containing 31 | 12.48 | NM_024727 | 14 |
| IGLC2 | Immunoglobulin lambda joining 3 | 12.33 | AK057174 | 15 |
| IGHD | Immunoglobulin heavy constant delta | 12.11 | AK090461 | 16 |
| SEQ_ID_#17 | | 11.46 | XM_097433 | 17 |
| CLC | Charcot-Leyden crystal protein | 11.06 | NM_001828 | 18 |
| SEQ_ID_#19 | | 10.29 | NG_000002 | 19 |
| CXCL6 | Chemokine (C-X-C motif) ligand 6 (granulocyte chemotactic protein 2) | 10.24 | NM_002993 | 20 |
| SEC6L1 | SEC6-like 1 (*S. cerevisiae*) | 8.878 | NM_007277 | 21 |
| TCF12; HEB; HTF4; HsT17266 | *Homo sapiens* mRNA; cDNA DKFZp686K1288 (from clone DKFZp686K1288). | 8.833 | BX647333 | 22 |
| IGJ | Immunoglobulin J polypeptide, linker protein for immunoglobulin alpha and mu polypeptides | 8.768 | NM_144646 | 23 |

TABLE 1-continued

The EE transcriptome

| Common Name | Description | Fold Change | Genbank Accession number | SEQ ID NO |
|---|---|---|---|---|
| C1orf178 | Chromosome 1 open reading frame 178 | 8.681 | NM_001010922 | 24 |
| PHLDB2 | Pleckstrin homology-like domain, family B, member 2 | 8.485 | NM_145753 | 25 |
| GLDC | Glycine dehydrogenase (decarboxylating; glycine decarboxylase, glycine cleavage system protein P) | 8.382 | NM_000170 | 26 |
| EPPK1 | Epiplakin 1 | 7.894 | NM_031308 | 27 |
| UBD | Ubiquitin D | 7.854 | NM_006398 | 28 |
| SUSD2 | Sushi domain containing 2 | 7.725 | NM_019601 | 29 |
| CTSC | synonyms: HMS, PLS, CPPI, DPP1, DPPI, PALS; isoform b precursor is encoded by transcript variant 2; dipeptidyl-peptidase I; dipeptidyl transferase; cathepsin J; Papillon-Lefevre syndrome; go_component: lysosome [goid 0005764] [evidence TAS] [pmid 7665576]; go_function: dipeptidyl-peptidase I activity [goid 0004214] [evidence IEA]; go_function: cysteine-type endopeptidase activity [goid 0004197] [evidence IEA]; go_process: immune response [goid 0006955] [evidence TAS] [pmid 9092576]; go_process: proteolysis and peptidolysis [goid 0006508] [evidence NR]; Homo sapiens cathepsin C (CTSC), transcript variant 2, mRNA. | 7.56 | NM_148170 | 30 |
| TPSB2 | Tryptase beta 2 | 7.199 | NM_003294 | 31 |
| SLC26A4 | Solute carrier family 26, member 4 | 7.192 | NM_000441 | 32 |
| SAMSN1 | SAM domain, SH3 domain and nuclear localisation signals, 1 | 7.119 | NM_022136 | 33 |
| TRPM6 | Transient receptor potential cation channel, subfamily M, member 6 | 6.979 | NM_017662 | 34 |
| IF | I factor (complement) | 6.673 | NM_000204 | 35 |
| IL8 | Interleukin 8 | 6.664 | NM_000584 | 36 |
| FLJ39117 | Repetin | 6.256 | XM_371312 | 37 |
| HRH1 | Histamine receptor H1 | 6.208 | NM_000861 | 38 |
| MUC4 | Mucin 4, tracheobronchial | 6.139 | NM_004532 | 39 |
| KCNJ2 | Potassium inwardly-rectifying channel, subfamily J, member 2 | 6.061 | NM_000891 | 40 |
| IFRG28 | 28 kD interferon responsive protein | 6.035 | NM_022147 | 41 |
| GPR160 | G protein-coupled receptor 160 | 5.995 | NM_014373 | 42 |
| SEQ_ID_#43 | Transcribed locus | 5.944 | CA314541 | 43 |
| CA2 | Carbonic anhydrase II | 5.681 | NM_000067 | 44 |
| CD200R1 | CD200 receptor 1 | 5.587 | NM_138806 | 45 |
| BF | B-factor, properdin | 5.507 | NM_001710 | 46 |
| SCUBE2 | Signal peptide, CUB domain, EGF-like 2 | 5.502 | NM_020974 | 47 |
| MS4A2 | Membrane-spanning 4-domains, subfamily A, member 2 (Fc fragment of IgE, high affinity I, receptor for; beta polypeptide) | 5.471 | NM_000139 | 48 |
| MMP12 | Matrix metalloproteinase 12 (macrophage elastase) | 5.411 | NM_002426 | 49 |
| PGDS | Prostaglandin D2 synthase, hematopoietic | 5.312 | NM_014485 | 50 |
| SEQ_ID_#51 | UI-H-DF1-aug-p-10-0-UI.s1 NCI_CGAP_DF1 Homo sapiens cDNA clone IMAGE: 5869305 3', mRNA sequence. | 5.278 | BM993907 | 51 |
| SEQ_ID_#52 | Transcribed locus | 5.183 | BQ004901 | 52 |
| CHL1 | Cell adhesion molecule with homology to L1CAM (close homolog of L1) | 5.1 | NM_006614 | 53 |
| C9orf150 | Chromosome 9 open reading frame 150 | 4.944 | NM_203403 | 54 |
| APOL1 | Apolipoprotein L, 1 | 4.935 | NM_003661 | 55 |
| SEQ_ID_#56 | LOC441801 | 4.841 | BC037919 | 56 |
| CH25H | Cholesterol 25-hydroxylase | 4.828 | NM_003956 | 57 |
| SEQ_ID_#58 | | 4.822 | XM_294092 | 58 |
| SIDT1 | Hypothetical protein FLJ21394 | 4.822 | NM_017699 | 59 |
| SLC28A3 | Solute carrier family 28 (sodium-coupled nucleoside transporter), member 3 | 4.775 | NM_022127 | 60 |
| UPK1B | Uroplakin 1B | 4.732 | NM_006952 | 61 |
| IL13RA2 | Interleukin 13 receptor, alpha 2 | 4.636 | NM_000640 | 62 |
| PKP2 | Plakophilin 2 | 4.627 | NM_001005242 | 63 |
| MSLN | Mesothelin | 4.616 | NM_005823 | 64 |
| SEQ_ID_#65 | | 4.547 | XM_059368 | 65 |
| SLC6A14 | Solute carrier family 6 (amino acid transporter), member 14 | 4.539 | NM_007231 | 66 |

TABLE 1-continued

The EE transcriptome

| Common Name | Description | Fold Change | Genbank Accession number | SEQ ID NO |
|---|---|---|---|---|
| NTRK2 | Neurotrophic tyrosine kinase, receptor, type 2 | 4.513 | NM_001007097 | 67 |
| VGLL1 | Vestigial like 1 (Drosophila) | 4.453 | NM_016267 | 68 |
| SPON1 | Spondin 1, extracellular matrix protein | 4.431 | NM_006108 | 69 |
| SEQ_ID_#70 | UI-H-DF1-aug-p-10-0-UI.s1 NCI_CGAP_DF1 Homo sapiens cDNA clone IMAGE: 5869305 3', mRNA sequence. | 4.409 | BM993907 | 70 |
| PRRX1 | Paired related homeobox 1 | 4.375 | NM_006902 | 71 |
| SEQ_ID_#72 | Transcribed locus | 4.374 | AW978130 | 72 |
| SERPINB4 | Serine (or cysteine) proteinase inhibitor, clade B (ovalbumin), member 4 | 4.328 | NM_002974 | 73 |
| RGS13 | Regulator of G-protein signalling 13 | 4.306 | NM_002927 | 74 |
| SLC16A1 | AKR7 family pseudogene | 4.285 | NM_003051 | 75 |
| LOC340061 | Hypothetical protein LOC340061 | 4.211 | NM_198282 | 76 |
| TIMP1 | Tissue inhibitor of metalloproteinase 1 (erythroid potentiating activity, collagenase inhibitor) | 4.158 | NM_003254 | 77 |
| SFRP1 | Secreted frizzled-related protein 1 | 4.098 | NM_003012 | 78 |
| GCNT3 | Glucosaminyl (N-acetyl) transferase 3, mucin type | 4.078 | NM_004751 | 79 |
| SE57-1 | CTCL tumor antigen se57-1 | 4.055 | NM_025214 | 80 |
| GRK5 | G protein-coupled receptor kinase 5 | 3.995 | NM_005308 | 81 |
| SEQ_ID_#82 | UI-H-DF1-aug-p-10-0-UI.s1 NCI_CGAP_DF1 Homo sapiens cDNA clone IMAGE: 5869305 3', mRNA sequence. | 3.968 | BM993907 | 82 |
| ADRBK2 | Adrenergic, beta, receptor kinase 2 | 3.932 | NM_005160 | 83 |
| HTR2B | 5-hydroxytryptamine (serotonin) receptor 2B | 3.91 | NM_000867 | 84 |
| IFI35 | Interferon-induced protein 35 | 3.885 | NM_005533 | 85 |
| IFI27 | Interferon, alpha-inducible protein 27 | 3.873 | NM_005532 | 86 |
| LOC440449 | Hypothetical gene supported by AF086204 | 3.856 | XM_498675 | 87 |
| TPK1 | Thiamin pyrophosphokinase 1 | 3.806 | NM_022445 | 88 |
| GALNT4 | UDP-N-acetyl-alpha-D-galactosamine: polypeptide N-acetylgalactosaminyltransferase 4 (GalNAc-T4) | 3.753 | NM_003774 | 89 |
| PDZK1IP1 | PDZK1 interacting protein 1 | 3.677 | NM_005764 | 90 |
| LOC130576 | Hypothetical protein LOC130576 | 3.669 | NM_177964 | 91 |
| SLC2A3 | Solute carrier family 2 (facilitated glucose transporter), member 3 | 3.657 | NM_006931 | 92 |
| FOXE1 | Forkhead box E1 (thyroid transcription factor 2) | 3.65 | NM_004473 | 93 |
| GABRP | Gamma-aminobutyric acid (GABA) A receptor, pi | 3.65 | NM_014211 | 94 |
| SEQ_ID_#95 | Transcribed locus | 3.633 | BM988338 | 95 |
| TNFSF13 | Tumor necrosis factor (ligand) superfamily, member 12 | 3.62 | NM_003808 | 96 |
| IGFBP3 | Insulin-like growth factor binding protein 3 | 3.605 | NM_000598 | 97 |
| LHFPL2 | Lipoma HMGIC fusion partner-like 2 | 3.591 | NM_005779 | 98 |
| CYP7B1 | Cytochrome P450, family 7, subfamily B, polypeptide 1 | 3.555 | NM_004820 | 99 |
| SLC18A2 | Solute carrier family 18 (vesicular monoamine), member 2 | 3.541 | NM_003054 | 100 |
| KITLG | KIT ligand | 3.538 | NM_000899 | 101 |
| LITAF | Lipopolysaccharide-induced TNF factor | 3.492 | NM_004862 | 102 |
| CDC42EP5 | CDC42 effector protein (Rho GTPase binding) 5 | 3.479 | NM_145057 | 103 |
| KRT23 | Keratin 23 (histone deacetylase inducible) | 3.475 | NM_015515 | 104 |
| EMILIN2 | Elastin microfibril interfacer 2 | 3.473 | NM_032048 | 105 |
| TFPI | Tissue factor pathway inhibitor (lipoprotein-associated coagulation inhibitor) | 3.455 | NM_006287 | 106 |
| LOX | Lysyl oxidase | 3.448 | NM_002317 | 107 |
| PGBD5 | PiggyBac transposable element derived 5 | 3.439 | NM_024554 | 108 |
| IL17RB | Interleukin 17 receptor B | 3.426 | NM_018725 | 109 |
| LOC91353 | Similar to omega protein | 3.416 | NM_001013618 | 110 |
| HS3ST1 | Heparan sulfate (glucosamine) 3-O-sulfotransferase 1 | 3.402 | NM_005114 | 111 |
| RARRES3 | Retinoic acid receptor responder (tazarotene induced) 3 | 3.397 | NM_004585 | 112 |
| HAS3 | Decreased expression in renal and prostate | 3.391 | NM_005329 | 113 |
| GPRC5B | G protein-coupled receptor, family C, group 5, member B | 3.384 | NM_016235 | 114 |
| NRXN1 | Neurexin 1 | 3.372 | NM_004801 | 115 |
| SEQ_ID_#116 | Transcribed locus | 3.363 | AW195474 | 116 |

TABLE 1-continued

The EE transcriptome

| Common Name | Description | Fold Change | Genbank Accession number | SEQ ID NO |
|---|---|---|---|---|
| LOXL4 | Lysyl oxidase-like 4 | 3.336 | NM_032211 | 117 |
| PRG1 | Proteoglycan 1, secretory granule | 3.295 | NM_002727 | 118 |
| MFHAS1 | Malignant fibrous histiocytoma amplified sequence 1 | 3.29 | NM_004225 | 119 |
| SECTM1 | Secreted and transmembrane 1 | 3.282 | NM_003004 | 120 |
| CISH | Cytokine inducible SH2-containing protein | 3.274 | NM_145071 | 121 |
| CFHL1 | Complement factor H-related 1 pseudogene | 3.251 | NM_002113 | 122 |
| HDC | Histidine decarboxylase | 3.243 | NM_002112 | 123 |
| SIGLEC6 | Sialic acid binding Ig-like lectin 6 | 3.199 | NM_001245 | 124 |
| GPR110 | G protein-coupled receptor 110 | 3.193 | NM_153840 | 125 |
| SCIN | Scinderin | 3.17 | NM_033128 | 126 |
| SGK | Serum/glucocorticoid regulated kinase | 3.139 | NM_005627 | 127 |
| SH3RF2 | SH3 domain containing ring finger 2 | 3.122 | NM_152550 | 128 |
| SH2D1B | SH2 domain containing 1B | 3.098 | NM_053282 | 129 |
| Cep72 | Centrosomal protein 72 kDa | 3.081 | NM_018140 | 130 |
| FETUB | Fetuin B | 3.065 | NM_014375 | 131 |
| RGS1 | Regulator of G-protein signalling 1 | 3.056 | NM_002922 | 132 |
| APOBEC3B | Apolipoprotein B mRNA editing enzyme, catalytic polypeptide-like 3D | 3.039 | NM_004900 | 133 |
| MGC48998 | Chromosome 1 open reading frame 110 | 3.036 | NM_178550 | 134 |
| CDH3 | Cadherin 3, type 1, P-cadherin (placental) | 3.026 | NM_001793 | 135 |
| DPYD | Dihydropyrimidine dehydrogenase | 3.015 | NM_000110 | 136 |
| EGLN3 | Egl nine homolog 3 (*C. elegans*) | 3.003 | NM_022073 | 137 |
| PTGES | Prostaglandin E synthase | 2.972 | NM_004878 | 138 |
| KIAA1126 | KIAA1126 protein | 2.944 | AB032952 | 139 |
| LOH11CR2A | Loss of heterozygosity, 11, chromosomal region 2, gene A | 2.938 | NM_198315 | 140 |
| CYP2S1 | Cytochrome P450, family 2, subfamily S, polypeptide 1 | 2.911 | NM_030622 | 141 |
| SEQ_ID_#142 | UI-E-CL1-afe-h-18-0-UI.r1 UI-E-CL1 *Homo sapiens* cDNA clone UI-E-CL1-afe-h-18-0-UI 5′, mRNA sequence. | 2.896 | BM703543 | 142 |
| LBH | Likely ortholog of mouse limb-bud and heart gene | 2.895 | NM_030915 | 143 |
| MGC35033 | Hypothetical protein MGC35033 | 2.875 | NM_152319 | 144 |
| CTSG | Cathepsin G | 2.869 | NM_001911 | 145 |
| SEQ_ID_#146 | | 2.864 | XM_375695 | 146 |
| STOM | Stomatin | 2.846 | NM_004099 | 147 |
| PSMB9 | Proteasome (prosome, macropain) subunit, beta type, 9 (large multifunctional protease 2) | 2.845 | NM_002800 | 148 |
| ATF3 | isoform 3 is encoded by transcript variant 3; ATF3deltaZip3; ATF3deltaZip2c; go_component: nucleus [goid 0005634] [evidence IEA]; go_function: DNA binding [goid 0003677] [evidence IEA]; go_function: transcription factor activity [goid 0003700] [evidence TAS] [pmid 7515060]; go_function: transcription corepressor activity [goid 0003714] [evidence TAS] [pmid 7515060]; go_process: transcription [goid 0006350] [evidence IEA]; go_process: regulation of transcription, DNA-dependent [goid 0006355] [evidence IEA]; *Homo sapiens* activating transcription factor 3 (ATF3), transcript variant 3, mRNA. | 2.844 | NM_001030287 | 149 |
| MMP28 | Matrix metalloproteinase 28 | 2.839 | NM_024302 | 150 |
| SLC15A1 | Solute carrier family 15 (oligopeptide transporter), member 1 | 2.792 | NM_005073 | 151 |
| AIM2 | Absent in melanoma 2 | 2.788 | NM_004833 | 152 |
| KIT | V-kit Hardy-Zuckerman 4 feline sarcoma viral oncogene homolog | 2.776 | NM_000222 | 153 |
| IL15 | Interleukin 15 | 2.772 | NM_000585 | 154 |
| RASGRP1 | RAS guanyl releasing protein 1 (calcium and DAG-regulated) | 2.769 | NM_005739 | 155 |
| SLC27A2 | Solute carrier family 27 (fatty acid transporter), member 2 | 2.766 | NM_003645 | 156 |
| IFIT3 | Interferon-induced protein with tetratricopeptide repeats 3 | 2.763 | NM_001549 | 157 |
| LRRC8D | Leucine rich repeat containing 8 family, member D | 2.761 | NM_018103 | 158 |
| COL8A2 | Collagen, type VIII, alpha 2 | 2.756 | NM_005202 | 159 |
| DUOX1 | Dual oxidase 1 | 2.755 | NM_017434 | 160 |

TABLE 1-continued

The EE transcriptome

| Common Name | Description | Fold Change | Genbank Accession number | SEQ ID NO |
|---|---|---|---|---|
| AYTL3 | PLSC domain containing protein | 2.749 | NM_153613 | 161 |
| F13A1 | Coagulation factor XIII, A1 polypeptide | 2.746 | NM_000129 | 162 |
| ACSL5 | Acyl-CoA synthetase long-chain family member 5 | 2.745 | NM_016234 | 163 |
| GCNT2 | Glucosaminyl (N-acetyl) transferase 2, I-branching enzyme | 2.742 | NM_001491 | 164 |
| SEQ_ID_#165 | Transcribed locus, moderately similar to XP_517655.1 PREDICTED: similar to KIAA0825 protein [*Pan troglodytes*] | 2.732 | BM929354 | 165 |
| TMPRSS4 | Transmembrane protease, serine 4 | 2.719 | NM_019894 | 166 |
| MRC1 | Mannose receptor, C type 1 | 2.717 | NM_002438 | 167 |
| NCF2 | Neutrophil cytosolic factor 2 (65 kDa, chronic granulomatous disease, autosomal 2) | 2.712 | NM_000433 | 168 |
| CSF2RB | Colony stimulating factor 2 receptor, beta, low-affinity (granulocyte-macrophage) | 2.707 | NM_000395 | 169 |
| GULP1 | GULP, engulfment adaptor PTB domain containing 1 | 2.691 | NM_016315 | 170 |
| SCUBE1 | Signal peptide, CUB domain, EGF-like 1 | 2.689 | NM_173050 | 171 |
| NFE2L3 | Nuclear factor (erythroid-derived 2)-like 3 | 2.688 | NM_004289 | 172 |
| PSMB8 | Proteasome (prosome, macropain) subunit, beta type, 8 (large multifunctional protease 7) | 2.687 | NM_004159 | 173 |
| LY96 | Lymphocyte antigen 96 | 2.678 | NM_015364 | 174 |
| PSTPIP2 | Proline-serine-threonine phosphatase interacting protein 2 | 2.675 | NM_024430 | 175 |
| CTSS | Cathepsin S | 2.67 | NM_004079 | 176 |
| GGH | Gamma-glutamyl hydrolase (conjugase, folylpolygammaglutamyl hydrolase) | 2.665 | NM_003878 | 177 |
| SERPINE2 | Serine (or cysteine) proteinase inhibitor, clade E (nexin, plasminogen activator inhibitor type 1), member 2 | 2.66 | NM_006216 | 178 |
| GALNT5 | UDP-N-acetyl-alpha-D-galactosamine: polypeptide N-acetylgalactosaminyltransferase 5 (GalNAc-T5) | 2.648 | NM_014568 | 179 |
| CNTN4 | Contactin 4 | 2.643 | NM_175607 | 180 |
| TPPP | Brain-specific protein p25 alpha | 2.639 | NM_007030 | 181 |
| ZDHHC11 | Zinc finger, DHHC-type containing 11 | 2.631 | NM_024786 | 182 |
| BCL2A1 | BCL2-related protein A1 | 2.621 | NM_004049 | 183 |
| GRM7 | Glutamate receptor, metabotropic 7 | 2.62 | BC009905 | 184 |
| SEQ_ID_#185 | UI-H-BI4-apt-c-08-0-UI.s1 NCI_CGAP_Sub8 *Homo sapiens* cDNA clone IMAGE: 3088503 3', mRNA sequence. | 2.62 | BF511924 | 185 |
| SEQ_ID_#186 | Transcribed locus | 2.617 | BF025845 | 186 |
| TSPAN3 | Tetraspanin 3 | 2.614 | NM_005724 | 187 |
| ADAM28 | A disintegrin and metalloproteinase domain 28 | 2.613 | NM_014265 | 188 |
| SEPX1 | Selenoprotein X, 1 | 2.611 | NM_016332 | 189 |
| IL27RA | Interleukin 27 receptor, alpha | 2.606 | NM_004843 | 190 |
| NAV1 | Neuron navigator 1 | 2.603 | NM_020443 | 191 |
| MET | Met proto-oncogene (hepatocyte growth factor receptor) | 2.592 | NM_000245 | 192 |
| SEQ_ID_#193 | cs100c01.y1 Human Retinal pigment epithelium/choroid cDNA (Un-normalized, unamplified): cs *Homo sapiens* cDNA clone cs100c01 5', mRNA sequence. | 2.591 | CA389545 | 193 |
| SOCS3 | Suppressor of cytokine signaling 3 | 2.589 | NM_003955 | 194 |
| ID3 | Inhibitor of DNA binding 3, dominant negative helix-loop-helix protein | 2.584 | NM_002167 | 195 |
| BID | BH3 interacting domain death agonist | 2.582 | NM_001196 | 196 |
| THEDC1 | Thioesterase domain containing 1 | 2.568 | NM_018324 | 197 |
| LR8 | LR8 protein | 2.564 | NM_014020 | 198 |
| CEL | Carboxyl ester lipase (bile salt-stimulated lipase) | 2.557 | NM_001807 | 199 |
| CALML4 |  | 2.555 | NM_001031733 | 200 |
| LOC387882 | LOC387882 hypothetical protein | 2.551 | NM_207376 | 201 |
| NEK6 | NIMA (never in mitosis gene a)-related kinase 6 | 2.513 | NM_014397 | 202 |
| NCF1 | Neutrophil cytosolic factor 1 (47 kDa, chronic granulomatous disease, autosomal 1) | 2.509 | NM_000265 | 203 |
| DDX58 | DEAD (Asp-Glu-Ala-Asp) box polypeptide 58 | 2.506 | NM_014314 | 204 |
| CLDN23 | Claudin 23 | 2.505 | NM_194284 | 205 |

TABLE 1-continued

The EE transcriptome

| Common Name | Description | Fold Change | Genbank Accession number | SEQ ID NO |
|---|---|---|---|---|
| FA2H | Fatty acid 2-hydroxylase | 2.497 | NM_024306 | 206 |
| LOC286002 | Hypothetical protein LOC286002 | 2.483 | BC037315 | 207 |
| IFITM3 | Interferon induced transmembrane protein 3 (1-8U) | 2.456 | NM_021034 | 208 |
| MDK | Midkine (neurite growth-promoting factor 2) | 2.45 | NM_001012333 | 209 |
| KIAA1337 | Patched domain containing 2 | 2.445 | XM_052561 | 210 |
| VDR | Vitamin D (1,25-dihydroxyvitamin D3) receptor | 2.441 | NM_000376 | 211 |
| MGC14595 | Hypothetical protein MGC14595 | 2.44 | NM_032334 | 212 |
| CHKB | Choline kinase beta | 2.433 | NM_152253 | 213 |
| APOL3 | Apolipoprotein L, 3 | 2.426 | NM_014349 | 214 |
| EDAR | Ectodysplasin A receptor | 2.425 | NM_022336 | 215 |
| SEQ_ID_#216 | CDNA FLJ31134 fis, clone IMR322000984 | 2.423 | AK095590 | 216 |
| BRDG1 | BCR downstream signaling 1 | 2.418 | NM_012108 | 217 |
| FMO1 | Flavin containing monooxygenase 1 | 2.412 | NM_002021 | 218 |
| ASS | Argininosuccinate synthetase | 2.41 | NM_000050 | 219 |
| GPRC5A | G protein-coupled receptor, family C, group 5, member A | 2.406 | NM_003979 | 220 |
| LOC113179 | Secretory carrier membrane protein 4 | 2.403 | NM_138422 | 221 |
| TAPBP | TAP binding protein (tapasin) | 2.401 | NM_003190 | 222 |
| UTS2 | Urotensin 2 | 2.401 | NM_006786 | 223 |
| LYPDC1 | LY6/PLAUR domain containing 1 | 2.399 | NM_144586 | 224 |
| MICB | MHC class I polypeptide-related sequence B | 2.394 | NM_005931 | 225 |
| GPX4 | Glutathione peroxidase 4 (phospholipid hydroperoxidase) | 2.393 | NM_002085 | 226 |
| TMCC3 | Transmembrane and coiled-coil domain family 3 | 2.39 | NM_020698 | 227 |
| TRIM22 | Tripartite motif-containing 22 | 2.387 | NM_006074 | 228 |
| SUV420H1 | Suppressor of variegation 4-20 homolog 1 (Drosophila) | 2.384 | NM_017635 | 229 |
| CFH | Complement factor H | 2.383 | NM_001014975 | 230 |
| FLJ41603 | FLJ41603 protein | 2.378 | NM_001001669 | 231 |
| SLC4A11 | Solute carrier family 4, sodium bicarbonate transporter-like, member 11 | 2.363 | NM_032034 | 232 |
| C1QB | Complement component 1, q subcomponent, beta polypeptide | 2.351 | NM_000491 | 233 |
| FLJ35880 | Hypothetical protein FLJ35880 | 2.349 | NM_153264 | 234 |
| IGLL3; 16.1 | Human germline gene 16.1 for Ig lambda L-chain C region (IgL-C16.1). | 2.342 | X03529 | 235 |
| SEQ_ID_#239 | yc17g11.s1 Stratagene lung (#937210) Homo sapiens cDNA clone IMAGE: 80996 3', mRNA sequence. | 2.342 | T70087 | 236 |
| PLAUR | Plasminogen activator, urokinase receptor | 2.334 | NM_001005377 | 237 |
| OR2A20P | Olfactory receptor, family 2, subfamily A, member 20 pseudogene | 2.327 | BC016940 | 238 |
| MAP3K14 | Mitogen-activated protein kinase kinase kinase 14 | 2.318 | NM_003954 | 239 |
| GATA2 | GATA binding protein 2 | 2.315 | NM_032638 | 240 |
| BIRC4BP | XIAP associated factor-1 | 2.315 | NM_017523 | 241 |
| LOC388610 | Hypothetical LOC388610 | 2.311 | NM_001013642 | 242 |
| SEQ_ID_#243 | AGENCOURT_6466806 NIH_MGC_88 Homo sapiens cDNA clone IMAGE: 5561432 5', mRNA sequence. | 2.308 | BM479034 | 243 |
| SOCS1 | Suppressor of cytokine signaling 1 | 2.306 | NM_003745 | 244 |
| SEQ_ID_#245 | oc22e04.s1 NCI_CGAP_GCB1 Homo sapiens cDNA clone IMAGE: 1350462 3' similar to contains Alu repetitive element; contains element PTR5 repetitive element;, mRNA sequence. | 2.303 | AA806368 | 245 |
| SDPR | Serum deprivation response (phosphatidylserine binding protein) | 2.293 | NM_004657 | 246 |
| HLF | Hepatic leukemia factor | 2.283 | NM_002126 | 247 |
| SCARA3 | Scavenger receptor class A, member 3 | 2.282 | NM_182826 | 248 |
| SMILE | SMILE protein | 2.28 | NM_181783 | 249 |
| FGG | Fibrinogen gamma chain | 2.272 | NM_021870 | 250 |
| IFITM1 | Interferon induced transmembrane protein 1 (9-27) | 2.269 | NM_003641 | 251 |
| CASP7 | Caspase 7, apoptosis-related cysteine protease | 2.266 | NM_001227 | 252 |
| SEQ_ID_#253 | Transcribed locus | 2.264 | CA306881 | 253 |
| PSMB10 | Proteasome (prosome, macropain) subunit, beta type, 10 | 2.261 | NM_002801 | 254 |
| UCP2 | Uncoupling protein 2 (mitochondrial, proton carrier) | 2.259 | NM_003355 | 255 |

TABLE 1-continued

The EE transcriptome

| Common Name | Description | Fold Change | Genbank Accession number | SEQ ID NO |
|---|---|---|---|---|
| IGSF4 | Immunoglobulin superfamily, member 4 | 2.258 | NM_014333 | 256 |
| RARB | Retinoic acid receptor, beta | 2.253 | NM_000965 | 257 |
| LRP1 | Low density lipoprotein-related protein 1 (alpha-2-macroglobulin receptor) | 2.248 | NM_002332 | 258 |
| IFITM2 | Interferon induced transmembrane protein 2 (1-8D) | 2.244 | NM_006435 | 259 |
| PARP14 | Poly (ADP-ribose) polymerase family, member 14 | 2.243 | NM_017554 | 260 |
| SOS1 | Son of sevenless homolog 1 (Drosophila) | 2.243 | NM_005633 | 261 |
| NTRK3 | Neurotrophic tyrosine kinase, receptor, type 3 | 2.24 | NM_002530 | 262 |
| PRICKLE2 | Prickle-like 2 (Drosophila) | 2.237 | NM_198859 | 263 |
| ARMCX3 | Armadillo repeat containing, X-linked 3 | 2.234 | NM_016607 | 264 |
| ECGF1 | Endothelial cell growth factor 1 (platelet-derived) | 2.221 | NM_001953 | 265 |
| TNS4 | Tensin 4 | 2.216 | NM_032865 | 266 |
| FBXO6 | F-box protein 6 | 2.216 | NM_018438 | 267 |
| APOL2 | Apolipoprotein L, 2 | 2.213 | NM_030882 | 268 |
| LY75 | Lymphocyte antigen 75 | 2.212 | NM_002349 | 269 |
| C10orf128 | Chromosome 10 open reading frame 128 | 2.198 | BC047724 | 270 |
| RRM2 | Ribonucleotide reductase M2 polypeptide | 2.197 | NM_001034 | 271 |
| GPCR5A | G protein-coupled receptor, family C, group 5, member A | 2.197 | NM_003979 | 272 |
| HSPA5BP1 | Heat shock 70 kDa protein 5 (glucose-regulated protein, 78 kDa) binding protein 1 | 2.193 | NM_017870 | 273 |
| GLCCI1; GIG18 | synonym: GIG18; Homo sapiens glucocorticoid induced transcript 1 (GLCCI1), mRNA. | 2.191 | XM_166529 | 274 |
| CD52 | CD52 antigen (CAMPATH-1 antigen) | 2.184 | NM_001803 | 275 |
| ADA | Adenosine deaminase | 2.183 | NM_000022 | 276 |
| CXCL16 | Chemokine (C-X-C motif) ligand 16 | 2.179 | NM_022059 | 277 |
| IFIH1 | Interferon induced with helicase C domain 1 | 2.174 | NM_022168 | 278 |
| ZSWIM5 | Zinc finger, SWIM-type containing 5 | 2.169 | XM_046581 | 279 |
| VMP1 | Transmembrane protein 49 | 2.168 | NM_030938 | 280 |
| UBE2L6 | Ubiquitin-conjugating enzyme E2L 6 | 2.164 | NM_004223 | 281 |
| ARHGAP8; PRR5; PP610; BPGAP1; FLJ20185 | Rho GTPase activating protein 8 | 2.164 | NM_017701 | 282 |
| IRF1 | Interferon regulatory factor 1 | 2.161 | NM_002198 | 283 |
| C1orf188 | Hypothetical protein FLJ32096 | 2.157 | NM_173795 | 284 |
| IFI30 | Interferon, gamma-inducible protein 30 | 2.155 | NM_006332 | 285 |
| PLCD3 | Phospholipase C, delta 3 | 2.152 | NM_133373 | 286 |
| WFDC5 | WAP four-disulfide core domain 5 | 2.148 | NM_145652 | 287 |
| SEQ_ID_#288 | AGENCOURT_8217637 Lupski_sympathetic_trunk Homo sapiens cDNA clone IMAGE: 6187901 5', mRNA sequence. | 2.146 | BQ717725 | 288 |
| SIGLECP3 | Sialic acid binding Ig-like lectin, pseudogene 3 | 2.144 | BC035688 | 289 |
| IFPS | Ifapsoriasin | 2.142 | NM_001014342 | 290 |
| CD14 | CD14 antigen | 2.138 | NM_000591 | 291 |
| LOC441168 | Hypothetical protein LOC441168 | 2.136 | NM_001010919 | 292 |
| FCER1G | Fc fragment of IgE, high affinity I, receptor for; gamma polypeptide | 2.135 | NM_004106 | 293 |
| CD44 | CD44 antigen (homing function and Indian blood group system) | 2.132 | NM_000610 | 294 |
| SEQ_ID_#295 | CDNA FLJ44380 fis, clone TRACH3035482 | 2.128 | AK126351 | 295 |
| STAB1 | Stabilin 1 | 2.127 | NM_015136 | 296 |
| ITGAM | Integrin, alpha M (complement component receptor 3, alpha; also known as CD11b (p170), macrophage antigen alpha polypeptide) | 2.126 | NM_000632 | 297 |
| CBX6 | Chromobox homolog 6 | 2.126 | NM_014292 | 298 |
| CYP2E1 | Cytochrome P450, family 2, subfamily E, polypeptide 1 | 2.118 | NM_000773 | 299 |
| C1orf74 | Chromosome 1 open reading frame 74 | 2.117 | NM_152485 | 300 |
| LILRB1 | Leukocyte immunoglobulin-like receptor, subfamily B (with TM and ITIM domains), member 1 | 2.115 | NM_006669 | 301 |
| BAK1 | BCL2-antagonist/killer 1 | 2.114 | NM_001188 | 302 |
| HCP5 | HLA complex P5 | 2.113 | NM_006674 | 303 |
| PLA2G3 | Phospholipase A2, group III | 2.112 | NM_015715 | 304 |
| NXN | Nucleoredoxin | 2.107 | NM_022463 | 305 |
| RRAS | Related RAS viral (r-ras) oncogene homolog | 2.094 | NM_006270 | 306 |

TABLE 1-continued

The EE transcriptome

| Common Name | Description | Fold Change | Genbank Accession number | SEQ ID NO |
|---|---|---|---|---|
| ESR1 | Estrogen receptor 1 | 2.088 | NM_000125 | 307 |
| LOC152485 | Hypothetical protein LOC152485 | 2.086 | NM_178835 | 308 |
| PITX2 | Paired-like homeodomain transcription factor 2 | 2.085 | NM_000325 | 309 |
| SLCO3A1 | Solute carrier organic anion transporter family, member 3A1 | 2.081 | NM_013272 | 310 |
| PARP12 | Poly (ADP-ribose) polymerase family, member 12 | 2.078 | NM_022750 | 311 |
| TAP1 | Transporter 1, ATP-binding cassette, sub-family B (MDR/TAP) | 2.076 | NM_000593 | 312 |
| SEQ_ID_#313 | Transcribed locus | 2.075 | BU689688 | 313 |
| RPRC1 | Arginine/proline rich coiled-coil 1 | 2.074 | NM_018067 | 314 |
| BTN3A3 | Butyrophilin, subfamily 3, member A3 | 2.073 | NM_006994 | 315 |
| UBE1L | Ubiquitin-activating enzyme E1-like | 2.07 | NM_003335 | 316 |
| RRAD | Ras-related associated with diabetes | 2.069 | NM_004165 | 317 |
| PLCE1 | Phospholipase C, epsilon 1 | 2.069 | NM_016341 | 318 |
| SEQ_ID_#319 | 601123374F1 NIH_MGC_5 Homo sapiens cDNA clone IMAGE: 3348067 5', mRNA sequence. | 2.069 | BE749174 | 319 |
| CAPN14 | Calpain 14 | 2.067 | AK092257 | 320 |
| ELOVL5 | ELOVL family member 5, elongation of long chain fatty acids (FEN1/Elo2, SUR4/Elo3-like, yeast) | 2.065 | NM_021814 | 321 |
| GPR143 | G protein-coupled receptor 143 | 2.06 | NM_000273 | 322 |
| SMTN | Smoothelin | 2.046 | NM_134269 | 323 |
| FLJ14466 | Hypothetical protein FLJ14466 | 2.045 | NM_032790 | 324 |
| LOC285016; PRO1097; RGPG542 | synonyms: PRO1097, RGPG542; Homo sapiens hypothetical protein LOC285016 (LOC285016), mRNA. | 2.045 | XM_211736 | 325 |
| APOL6 | Apolipoprotein L, 6 | 2.042 | NM_030641 | 326 |
| ADAM8 | A disintegrin and metalloproteinase domain 8 | 2.041 | NM_001109 | 327 |
| C1orf186 | Hypothetical gene supported by AK122631; BC071785 | 2.035 | NM_001007544 | 328 |
| ABHD4 | Abhydrolase domain containing 4 | 2.03 | NM_022060 | 329 |
| GSDML | Gasdermin-like | 2.029 | NM_018530 | 330 |
| SEQ_ID_#331 | UI-H-BI4-apu-h-06-0-UI.s1 NCI_CGAP_Sub8 Homo sapiens cDNA clone IMAGE: 3088762 3', mRNA sequence. | 2.029 | BF512055 | 331 |
| MYCPBP | C-myc promoter binding protein | 2.028 | NM_005848 | 332 |
| C1QA | Complement component 1, q subcomponent, alpha polypeptide | 2.023 | NM_015991 | 333 |
| SLC16A2 | Solute carrier family 16 (monocarboxylic acid transporters), member 2 | 2.019 | NM_006517 | 334 |
| C10orf47 | Chromosome 10 open reading frame 47 | 2.019 | NM_153256 | 335 |
| GBP4 | Guanylate binding protein 4 | 2.018 | NM_052941 | 336 |
| ARHGEF6 | Rac/Cdc42 guanine nucleotide exchange factor (GEF) 6 | 2.013 | NM_004840 | 337 |
| LILRB2 | Leukocyte immunoglobulin-like receptor, subfamily B (with TM and ITIM domains), member 2 | 2.012 | NM_005874 | 338 |
| SEQ_ID_#339 | | 2.009 | AL121896 | 339 |
| NFKBIE | Nuclear factor of kappa light polypeptide gene enhancer in B-cells inhibitor, epsilon | 2.007 | NM_004556 | 340 |
| SEQ_ID_#341 | EST387291 MAGE resequences, MAGN Homo sapiens cDNA, mRNA sequence. | 2.007 | AW975183 | 341 |
| EHD2 | EH-domain containing 2 | 2.004 | NM_014601 | 342 |
| CCDC34 | NY-REN-41 antigen | 2.004 | NM_030771 | 343 |
| BAZ2A | Bromodomain adjacent to zinc finger domain, 2A | 1.992 | NM_013449 | 344 |
| CAPN3 | Glucosidase, alpha; neutral C | 1.989 | NM_000070 | 345 |
| MVP | Major vault protein | 1.988 | NM_005115 | 346 |
| SIGLEC10 | Sialic acid binding Ig-like lectin 10 | 1.988 | NM_033130 | 347 |
| ARID5B | AT rich interactive domain 5B (MRF1-like) | 1.988 | AI289774 | 348 |
| ZC3H12A | Zinc finger CCCH-type containing 12A | 1.987 | NM_025079 | 349 |
| AP2M1 | Adaptor-related protein complex 2, mu 1 subunit | 1.982 | NM_001025205 | 350 |
| MX1 | Myxovirus (influenza virus) resistance 1, interferon-inducible protein p78 (mouse) | 1.98 | NM_002462 | 351 |
| PDLIM4 | PDZ and LIM domain 4 | 1.977 | NM_003687 | 352 |
| OAS2 | 2'-5'-oligoadenylate synthetase 2, 69/71 kDa | 1.974 | NM_016817 | 353 |
| MKI67 | Antigen identified by monoclonal antibody Ki-67 | 1.971 | NM_002417 | 354 |

TABLE 1-continued

The EE transcriptome

| Common Name | Description | Fold Change | Genbank Accession number | SEQ ID NO |
|---|---|---|---|---|
| RBPMS | RNA binding protein with multiple splicing | 1.971 | NM_001008710 | 355 |
| PARP9 | Poly (ADP-ribose) polymerase family, member 9 | 1.968 | NM_031458 | 356 |
| ABCC5 | ATP-binding cassette, sub-family C (CFTR/MRP), member 5 | 1.961 | NM_005688 | 357 |
| CLDN1 | Claudin 1 | 1.961 | AV659222 | 358 |
| T3JAM | TRAF3 interacting protein 3 | 1.958 | NM_025228 | 359 |
| IKBKAP | Inhibitor of kappa light polypeptide gene enhancer in B-cells, kinase complex-associated protein | 1.955 | NM_003640 | 360 |
| FAM46A | Family with sequence similarity 46, member A | 1.955 | NM_017633 | 361 |
| CHST9 | Carbohydrate (N-acetylgalactosamine 4-0) sulfotransferase 9 | 1.954 | NM_031422 | 362 |
| KIAA1272 | Chromosome 20 open reading frame 74 | 1.953 | AY007156 | 363 |
| NIP | Homolog of Drosophila Numb-interacting protein | 1.953 | NM_144565 | 364 |
| DRAP1 | Similar to ankyrin | 1.951 | BC018095 | 365 |
| SART2 | Squamous cell carcinoma antigen recognized by T cells 2 | 1.951 | NM_013352 | 366 |
| SPBC25 | Spindle pole body component 25 homolog (S. cerevisiae) | 1.95 | NM_020675 | 367 |
| NFATC2 | Nuclear factor of activated T-cells, cytoplasmic, calcineurin-dependent 2 | 1.949 | NM_173091 | 368 |
| SLC9A3 | Solute carrier family 9 (sodium/hydrogen exchanger), isoform 3 | 1.948 | AL137723 | 369 |
| SEQ_ID_#370 | CDNA: FLJ23006 fis, clone LNG00414 | 1.948 | AK026659 | 370 |
| C6orf173 | Chromosome 6 open reading frame 173 | 1.946 | NM_001012507 | 371 |
| CYP4X1 | Cytochrome P450, family 4, subfamily X, polypeptide 1 | 1.946 | NM_178033 | 372 |
| DUSP10 | Dual specificity phosphatase 10 | 1.945 | NM_007207 | 373 |
| PTPN6 | Protein tyrosine phosphatase, non-receptor type 6 | 1.943 | NM_002831 | 374 |
| FGF11 | Fibroblast growth factor 11 | 1.94 | NM_004112 | 375 |
| NFIL3 | Nuclear factor, interleukin 3 regulated | 1.939 | NM_005384 | 376 |
| CMYA5 | Cardiomyopathy associated 5 | 1.938 | NM_153610 | 377 |
| MGC4677 | Hypothetical protein MGC4677 | 1.938 | NM_052871 | 378 |
| KCNE3 | Potassium voltage-gated channel, Isk-related family, member 3 | 1.937 | NM_005472 | 379 |
| WHSC1 | Wolf-Hirschhorn syndrome candidate 1 | 1.936 | BF509385 | 380 |
| NCF4 | Neutrophil cytosolic factor 4, 40 kDa | 1.935 | NM_000631 | 381 |
| CD300LF | CD300 antigen like family member F | 1.934 | NM_139018 | 382 |
| TMC6 | Epidermodysplasia verruciformis 1 | 1.93 | NM_007267 | 383 |
| AP1G2 | Adaptor-related protein complex 1, gamma 2 subunit | 1.929 | NM_003917 | 384 |
| MGC4368 | | 1.924 | NM_001033046 | 385 |
| LOC441109 | Hypothetical gene supported by AL713721 | 1.923 | XM_499014 | 386 |
| LAPTM5 | Lysosomal associated multispanning membrane protein 5 | 1.923 | NM_006762 | 387 |
| SEQ_ID_#388 | BX438987 Homo sapiens PLACENTA Homo sapiens cDNA clone CS0DE005YG01 3-PRIME, mRNA sequence. | 1.921 | BX438987 | 388 |
| ELF4 | E74-like factor 4 (ets domain transcription factor) | 1.92 | NM_001421 | 389 |
| ARHGEF5 | Rho guanine nucleotide exchange factor (GEF) 5 | 1.919 | NM_001002861 | 390 |
| PRODH | Proline dehydrogenase (oxidase) 1 | 1.913 | NM_016335 | 391 |
| GALNAC4S-6ST | B cell RAG associated protein | 1.913 | NM_015892 | 392 |
| MGC17791 | Tumor necrosis factor, alpha-induced protein 8-like 1 | 1.912 | NM_152362 | 393 |
| BIK | BCL2-interacting killer (apoptosis-inducing) | 1.911 | NM_001197 | 394 |
| FAM54A | Family with sequence similarity 54, member A | 1.911 | NM_138419 | 395 |
| VWA1 | Von Willebrand factor A domain containing 1 | 1.91 | NM_022834 | 396 |
| LOC401115 | Hypothetical gene supported by BC038466; BC062790 | 1.909 | XM_379250 | 397 |
| CD40 | CD40 antigen (TNF receptor superfamily member 5) | 1.907 | NM_001250 | 398 |
| L3MBTL | L(3)mbt-like (Drosophila) | 1.907 | NM_015478 | 399 |
| SAA2 | Serum amyloid A2 | 1.907 | NM_030754 | 400 |

TABLE 1-continued

The EE transcriptome

| Common Name | Description | Fold Change | Genbank Accession number | SEQ ID NO |
|---|---|---|---|---|
| ECT2 | Epithelial cell transforming sequence 2 oncogene | 1.907 | NM_018098 | 401 |
| MOV10 | Mov10, Moloney leukemia virus 10, homolog (mouse) | 1.903 | NM_020963 | 402 |
| FLJ21103 | Hypothetical protein FLJ21103 | 1.903 | NM_024556 | 403 |
| KLRK1 | Killer cell lectin-like receptor subfamily K, member 1 | 1.9 | NM_007360 | 404 |
| SEQ_ID_#405 | CDNA FLJ44429 fis, clone UTERU2015653 | 1.9 | AJ318805 | 405 |
| SCOTIN | Scotin | 1.899 | NM_016479 | 406 |
| WDR51B | WD repeat domain 51B | 1.896 | NM_172240 | 407 |
| FLT3LG | Fms-related tyrosine kinase 3 ligand | 1.896 | NM_001459 | 408 |
| KIAA0493 | KIAA0493 protein | 1.89 | AB007962 | 409 |
| LTA4H | Leukotriene A4 hydrolase | 1.888 | NM_000895 | 410 |
| USP54 | Ubiquitin specific protease 54 | 1.888 | NM_152586 | 411 |
| TACC3 | Transforming, acidic coiled-coil containing protein 3 | 1.888 | NM_006342 | 412 |
| LGALS3BP | Lectin, galactoside-binding, soluble, 3 binding protein | 1.888 | NM_005567 | 413 |
| LOC440288 | Similar to FLJ16518 protein | 1.887 | XM_496075 | 414 |
| G0S2 | Putative lymphocyte G0/G1 switch gene | 1.887 | NM_015714 | 415 |
| CCBL1 | Cysteine conjugate-beta lyase; cytoplasmic (glutamine transaminase K, kyneurenine aminotransferase) | 1.884 | NM_004059 | 416 |
| RGS19 | Regulator of G-protein signalling 19 | 1.883 | NM_005873 | 417 |
| KLHL5 | Kelch-like 5 (Drosophila) | 1.883 | NM_001007075 | 418 |
| VILL | Villin-like | 1.883 | NM_015873 | 419 |
| GLCCI1 | Glucocorticoid induced transcript 1 | 1.881 | NM_138426 | 420 |
| TYROBP | TYRO protein tyrosine kinase binding protein | 1.879 | NM_003332 | 421 |
| CDC2 | Cell division cycle 2, G1 to S and G2 to M | 1.879 | NM_001786 | 422 |
| LOC158402 | Hypothetical protein LOC158402 | 1.878 | AK095652 | 423 |
| PRSS12 | Protease, serine, 12 (neurotrypsin, motopsin) | 1.878 | NM_003619 | 424 |
| SEQ_ID_#425 | Transcribed locus | 1.877 | AI632517 | 425 |
| FAM20C | Family with sequence similarity 20, member C | 1.875 | NM_020223 | 426 |
| GBP2 | Guanylate binding protein 2, interferon-inducible | 1.868 | NM_004120 | 427 |
| SEQ_ID_#428 | CDNA FLJ45384 fis, clone BRHIP3021987 | 1.866 | AK127315 | 428 |
| HIST3H2A | Histone 3, H2a | 1.866 | NM_033445 | 429 |
| OLFML2A | Olfactomedin-like 2A | 1.864 | NM_182487 | 430 |
| TNFSF10 | Tumor necrosis factor (ligand) superfamily, member 10 | 1.862 | NM_003810 | 431 |
| LOC120376 | Hypothetical protein LOC120376 | 1.858 | XM_071712 | 432 |
| EPHA4 | EPH receptor A4 | 1.858 | NM_004438 | 433 |
| DERL2 | Der1-like domain family, member 2 | 1.856 | NM_016041 | 434 |
| CYP2R1 | Cytochrome P450, family 2, subfamily R, polypeptide 1 | 1.852 | NM_024514 | 435 |
| VSNL1 | Visinin-like 1 | 1.85 | NM_003385 | 436 |
| MGAT3 | Mannosyl (beta-1,4-)-glycoprotein beta-1,4-N-acetylglucosaminyltransferase | 1.85 | NM_002409 | 437 |
| CLMN | Calmin (calponin-like, transmembrane) | 1.846 | NM_024734 | 438 |
| HES2 | Hairy and enhancer of split 2 (Drosophila) | 1.841 | NM_019089 | 439 |
| SEQ_ID_#440 | LOC441069 | 1.84 | AK056817 | 440 |
| DDX39 | DEAD (Asp-Glu-Ala-Asp) box polypeptide 39 | 1.839 | NM_005804 | 441 |
| SEQ_ID_#442 | Transcribed locus | 1.839 | AW979271 | 442 |
| PARP8 | Poly (ADP-ribose) polymerase family, member 8 | 1.838 | NM_024615 | 443 |
| CLN5 | Ceroid-lipofuscinosis, neuronal 5 | 1.835 | NM_006493 | 444 |
| HLA-B | Major histocompatibility complex, class I, B | 1.834 | NM_005514 | 445 |
| RAB34 | RAB34, member RAS oncogene family | 1.834 | NM_031934 | 446 |
| BTK | Bruton agammaglobulinemia tyrosine kinase | 1.832 | NM_000061 | 447 |
| AMICA1 | Adhesion molecule, interacts with CXADR antigen 1 | 1.83 | NM_153206 | 448 |
| SEQ_ID_#449 | Transcribed locus | 1.83 | BG771234 | 449 |
| SEQ_ID_#450 | Transcribed locus, weakly similar to XP_517655.1 PREDICTED: similar to KIAA0825 protein [Pan troglodytes] | 1.829 | BG483393 | 450 |
| TNFRSF10B | Tumor necrosis factor receptor superfamily, member 10b | 1.826 | NM_003842 | 451 |
| CEACAM1 | Carcinoembryonic antigen-related cell adhesion molecule 1 (biliary glycoprotein) | 1.821 | NM_001024912 | 452 |

TABLE 1-continued

The EE transcriptome

| Common Name | Description | Fold Change | Genbank Accession number | SEQ ID NO |
|---|---|---|---|---|
| EGFL6 | EGF-like-domain, multiple 6 | 1.821 | NM_015507 | 453 |
| VAMP5 | Vesicle-associated membrane protein 5 (myobrevin) | 1.82 | NM_006634 | 454 |
| FLT1 | Fms-related tyrosine kinase 1 (vascular endothelial growth factor/vascular permeability factor receptor) | 1.82 | NM_002019 | 455 |
| SEQ_ID_#456 | Transcribed locus, weakly similar to XP_498452.1 PREDICTED: hypothetical protein XP_498452 [Homo sapiens] | 1.819 | BQ010718 | 456 |
| GPR82 | G protein-coupled receptor 82 | 1.819 | BX438968 | 457 |
| UQCRC1 | Ubiquinol-cytochrome c reductase core protein I | 1.818 | NM_003365 | 458 |
| RNASE1 | Ribonuclease, RNase A family, 1 (pancreatic) | 1.818 | NM_002933 | 459 |
| NOD27 | Nucleotide-binding oligomerization domains 27 | 1.817 | NM_032206 | 460 |
| PTPNS1 | Protein tyrosine phosphatase, non-receptor type substrate 1 | 1.817 | NM_080792 | 461 |
| 3'HEXO | Three prime histone mRNA exonuclease 1 | 1.817 | NM_153332 | 462 |
| C3AR1 | Complement component 3a receptor 1 | 1.815 | NM_004054 | 463 |
| ITPR3 | Inositol 1,4,5-triphosphate receptor, type 3 | 1.813 | NM_002224 | 464 |
| LRRC8A | Leucine rich repeat containing 8 family, member A | 1.81 | NM_019594 | 465 |
| ST8SIA6; SIAT8F; ST8SIA-VI; ST8Sia VI | synonyms: SIAT8F, ST8SIA-VI, ST8Sia VI; sialyltransferase 8F; sialyltransferase 8F (alpha-2, 8-sialyltransferase); go_component: membrane [goid 0016020] [evidence IEA]; go_component: Golgi stack [goid 0005795] [evidence IEA]; go_component: integral to membrane [goid 0016021] [evidence IEA]; go_function: sialyltransferase activity [goid 0008373] [evidence IEA]; go_process: protein amino acid glycosylation [goid 0006486] [evidence IEA]; Homo sapiens ST8 alpha-N-acetyl-neuraminide alpha-2,8-sialyltransferase 6 (ST8SIA6), mRNA. | 1.81 | XM_291725 | 466 |
| C17orf27 | Chromosome 17 open reading frame 27 | 1.808 | NM_020914 | 467 |
| FBXL18 | F-box and leucine-rich repeat protein 18 | 1.808 | NM_024963 | 468 |
| FOXQ1 | Forkhead box Q1 | 1.807 | NM_033260 | 469 |
| CXorf9 | Chromosome X open reading frame 9 | 1.807 | NM_018990 | 470 |
| TAPBPL | TAP binding protein-like | 1.805 | NM_018009 | 471 |
| FAM50A | Family with sequence similarity 50, member A | 1.805 | NM_004699 | 472 |
| GGA2 | Golgi associated, gamma adaptin ear containing, ARF binding protein 2 | 1.805 | NM_015044 | 473 |
| TLOC1 | Translocation protein 1 | 1.802 | NM_003262 | 474 |
| HLA-E | Major histocompatibility complex, class I, E | 1.801 | NM_005516 | 475 |
| SEQ_ID_#476 | Transcribed locus | 1.8 | BM999272 | 476 |
| TTMP | TPA-induced transmembrane protein | 1.798 | NM_024616 | 477 |
| SEQ_ID_#479 | CDNA FLJ39947 fis, clone SPLEN2024232 | 1.798 | AK097266 | 478 |
| SLC39A8 | Solute carrier family 39 (zinc transporter), member 8 | 1.796 | NM_022154 | 479 |
| E2F2 | E2F transcription factor 2 | 1.796 | NM_004091 | 480 |
| NUP210 | Nucleoporin 210 kDa | 1.796 | NM_024923 | 481 |
| PPAP2C | Phosphatidic acid phosphatase type 2C | 1.795 | NM_003712 | 482 |
| EHMT2 | Euchromatic histone-lysine N-methyltransferase 2 | 1.793 | NM_006709 | 483 |
| RYR2 | Ryanodine receptor 2 (cardiac) | 1.793 | NM_001035 | 484 |
| IL15RA | Interleukin 15 receptor, alpha | 1.793 | NM_002189 | 485 |
| STK6 | Serine/threonine kinase 6 | 1.793 | NM_003600 | 486 |
| LAMB3 | Laminin, beta 3 | 1.792 | NM_000228 | 487 |
| SPTBN1 | Spectrin, beta, non-erythrocytic 1 | 1.792 | NM_003128 | 488 |
| ETV6 | Ets variant gene 6 (TEL oncogene) | 1.791 | NM_001987 | 489 |
| PSMB7 | Proteasome (prosome, macropain) subunit, beta type, 7 | 1.791 | NM_002799 | 490 |
| HMGB3 | synonyms: HMG4, HMG2A, MGC90319; high-mobility group (nonhistone chromosomal) protein 4; non-histone chromosomal protein; go_component: nucleus [goid 0005634] [evidence IEA]; go_component: chromatin [goid 0000785] [evidence IEA]; go_function: | 1.79 | NM_005342 | 491 |

TABLE 1-continued

The EE transcriptome

| Common Name | Description | Fold Change | Genbank Accession number | SEQ ID NO |
|---|---|---|---|---|
| | DNA binding [goid 0003677] [evidence IEA]; go_function: DNA bending activity [goid 0008301] [evidence TAS] [pmid 9598312]; go_process: development [goid 0007275] [evidence TAS] [pmid 9598312]; go_process: regulation of transcription, DNA-dependent [goid 0006355] [evidence IEA]; *Homo sapiens* high-mobility group box 3 (HMGB3), mRNA. | | | |
| DOK3 | Docking protein 3 | 1.79 | NM_024872 | 492 |
| DNAPTP6 | DNA polymerase-transactivated protein 6 | 1.787 | NM_015535 | 493 |
| LOC285835 | Hypothetical protein LOC285835 | 1.787 | BC035656 | 494 |
| CDC20 | CDC20 cell division cycle 20 homolog (*S. cerevisiae*) | 1.781 | NM_001255 | 495 |
| SEQ_ID_#496 | AGENCOURT_7258511 NIH_MGC_71 *Homo sapiens* cDNA clone IMAGE: 5786579 5', mRNA sequence. | 1.781 | BQ219651 | 496 |
| TNFRSF10A | Tumor necrosis factor receptor superfamily, member 10a | 1.78 | NM_003844 | 497 |
| KIF4A | Kinesin family member 4A | 1.779 | NM_012310 | 498 |
| SEQ_ID_#499 | UI-CF-FN0-afk-f-10-0-UI.s1 UI-CF-FN0 *Homo sapiens* cDNA clone UI-CF-FN0-afk-f-10-0-UI 3', mRNA sequence. | 1.777 | CA312567 | 499 |
| SDF2 | Stromal cell-derived factor 2 | 1.776 | NM_006923 | 500 |
| PCCA | Propionyl Coenzyme A carboxylase, alpha polypeptide | 1.776 | NM_000282 | 501 |
| TM7SF1 | Transmembrane 7 superfamily member 1 (upregulated in kidney) | 1.774 | NM_003272 | 502 |
| DKFZP564K1964 | | 1.773 | NM_001033504 | 503 |
| VSIG4 | V-set and immunoglobulin domain containing 4 | 1.771 | NM_007268 | 504 |
| TNIP2 | TNFAIP3 interacting protein 2 | 1.77 | NM_024309 | 505 |
| KIAA0513 | KIAA0513 | 1.768 | NM_014732 | 506 |
| PPM1M | Protein phosphatase 1M (PP2C domain containing) | 1.767 | NM_144641 | 507 |
| EXOC3 | SEC6-like 1 (*S. cerevisiae*) | 1.767 | NM_007277 | 508 |
| PSME2 | Proteasome (prosome, macropain) activator subunit 2 (PA28 beta) | 1.767 | NM_002818 | 509 |
| RAB7 | RAB7, member RAS oncogene family | 1.766 | NM_004637 | 510 |
| SEQ_ID_#511 | CDNA clone IMAGE: 6043059 | 1.764 | BC039021 | 511 |
| TNFRSF14 | Tumor necrosis factor receptor superfamily, member 14 (herpesvirus entry mediator) | 1.763 | NM_003820 | 512 |
| KRT4 | Keratin 4 | 1.762 | NM_002272 | 513 |
| CST3 | Cystatin C (amyloid angiopathy and cerebral hemorrhage) | 1.761 | NM_000099 | 514 |
| MGC19764 | Hypothetical protein MGC19764 | 1.756 | NM_144975 | 515 |
| NUP50 | Nucleoporin 50 kDa | 1.756 | NM_007172 | 516 |
| SFXN1 | Sideroflexin 1 | 1.754 | NM_022754 | 517 |
| BIRC5 | Effector cell protease receptor 1 | 1.753 | NM_001012270 | 518 |
| IL2RG | Interleukin 2 receptor, gamma (severe combined immunodeficiency) | 1.753 | NM_000206 | 519 |
| RIPK2 | Receptor-interacting serine-threonine kinase 2 | 1.751 | NM_003821 | 520 |
| SEQ_ID_#521 | Non-coding transcript, polyA signal, clone 44-5SB/3L | 1.75 | BC040308 | 521 |
| RTKN | Rhotekin | 1.75 | NM_001015055 | 522 |
| NDFIP2 | Nedd4 family interacting protein 2 | 1.749 | NM_019080 | 523 |
| ARRDC2 | Arrestin domain containing 2 | 1.749 | NM_001025604 | 524 |
| EFHD2 | EF-hand domain family, member D2 | 1.747 | NM_024329 | 525 |
| C9orf127 | Chromosome 9 open reading frame 127 | 1.747 | NM_016446 | 526 |
| KIAA1509 | KIAA1509 | 1.747 | XM_029353 | 527 |
| ACPL2 | | 1.744 | NM_001037172 | 528 |
| SEQ_ID_#529 | LOC441069 | 1.742 | AK056817 | 529 |
| FAM100B | Hypothetical protein MGC29814 | 1.742 | NM_182565 | 530 |
| BTG3 | BTG family, member 3 | 1.741 | NM_006806 | 531 |
| PITPNC1 | Phosphatidylinositol transfer protein, cytoplasmic 1 | 1.741 | NM_012417 | 532 |
| RAB40B | RAB40B, member RAS oncogene family | 1.74 | NM_006822 | 533 |
| ICAM4 | Intercellular adhesion molecule 4, Landsteiner-Wiener blood group | 1.738 | NM_001544 | 534 |
| FXYD3 | FXYD domain containing ion transport regulator 3 | 1.736 | NM_005971 | 535 |
| SPSB1 | SPRY domain-containing SOCS box protein SSB-1 | 1.735 | NM_025106 | 536 |

TABLE 1-continued

The EE transcriptome

| Common Name | Description | Fold Change | Genbank Accession number | SEQ ID NO |
|---|---|---|---|---|
| GCH1 | GTP cyclohydrolase 1 (dopa-responsive dystonia) | 1.734 | NM_000161 | 537 |
| SEQ_ID_#538 | IL3-CT0674-060401-492-F11 CT0674 Homo sapiens cDNA, mRNA sequence. | 1.734 | BG960486 | 538 |
| MELK | Maternal embryonic leucine zipper kinase | 1.731 | NM_014791 | 539 |
| KIAA1404 | KIAA1404 protein | 1.731 | NM_021035 | 540 |
| SYNPO | Synaptopodin | 1.73 | NM_007286 | 541 |
| MAN2B1 | Mannosidase, alpha, class 2B, member 1 | 1.729 | NM_000528 | 542 |
| MAOA | Monoamine oxidase A | 1.729 | NM_000240 | 543 |
| CCR3 | Chemokine (C-C motif) receptor 3 | 1.729 | NM_001837 | 544 |
| APBA3 | Amyloid beta (A4) precursor protein-binding, family A, member 3 (X11-like 2) | 1.727 | NM_004886 | 545 |
| OASL | 2'-5'-oligoadenylate synthetase-like | 1.726 | NM_003733 | 546 |
| PAFAH1B3 | Platelet-activating factor acetylhydrolase, isoform Ib, gamma subunit 29 kDa | 1.726 | NM_002573 | 547 |
| ARHGAP18 | Rho GTPase activating protein 18 | 1.725 | NM_033515 | 548 |
| MGC13098 | Hypothetical protein MGC13098 | 1.723 | BX537878 | 549 |
| ARHGAP9 | Rho GTPase activating protein 9 | 1.722 | NM_032496 | 550 |
| INSIG1 | Insulin induced gene 1 | 1.721 | NM_005542 | 551 |
| ADORA3 | Adenosine A3 receptor | 1.72 | NM_000677 | 552 |
| VWF | Von Willebrand factor | 1.717 | NM_000552 | 553 |
| AGTRAP | Angiotensin II receptor-associated protein | 1.716 | NM_020350 | 554 |
| ITGAE | Integrin, alpha E (antigen CD103, human mucosal lymphocyte antigen 1; alpha polypeptide) | 1.715 | NM_002208 | 555 |
| SMAD1 | SMAD, mothers against DPP homolog 1 (Drosophila) | 1.715 | NM_001003688 | 556 |
| RHBDL7 | Rhomboid, veinlet-like 7 (Drosophila) | 1.713 | NM_020684 | 557 |
| HLA-F | Major histocompatibility complex, class I, F | 1.713 | NM_018950 | 558 |
| DTX3L | Deltex 3-like (Drosophila) | 1.711 | NM_138287 | 559 |
| SDK1 | Sidekick homolog 1 (chicken) | 1.708 | NM_152744 | 560 |
| LCK | Lymphocyte-specific protein tyrosine kinase | 1.708 | NM_005356 | 561 |
| CBLC | Cas-Br-M (murine) ecotropic retroviral transforming sequence c | 1.707 | NM_012116 | 562 |
| SEQ_ID_#563 | 601344760F1 NIH_MGC_8 Homo sapiens cDNA clone IMAGE: 3677607 5', mRNA sequence. | 1.706 | BE562274 | 563 |
| CHST7 | Carbohydrate (N-acetylglucosamine 6-O) sulfotransferase 7 | 1.706 | NM_019886 | 564 |
| CDCA2 | Cell division cycle associated 2 | 1.706 | NM_152562 | 565 |
| ACOT9 | | 1.706 | NM_001033583 | 566 |
| TYMS | Thymidylate synthetase | 1.705 | NM_001071 | 567 |
| HCA112 | Hepatocellular carcinoma-associated antigen 112 | 1.705 | NM_018487 | 568 |
| EVER2 | Epidermodysplasia verruciformis 2 | 1.7 | NM_152468 | 569 |
| LAYN | Layilin | 1.7 | NM_178834 | 570 |
| MGC7036 | Hypothetical protein MGC7036 | 1.699 | NM_145058 | 571 |
| FLJ11029 | Hypothetical protein FLJ11029 | 1.699 | NM_018304 | 572 |
| FLJ10996 | synonym: MGC13033; Homo sapiens hypothetical protein FLJ10996 (FLJ10996), mRNA. | 1.696 | NM_031447 | 573 |
| SEQ_ID_#574 | Transcribed locus | 1.695 | BQ010979 | 574 |
| CENPF | Centromere protein F, 350/400ka (mitosin) | 1.693 | NM_016343 | 575 |
| BTN3A2 | Butyrophilin, subfamily 3, member A2 | 1.692 | NM_007047 | 576 |
| GAS2L3 | Growth arrest-specific 2 like 3 | 1.692 | NM_174942 | 577 |
| KRT19 | Keratin 19 | 1.69 | NM_002276 | 578 |
| HLA-C | Major histocompatibility complex, class I, C | 1.689 | NM_002117 | 579 |
| ATP11A | ATPase, Class VI, type 11A | 1.688 | NM_015205 | 580 |
| SEQ_ID_#581 | Transcribed locus, weakly similar to NP_009083.1 zinc finger protein 195 [Homo sapiens] | 1.688 | BI820139 | 581 |
| SEMA4C | Sema domain, immunoglobulin domain (Ig), transmembrane domain (TM) and short cytoplasmic domain, (semaphorin) 4C | 1.688 | NM_017789 | 582 |
| CCNB1 | Cyclin B1 | 1.685 | NM_031966 | 583 |
| CLDN4 | Claudin 4 | 1.684 | NM_001305 | 584 |
| CCM2 | Cerebral cavernous malformation 2 | 1.683 | NM_001029835 | 585 |
| UBE2C | Ubiquitin-conjugating enzyme E2C | 1.682 | NM_007019 | 586 |
| FAM3C | Family with sequence similarity 3, member C | 1.681 | NM_014888 | 587 |

TABLE 1-continued

The EE transcriptome

| Common Name | Description | Fold Change | Genbank Accession number | SEQ ID NO |
|---|---|---|---|---|
| SERTAD4 | SERTA domain containing 4 | 1.681 | NM_019605 | 588 |
| ELF3 | E74-like factor 3 (ets domain transcription factor, epithelial-specific) | 1.68 | NM_004433 | 589 |
| FCGRT | Fc fragment of IgG, receptor, transporter, alpha | 1.678 | NM_004107 | 590 |
| LOC55831 | 30 kDa protein | 1.677 | NM_018447 | 591 |
| APOBEC3C | Apolipoprotein B mRNA editing enzyme, catalytic polypeptide-like 3C | 1.676 | NM_014508 | 592 |
| FAS | Fas (TNF receptor superfamily, member 6) | 1.676 | NM_000043 | 593 |
| RDH10 | Retinol dehydrogenase 10 (all-trans) | 1.675 | NM_172037 | 594 |
| LOC440836 | Endothelial cell growth factor 1 (platelet-derived) | 1.675 | NM_001014440 | 595 |
| TRIM47 | Tripartite motif-containing 47 | 1.675 | NM_033452 | 596 |
| SEQ_ID_#597 | T-cell receptor V beta gene segment V-beta-6, clone IGRb11 | 1.674 | BC035390 | 597 |
| SEQ_ID_#598 | Transcribed locus | 1.673 | BX114460 | 598 |
| 9-Sep | Septin 9 | 1.672 | NM_006640 | 599 |
| DHFR | Dihydrofolate reductase | 1.671 | NM_000791 | 600 |
| SLC39A1 | Solute carrier family 39 (zinc transporter), member 1 | 1.67 | NM_014437 | 601 |
| ARHGAP21 | Rho GTPase activating protein 21 | 1.669 | NM_020824 | 602 |
| FBLN1 | Fibulin 1 | 1.668 | NM_001996 | 603 |
| FOXM1 | Forkhead box M1 | 1.668 | NM_021953 | 604 |
| MGC14289 | Similar to RIKEN cDNA 1200014N16 gene | 1.666 | NM_080660 | 605 |
| SEQ_ID_#606 | UI-E-EJ0-aik-f-24-0-UI.s1 UI-E-EJ0 Homo sapiens cDNA clone UI-E-EJ0-aik-f-24-0-UI 3', mRNA sequence. | 1.666 | BM681765 | 606 |
| ROBO1 | Roundabout, axon guidance receptor, homolog 1 (Drosophila) | 1.666 | NM_002941 | 607 |
| ADAM12 | A disintegrin and metalloproteinase domain 12 (meltrin alpha) | 1.665 | NM_003474 | 608 |
| BDNF | Brain-derived neurotrophic factor opposite strand | 1.664 | NM_001709 | 609 |
| RPS8 | Ribosomal protein S8 | 1.663 | NM_001012 | 610 |
| P2RY2 | Purinergic receptor P2Y, G-protein coupled, 2 | 1.661 | NM_002564 | 611 |
| C9orf55 | Chromosome 9 open reading frame 55 | 1.661 | NM_017925 | 612 |
| IKBKE | Inhibitor of kappa light polypeptide gene enhancer in B-cells, kinase epsilon | 1.661 | NM_014002 | 613 |
| RARA | Retinoic acid receptor, alpha | 1.661 | NM_000964 | 614 |
| ST6GALNAC2 | ST6 (alpha-N-acetyl-neuraminyl-2,3-beta-galactosyl-1,3)-N-acetylgalactosaminide alpha-2,6-sialyltransferase 2 | 1.66 | NM_006456 | 615 |
| NDUFS7 | NADH dehydrogenase (ubiquinone) Fe—S protein 7, 20 kDa (NADH-coenzyme Q reductase) | 1.659 | NM_024407 | 616 |
| LAT | Linker for activation of T cells | 1.659 | NM_001014987 | 617 |
| FLOT1 | Flotillin 1 | 1.658 | NM_005803 | 618 |
| MSMB | Microseminoprotein, beta- | 1.657 | NM_002443 | 619 |
| TRIM11 | Tripartite motif-containing 11 | 1.653 | NM_145214 | 620 |
| SIPA1L1 | Signal-induced proliferation-associated 1 like 1 | 1.653 | NM_015556 | 621 |
| TRAF4 | TNF receptor-associated factor 4 | 1.652 | NM_004295 | 622 |
| FLJ33860 | RP5-1017F8.1; go_function: receptor activity [goid 0004872] [evidence IEA]; Homo sapiens hypothetical protein FLJ33860 (FLJ33860), mRNA. | 1.652 | NM_173644 | 623 |
| WBSCR17 | Williams-Beuren syndrome chromosome region 17 | 1.651 | NM_022479 | 624 |
| RNASEH2A | Ribonuclease H2, large subunit | 1.65 | NM_006397 | 625 |
| BPNT1 | 3'(2'),5'-bisphosphate nucleotidase 1 | 1.649 | NM_006085 | 626 |
| CD3D | CD3D antigen, delta polypeptide (TiT3 complex) | 1.649 | NM_000732 | 627 |
| GBP5 | Guanylate binding protein 5 | 1.647 | NM_052942 | 628 |
| RNF19 | Ring finger protein 19 | 1.646 | NM_015435 | 629 |
| SEQ_ID_#630 | Transcribed locus, moderately similar to XP_508230.1 PREDICTED: zinc finger protein 195 [Pan troglodytes] | 1.642 | BF037662 | 630 |
| DAPK2 | Death-associated protein kinase 2 | 1.641 | NM_014326 | 631 |
| CCNB2 | Glutamate decarboxylase 1 (GAD 1) | 1.641 | NM_004701 | 632 |
| FNTB | Farnesyltransferase, CAAX box, beta | 1.64 | NM_002028 | 633 |
| C16orf7 | Chromosome 16 open reading frame 7 | 1.64 | NM_004913 | 634 |
| NR4A2 | Nuclear receptor subfamily 4, group A, member 2 | 1.637 | NM_006186 | 635 |

TABLE 1-continued

The EE transcriptome

| Common Name | Description | Fold Change | Genbank Accession number | SEQ ID NO |
|---|---|---|---|---|
| PITRM1 | Pitrilysin metalloproteinase 1 | 1.636 | NM_014889 | 636 |
| DOCK7 | Dedicator of cytokinesis 7 | 1.636 | BG546677 | 637 |
| JDP2 | Jun dimerization protein 2 | 1.635 | NM_130469 | 638 |
| SEQ_ID_#639 | 601344760F1 NIH_MGC_8 Homo sapiens cDNA clone IMAGE: 3677607 5', mRNA sequence. | 1.635 | BE562274 | 639 |
| EAP30 | EAP30 subunit of ELL complex | 1.635 | NM_007241 | 640 |
| DAF | Decay accelerating factor for complement (CD55, Cromer blood group system) | 1.634 | NM_000574 | 641 |
| CUEDC2 | CUE domain containing 2 | 1.633 | NM_024040 | 642 |
| PLAU | Plasminogen activator, urokinase | 1.633 | NM_002658 | 643 |
| HDAC9 | Histone deacetylase 9 | 1.632 | NM_014707 | 644 |
| PTCH | Patched homolog (Drosophila) | 1.632 | NM_000264 | 645 |
| TNFRSF25 | Tumor necrosis factor receptor superfamily, member 25 | 1.631 | NM_003790 | 646 |
| TK1 | Thymidine kinase 1, soluble | 1.628 | NM_003258 | 647 |
| FLJ11286 | Hypothetical protein FLJ11286 | 1.628 | NM_018381 | 648 |
| CDCA5 | Cell division cycle associated 5 | 1.628 | NM_080668 | 649 |
| SEMA3B | Sema domain, immunoglobulin domain (Ig), short basic domain, secreted, (semaphorin) 3B | 1.627 | NM_004636 | 650 |
| PCSK6 | Proprotein convertase subtilisin/kexin type 6 | 1.627 | NM_002570 | 651 |
| C8orf72 | Hypothetical protein MGC39325 | 1.626 | NM_147189 | 652 |
| STARD5 | START domain containing 5 | 1.626 | NM_030574 | 653 |
| JUB | Jub, ajuba homolog (Xenopus laevis) | 1.625 | NM_032876 | 654 |
| NAPE-PLD | N-acyl-phosphatidylethanolamine-hydrolyzing phospholipase D | 1.625 | NM_198990 | 655 |
| HIGD2A | Hypothetical protein MGC2198 | 1.625 | NM_138820 | 656 |
| C1RL | Complement component 1, r subcomponent-like | 1.624 | NM_016546 | 657 |
| DKFZP564I0422 | Hypothetical protein DKFZp564I0422 | 1.622 | NM_031435 | 658 |
| SCCPDH | Saccharopine dehydrogenase (putative) | 1.62 | NM_016002 | 659 |
| ZNF503 | Zinc finger protein 503 | 1.616 | AK024492 | 660 |
| PLEKHG3 | Pleckstrin homology domain containing, family G (with RhoGef domain) member 3 | 1.615 | AB011171 | 661 |
| CD209 | CD209 antigen | 1.615 | NM_021155 | 662 |
| HLA-A | Major histocompatibility complex, class I, A | 1.614 | NM_002116 | 663 |
| Cep290 | Centrosome protein cep290 | 1.614 | NM_025114 | 664 |
| KIAA1434 | Hypothetical protein KIAA1434 | 1.612 | NM_019593 | 665 |
| SEQ_ID_#666 | Hypothetical LOC389188 | 1.612 | AK097068 | 666 |
| SEQ_ID_#667 | Hypothetical gene supported by AL713721 | 1.612 | BX648423 | 667 |
| ARHGAP25 | Rho GTPase activating protein 25 | 1.611 | NM_001007231 | 668 |
| TEP1 | Telomerase-associated protein 1 | 1.61 | NM_007110 | 669 |
| HSC20 | J-type co-chaperone HSC20 | 1.61 | NM_172002 | 670 |
| DLG5 | Discs, large homolog 5 (Drosophila) | 1.61 | NM_004747 | 671 |
| H6PD | Hexose-6-phosphate dehydrogenase (glucose 1-dehydrogenase) | 1.61 | NM_004285 | 672 |
| OSBPL3 | Oxysterol binding protein-like 3 | 1.609 | NM_015550 | 673 |
| CDCP1 | CUB domain containing protein 1 | 1.608 | NM_022842 | 674 |
| RCN1 | Reticulocalbin 1, EF-hand calcium binding domain | 1.608 | NM_002901 | 675 |
| BCL6 | B-cell CLL/lymphoma 6 (zinc finger protein 51) | 1.608 | NM_001706 | 676 |
| MGAT4B | Mannosyl (alpha-1,3-)-glycoprotein beta-1,4-N-acetylglucosaminyltransferase, isoenzyme B | 1.607 | NM_014275 | 677 |
| DPEP2 | Dipeptidase 2 | 1.606 | NM_022355 | 678 |
| CLNS1A | Chloride channel, nucleotide-sensitive, 1A | 1.605 | NM_001293 | 679 |
| DEPDC1 | DEP domain containing 1 | 1.605 | NM_017779 | 680 |
| C10orf54 | Cadherin-like 23 | 1.602 | NM_022153 | 681 |
| SMC2L1 | SMC2 structural maintenance of chromosomes 2-like 1 (yeast) | 1.602 | NM_006444 | 682 |
| ATG4D | APG4 autophagy 4 homolog D (S. cerevisiae) | 1.601 | NM_032885 | 683 |
| FAM3B | Family with sequence similarity 3, member B | 1.601 | NM_058186 | 684 |
| TRADD | TNFRSF1A-associated via death domain | 1.601 | NM_003789 | 685 |
| GABARAPL1 | GABA(A) receptor-associated protein like 1 | 1.6 | NM_031412 | 686 |
| TGFBI | Transforming growth factor, beta-induced, 68 kDa | 1.599 | NM_000358 | 687 |
| DAG1 | Dystroglycan 1 (dystrophin-associated glycoprotein 1) | 1.599 | NM_004393 | 688 |
| TBC1D1 | TBC1 (tre-2/USP6, BUB2, cdc16) domain family, member 1 | 1.599 | NM_015173 | 689 |
| TCF4 | Transcription factor 4 | 1.597 | NM_003199 | 690 |
| PLXNA1 | Plexin A1 | 1.597 | NM_032242 | 691 |

TABLE 1-continued

The EE transcriptome

| Common Name | Description | Fold Change | Genbank Accession number | SEQ ID NO |
|---|---|---|---|---|
| CKS2 | CDC28 protein kinase regulatory subunit 2 | 1.597 | NM_001827 | 692 |
| KIAA1295 | KIAA1295 | 1.594 | NM_001017995 | 693 |
| LOC144501 | Hypothetical protein LOC144501 | 1.594 | NM_182507 | 694 |
| MIR16 | Membrane interacting protein of RGS16 | 1.593 | NM_016641 | 695 |
| C7orf19 | synonyms: CBCIP2, FLJ12474, FLJ14733; H_NH0514P08.8; CAP-binding protein complex interacting protein 2; Homo sapiens chromosome 7 open reading frame 19 (C7orf19), mRNA. | 1.592 | NM_025156 | 696 |
| SLC24A6 | Solute carrier family 24 (sodium/potassium/calcium exchanger), member 6 | 1.592 | NM_024959 | 697 |
| ATP5G2 | ATP synthase, H+ transporting, mitochondrial F0 complex, subunit c (subunit 9), isoform 2 | 1.592 | NM_001002031 | 698 |
| AMOTL1 | Angiomotin like 1 | 1.59 | NM_130847 | 699 |
| EPAS1 | Endothelial PAS domain protein 1 | 1.59 | AK023572 | 700 |
| ADAM9 | A disintegrin and metalloproteinase domain 9 (meltrin gamma) | 1.587 | NM_001005845 | 701 |
| HCK | Hemopoietic cell kinase | 1.586 | NM_002110 | 702 |
| ACOX1 | Acyl-Coenzyme A oxidase 1, palmitoyl | 1.585 | NM_004035 | 703 |
| SLC25A28 | Solute carrier family 25, member 28 | 1.585 | NM_031212 | 704 |
| DEF6 | Differentially expressed in FDCP 6 homolog (mouse) | 1.585 | NM_022047 | 705 |
| MYH9 | Myosin, heavy polypeptide 9, non-muscle | 1.584 | NM_002473 | 706 |
| CD300A | CD300A antigen | 1.584 | NM_007261 | 707 |
| CORO1A | Coronin, actin binding protein, 1A | 1.583 | NM_007074 | 708 |
| RPS6KA1 | Ribosomal protein S6 kinase, 90 kDa, polypeptide 1 | 1.583 | NM_001006665 | 709 |
| TRAFD1 | TRAF-type zinc finger domain containing 1 | 1.582 | NM_006700 | 710 |
| NFE2L1 | Nuclear factor (erythroid-derived 2)-like 1 | 1.582 | NM_003204 | 711 |
| SLC35B2 | Solute carrier family 35, member B2 | 1.581 | NM_178148 | 712 |
| ETV7 | Ets variant gene 7 (TEL2 oncogene) | 1.581 | NM_016135 | 713 |
| KIF2C | Kinesin family member 2C | 1.58 | NM_006845 | 714 |
| KIAA0999 | KIAA0999 protein | 1.579 | NM_025164 | 715 |
| NCOA7 | Nuclear receptor coactivator 7 | 1.577 | NM_181782 | 716 |
| IFI16 | Interferon, gamma-inducible protein 16 | 1.577 | NM_005531 | 717 |
| SEQ_ID_#718 | AGENCOURT_10444615 NIH_MGC_82 Homo sapiens cDNA clone IMAGE: 6619338 5', mRNA sequence. | 1.576 | BU852798 | 718 |
| DTNBP1 | Dystrobrevin binding protein 1 | 1.575 | NM_032122 | 719 |
| CD9 | CD9 antigen (p24) | 1.574 | AK025016 | 720 |
| AP4B1 | Adaptor-related protein complex 4, beta 1 subunit | 1.574 | NM_006594 | 721 |
| SLC25A23 | Solute carrier family 25 (mitochondrial carrier; phosphate carrier), member 23 | 1.574 | NM_024103 | 722 |
| CENTD2 | Centaurin, delta 2 | 1.573 | NM_015242 | 723 |
| ATAD2 | ATPase family, AAA domain containing 2 | 1.573 | NM_014109 | 724 |
| SEQ_ID_#725 | CDNA FLJ38412 fis, clone FEBRA2009385 | 1.573 | AK095731 | 725 |
| CIB1 | Calcium and integrin binding 1 (calmyrin) | 1.573 | NM_006384 | 726 |
| C1orf93 | Chromosome 1 open reading frame 93 | 1.568 | NM_152371 | 727 |
| SEQ_ID_#728 | 602281279F1 NIH_MGC_86 Homo sapiens cDNA clone IMAGE: 4368955 5', mRNA sequence. | 1.568 | BG109249 | 728 |
| SITPEC | Signaling intermediate in Toll pathway, evolutionarily conserved | 1.567 | NM_016581 | 729 |
| GUSB | Glucuronidase, beta | 1.566 | NM_000181 | 730 |
| FLJ10260 | Hypothetical protein FLJ10260 | 1.565 | NM_018042 | 731 |
| FSHPRH1 | FSH primary response (LRPR1 homolog, rat) 1 | 1.565 | NM_006733 | 732 |
| AURKB | Aurora kinase B | 1.564 | NM_004217 | 733 |
| USP18 | Ubiquitin specific protease 18 | 1.564 | NM_017414 | 734 |
| PCDH9 | Protocadherin 9 | 1.564 | BC008476 | 735 |
| SFXN3 | Sideroflexin 3 | 1.563 | NM_030971 | 736 |
| TFEB | Transcription factor EB | 1.562 | NM_007162 | 737 |
| BRRN1 | Barren homolog (Drosophila) | 1.561 | NM_015341 | 738 |
| HFE | Hemochromatosis | 1.56 | NM_000410 | 739 |
| NDUFB10 | NADH dehydrogenase (ubiquinone) 1 beta subcomplex, 10, 22 kDa | 1.56 | NM_004548 | 740 |
| FER1L3 | Fer-1-like 3, myoferlin (C. elegans) | 1.559 | NM_013451 | 741 |
| ATP11C | ATPase, Class VI, type 11C | 1.559 | NM_001010986 | 742 |
| LOC128387 | TatD DNase domain containing 3 | 1.557 | XM_375838 | 743 |
| MGC11242 | Hypothetical protein MGC11242 | 1.556 | NM_024320 | 744 |
| NUDT1 | Nudix (nucleoside diphosphate linked moiety X)-type motif 1 | 1.556 | NM_002452 | 745 |

TABLE 1-continued

The EE transcriptome

| Common Name | Description | Fold Change | Genbank Accession number | SEQ ID NO |
|---|---|---|---|---|
| BTG1 | B-cell translocation gene 1, anti-proliferative | 1.556 | NM_001731 | 746 |
| RBMS2 | RNA binding motif, single stranded interacting protein 2 | 1.555 | NM_002898 | 747 |
| C9orf91 | Chromosome 9 open reading frame 91 | 1.554 | NM_153045 | 748 |
| C20orf116 | Chromosome 20 open reading frame 116 | 1.553 | NM_023935 | 749 |
| GSDMDC1 | Gasdermin domain containing 1 | 1.553 | NM_024736 | 750 |
| AYTL2 | Hypothetical protein FLJ12443 | 1.552 | NM_024830 | 751 |
| PVRL2 | Poliovirus receptor-related 2 (herpesvirus entry mediator B) | 1.552 | NM_002856 | 752 |
| DCP2 | DCP2 decapping enzyme homolog (*S. cerevisiae*) | 1.55 | NM_152624 | 753 |
| SAV1 | Salvador homolog 1 (*Drosophila*) | 1.55 | NM_021818 | 754 |
| CANT1 | Calcium activated nucleotidase 1 | 1.55 | NM_138793 | 755 |
| PLEKHG2 | Pleckstrin homology domain containing, family G (with RhoGef domain) member 2 | 1.549 | NM_022835 | 756 |
| IRF6 | Interferon regulatory factor 6 | 1.548 | NM_006147 | 757 |
| PDE4D | Phosphodiesterase 4D, cAMP-specific (phosphodiesterase E3 dunce homolog, *Drosophila*) | 1.547 | NM_006203 | 758 |
| SEQ_ID_#759 | | 1.547 | XM_087056 | 759 |
| KLK10 | Kallikrein 10 | 1.546 | NM_002776 | 760 |
| GSR | Glutathione reductase | 1.545 | NM_000637 | 761 |
| SEQ_ID_#762 | Transcribed locus, moderately similar to XP_498467.1 PREDICTED: hypothetical protein XP_498467 [*Homo sapiens*] | 1.543 | BX108121 | 762 |
| CDC45L | CDC45 cell division cycle 45-like (*S. cerevisiae*) | 1.543 | NM_003504 | 763 |
| IGSF2 | Immunoglobulin superfamily, member 2 | 1.543 | NM_004258 | 764 |
| MYO1F | Myosin IF | 1.542 | NM_012335 | 765 |
| ZFYVE16 | Zinc finger, FYVE domain containing 16 | 1.542 | NM_014733 | 766 |
| RAB31 | RAB31, member RAS oncogene family | 1.541 | NM_006868 | 767 |
| TOMM34 | Translocase of outer mitochondrial membrane 34 | 1.54 | NM_006809 | 768 |
| SEQ_ID_#769 | 602977386F1 NIH_MGC_12 *Homo sapiens* cDNA clone IMAGE: 5122341 5', mRNA sequence. | 1.539 | BI255338 | 769 |
| SEQ_ID_#770 | *Homo sapiens* clone IMAGE: 110987 mRNA sequence. | 1.538 | AF143866 | 770 |
| KIAA1305 | KIAA1305 | 1.536 | XM_370756 | 771 |
| HIP1R | Huntingtin interacting protein-1-related | 1.536 | NM_003959 | 772 |
| PRKD2 | Protein kinase D2 | 1.536 | NM_016457 | 773 |
| ACP2 | Acid phosphatase 2, lysosomal | 1.534 | NM_001610 | 774 |
| COPZ2 | Coatomer protein complex, subunit zeta 2 | 1.533 | NM_016429 | 775 |
| GNG10 | DnaJ-like protein | 1.533 | NM_004125 | 776 |
| SEQ_ID_#777 | Transcribed locus | 1.533 | BX117393 | 777 |
| C1orf85 | Chromosome 1 open reading frame 85 | 1.532 | NM_144580 | 778 |
| NTF5 | Neurotrophin 5 (neurotrophin 4/5) | 1.532 | NM_006179 | 779 |
| KIAA0101 | synonyms: L5, NS5ATP9; isoform 2 is encoded by transcript variant 2; *Homo sapiens* KIAA0101 (KIAA0101), transcript variant 2, mRNA. | 1.531 | NM_001029989 | 780 |
| CLOCK | Clock homolog (mouse) | 1.531 | NM_004898 | 781 |
| SEQ_ID_#782 | AGENCOURT_10424058 NIH_MGC_79 *Homo sapiens* cDNA clone IMAGE: 6663644 5', mRNA sequence. | 1.53 | BU929651 | 782 |
| SEQ_ID_#783 | 601488213F1 NIH_MGC_69 *Homo sapiens* cDNA clone IMAGE: 3890762 5', mRNA sequence. | 1.53 | BE876649 | 783 |
| KCTD7 | Potassium channel tetramerisation domain containing 7 | 1.529 | NM_153033 | 784 |
| RANGNRF | RAN guanine nucleotide release factor | 1.528 | NM_016492 | 785 |
| KIAA1505 | KIAA1505 protein | 1.528 | NM_020879 | 786 |
| SEQ_ID_#787 | UI-H-BI4-apu-h-06-0-UI.s1 NCI_CGAP_Sub8 *Homo sapiens* cDNA clone IMAGE: 3088762 3', mRNA sequence. | 1.528 | BF512055 | 787 |
| MARVELD3 | MARVEL domain containing 3 | 1.528 | NM_052858 | 788 |
| MYOC | Myocilin, trabecular meshwork inducible glucocorticoid response | 1.528 | BM712946 | 789 |
| CCND3 | Cyclin D3 | 1.526 | NM_001760 | 790 |
| NAT1 | N-acetyltransferase 1 (arylamine N-acetyltransferase) | 1.524 | NM_000662 | 791 |
| CD97 | CD97 antigen | 1.524 | NM_001025160 | 792 |
| OCIAD2 | OCIA domain containing 2 | 1.522 | NM_001014446 | 793 |
| PKIA | Protein kinase (cAMP-dependent, catalytic) inhibitor alpha | 1.522 | NM_006823 | 794 |

TABLE 1-continued

The EE transcriptome

| Common Name | Description | Fold Change | Genbank Accession number | SEQ ID NO |
|---|---|---|---|---|
| C2 | Complement component 2 | 1.521 | NM_000063 | 795 |
| ACD | Adrenocortical dysplasia homolog (mouse) | 1.521 | NM_022914 | 796 |
| FAM83E | Hypothetical protein FLJ20200 | 1.521 | NM_017708 | 797 |
| S100P | S100 calcium binding protein P | 1.52 | NM_005980 | 798 |
| COX5B | Cytochrome c oxidase subunit Vb | 1.52 | NM_001862 | 799 |
| CCR1 | Chemokine (C-C motif) receptor 1 | 1.52 | NM_001295 | 800 |
| SLC35D2 | Solute carrier family 35, member D2 | 1.518 | NM_007001 | 801 |
| THAP4 | THAP domain containing 4 | 1.518 | NM_015963 | 802 |
| CHEK1 | CHK1 checkpoint homolog (*S. pombe*) | 1.517 | NM_001274 | 803 |
| ZNF326 | Zinc finger protein 326 | 1.516 | NM_181781 | 804 |
| HDHD1A | Haloacid dehalogenase-like hydrolase domain containing 1A | 1.515 | NM_012080 | 805 |
| SEQ_ID_#806 | CDNA FLJ31593 fis, clone NT2RI2002481 | 1.514 | AK056155 | 806 |
| SEQ_ID_#807 | UI-H-CO0-asu-e-10-0-UI.s1 NCI_CGAP_Sub9 *Homo sapiens* cDNA clone IMAGE: 5859954 3', mRNA sequence. | 1.514 | BM988141 | 807 |
| SEQ_ID_#808 | Transcribed locus | 1.513 | BM994952 | 808 |
| WARP | Von Willebrand factor A domain containing 1 | 1.513 | NM_022834 | 809 |
| FLJ22794 | FLJ22794 protein | 1.513 | NM_022074 | 810 |
| STAT2 | Signal transducer and activator of transcription 2, 113 kDa | 1.512 | NM_005419 | 811 |
| SEQ_ID_#812 | *Homo sapiens*, clone IMAGE: 5092955 | 1.512 | BC046188 | 812 |
| ANKRD10 | Ankyrin repeat domain 10 | 1.512 | NM_017664 | 813 |
| SLC25A29 | Solute carrier family 25, member 29 | 1.511 | NM_152333 | 814 |
| SSBP2 | Single-stranded DNA binding protein 2 | 1.51 | BQ027821 | 815 |
| BCL11B | B-cell CLL/lymphoma 11B (zinc finger protein) | 1.509 | NM_022898 | 816 |
| ADAR | Adenosine deaminase, RNA-specific | 1.509 | NM_001025107 | 817 |
| HPCAL1 | Hippocalcin-like 1 | 1.509 | NM_002149 | 818 |
| PDPN | Podoplanin | 1.509 | NM_001006624 | 819 |
| TAL1 | T-cell acute lymphocytic leukemia 1 | 1.508 | NM_003189 | 820 |
| JAK3 | Janus kinase 3 (a protein tyrosine kinase, leukocyte) | 1.508 | NM_000215 | 821 |
| ITPK1 | Inositol 1,3,4-triphosphate 5/6 kinase | 1.508 | NM_014216 | 822 |
| SCYL2 | SCY1-like 2 (*S. cerevisiae*) | 1.507 | NM_017988 | 823 |
| BACE2 | Beta-site APP-cleaving enzyme 2 | 1.507 | NM_012105 | 824 |
| LOC203069 | Hypothetical protein LOC203069 | 1.505 | XM_114618 | 825 |
| LOC116238 | Hypothetical protein BC014072 | 1.504 | NM_138463 | 826 |
| MGC4093 | Hypothetical protein MGC4093 | 1.504 | NM_030578 | 827 |
| MGC17624 | MGC17624 protein | 1.504 | BE872965 | 828 |
| RFX5 | Regulatory factor X, 5 (influences HLA class II expression) | 1.503 | NM_000449 | 829 |
| GBF1 | Golgi-specific brefeldin A resistance factor 1 | 1.503 | NM_004193 | 830 |
| CPA6 | Carboxypeptidase A6 | 1.502 | NM_020361 | 831 |
| UCK2 | Uridine-cytidine kinase 2 | 1.502 | NM_012474 | 832 |
| PDXK | Pyridoxal (pyridoxine, vitamin B6) kinase | 1.501 | NM_003681 | 833 |
| PLSCR3 | Phospholipid scramblase 3 | 1.501 | NM_020360 | 834 |
| SFRS5 | Splicing factor, arginine/serine-rich 5 | 0.666 | NM_006925 | 835 |
| LOC115294 | Similar to hypothetical protein FLJ10883 | 0.665 | NM_052937 | 836 |
| PALLD | Palladin | 0.665 | NM_016081 | 837 |
| EPS8L1 | EPS8-like 1 | 0.665 | NM_017729 | 838 |
| STXBP6 | Syntaxin binding protein 6 (amisyn) | 0.665 | NM_014178 | 839 |
| SEQ_ID_#840 | Full length insert cDNA YI37C01 | 0.665 | BU737911 | 840 |
| ADIPOR1 | Adiponectin receptor 1 | 0.664 | NM_015999 | 841 |
| GNL3 | Guanine nucleotide binding protein-like 3 (nucleolar) | 0.664 | NM_014366 | 842 |
| C6orf69 | Chromosome 6 open reading frame 69 | 0.663 | NM_173562 | 843 |
| C15orf17 | Chromosome 15 open reading frame 17 | 0.663 | NM_020447 | 844 |
| MGLL | Monoglyceride lipase | 0.663 | AW298662 | 845 |
| NCE2 | NEDD8-conjugating enzyme | 0.662 | NM_080678 | 846 |
| PRKCE | Protein kinase C, epsilon | 0.662 | NM_005400 | 847 |
| SLCO4A1 | Solute carrier organic anion transporter family, member 4A1 | 0.662 | BC025345 | 848 |
| TTC9 | Tetratricopeptide repeat domain 9 | 0.661 | XM_027236 | 849 |
| GCSH | Glycine cleavage system protein H (aminomethyl carrier) | 0.661 | NM_004483 | 850 |
| KPNA4 | Karyopherin alpha 4 (importin alpha 3) | 0.661 | NM_002268 | 851 |
| GALNT14 | UDP-N-acetyl-alpha-D-galactosamine: polypeptide N-acetylgalactosaminyltransferase 14 (GalNAc-T14) | 0.66 | NM_024572 | 852 |
| PHF16 | PHD finger protein 16 | 0.659 | NM_014735 | 853 |
| TMEM65 | Hypothetical protein BC017881 | 0.658 | NM_194291 | 854 |

TABLE 1-continued

The EE transcriptome

| Common Name | Description | Fold Change | Genbank Accession number | SEQ ID NO |
|---|---|---|---|---|
| SRPK1 | SFRS protein kinase 1 | 0.656 | NM_003137 | 855 |
| CPNE3 | Copine III | 0.656 | NM_003909 | 856 |
| RPL18A | Ribosomal protein L18a | 0.656 | NM_000980 | 857 |
| ZNF253 | Zinc finger protein 253 | 0.656 | NM_021047 | 858 |
| SPATA5L1 | Spermatogenesis associated 5-like 1 | 0.656 | NM_024063 | 859 |
| SF3B3 | Splicing factor 3b, subunit 3, 130 kDa | 0.655 | NM_012426 | 860 |
| PFN1 | Profilin 1 | 0.655 | NM_005022 | 861 |
| ODZ4 | Odz, odd Oz/ten-m homolog 4 (Drosophila) | 0.654 | XM_166254 | 862 |
| MOSC1 | MOCO sulphurase C-terminal domain containing 1 | 0.653 | NM_022746 | 863 |
| LOC400027 | Hypothetical gene supported by BC047417 | 0.653 | BC047417 | 864 |
| BRAF | V-raf murine sarcoma viral oncogene homolog B1 | 0.653 | NM_004333 | 865 |
| CEBPG | CCAAT/enhancer binding protein (C/EBP), gamma | 0.653 | NM_001806 | 866 |
| JMJD1C | Jumonji domain containing 1C | 0.653 | NM_004241 | 867 |
| MAFF | V-maf musculoaponeurotic fibrosarcoma oncogene homolog F (avian) | 0.653 | NM_012323 | 868 |
| FEM1C | Fem-1 homolog c (C. elegans) | 0.653 | NM_020177 | 869 |
| EP300 | E1A binding protein p300 | 0.652 | BC040700 | 870 |
| ZNF505 | Zinc finger protein 505 | 0.652 | NM_031218 | 871 |
| KIAA1001 | Arylsulfatase G | 0.652 | NM_014960 | 872 |
| SMAP1 | Stromal membrane-associated protein 1 | 0.652 | NM_021940 | 873 |
| C20orf161 | Chromosome 20 open reading frame 161 | 0.652 | NM_033421 | 874 |
| FLJ10726 | Hypothetical protein FLJ10726 | 0.652 | NM_018195 | 875 |
| MGC52423 | Hypothetical protein MGC52423 | 0.652 | NM_182517 | 876 |
| FLJ10156 | Family with sequence similarity 64, member A | 0.651 | NM_019013 | 877 |
| RECQL5 | RecQ protein-like 5 | 0.651 | NM_004259 | 878 |
| DUSP16 | Dual specificity phosphatase 16 | 0.651 | NM_030640 | 879 |
| SLC7A11 | Solute carrier family 7, (cationic amino acid transporter, y+ system) member 11 | 0.651 | NM_014331 | 880 |
| HMGCS1 | 3-hydroxy-3-methylglutaryl-Coenzyme A synthase 1 (soluble) | 0.65 | NM_002130 | 881 |
| PPP2R2C | Protein phosphatase 2 (formerly 2A), regulatory subunit B (PR 52), gamma isoform | 0.65 | NM_020416 | 882 |
| CYB561 | Cytochrome b-561 | 0.649 | NM_001017916 | 883 |
| CDK5R1 | Cyclin-dependent kinase 5, regulatory subunit 1 (p35) | 0.648 | NM_003885 | 884 |
| MRC2 | Mannose receptor, C type 2 | 0.648 | NM_006039 | 885 |
| TUBB6 | Tubulin, beta 6 | 0.648 | NM_032525 | 886 |
| TNFRSF11A | Tumor necrosis factor receptor superfamily, member 11a, NFKB activator | 0.647 | NM_003839 | 887 |
| SEC24C | SEC24 related gene family, member C (S. cerevisiae) | 0.647 | NM_004922 | 888 |
| EIF4EBP2 | Eukaryotic translation initiation factor 4E binding protein 2 | 0.646 | NM_004096 | 889 |
| CPT1A | Carnitine palmitoyltransferase 1A (liver) | 0.646 | NM_001876 | 890 |
| OXSR1 | Oxidative-stress responsive 1 | 0.646 | NM_005109 | 891 |
| NPEPPS | Aminopeptidase puromycin sensitive | 0.646 | NM_006310 | 892 |
| BTBD7 | BTB (POZ) domain containing 7 | 0.645 | NM_018167 | 893 |
| EXTL2 |  | 0.645 | NM_001033025 | 894 |
| LOC401152 | HCV F-transactivated protein 1 | 0.645 | NM_001001701 | 895 |
| MAP4K4 | Mitogen-activated protein kinase kinase kinase kinase 4 | 0.644 | NM_004834 | 896 |
| PCDH21 | Protocadherin 21 | 0.644 | NM_033100 | 897 |
| EYA3 | Eyes absent homolog 3 (Drosophila) | 0.644 | NM_001990 | 898 |
| GRHL1 | Grainyhead-like 1 (Drosophila) | 0.644 | NM_014552 | 899 |
| SORT1 | Sortilin 1 | 0.643 | NM_002959 | 900 |
| SEQ_ID_#901 | 602540462F1 NIH_MGC_59 Homo sapiens cDNA clone IMAGE: 4671519 5', mRNA sequence. | 0.643 | BG495068 | 901 |
| MALL | BENE protein | 0.643 | NM_005434 | 902 |
| WWTR1 | WW domain containing transcription regulator 1 | 0.641 | NM_015472 | 903 |
| MAPK14 | Mitogen-activated protein kinase 14 | 0.641 | NM_001315 | 904 |
| KIAA1128 | KIAA1128 | 0.641 | NM_018999 | 905 |
| SEQ_ID_#906 | Clone IMAGE: 1257951, mRNA sequence | 0.64 | BM664056 | 906 |
| MAP3K9 | Mitogen-activated protein kinase kinase kinase 9 | 0.64 | AK123430 | 907 |
| MLLT4 | Myeloid/lymphoid or mixed-lineage leukemia (trithorax homolog, Drosophila); translocated to, 4 | 0.64 | NM_005936 | 908 |

TABLE 1-continued

The EE transcriptome

| Common Name | Description | Fold Change | Genbank Accession number | SEQ ID NO |
|---|---|---|---|---|
| SEQ_ID_#909 | Similar to ankyrin repeat domain 20A | 0.639 | BC016022 | 909 |
| KIAA0892; MGC75361 | synonym: MGC75361; go_function: binding [goid 0005488] [evidence IEA]; *Homo sapiens* KIAA0892 (KIAA0892), mRNA. | 0.638 | XM_048457 | 910 |
| MFSD1 | Major facilitator superfamily domain containing 1 | 0.638 | NM_022736 | 911 |
| CPEB2 | Cytoplasmic polyadenylation element binding protein 2 | 0.638 | NM_182485 | 912 |
| FOSL2 | FOS-like antigen 2 | 0.638 | NM_005253 | 913 |
| NFIB | Nuclear factor I/B | 0.638 | NM_005596 | 914 |
| SEQ_ID_#915 | 602068385F1 NIH_MGC_58 *Homo sapiens* cDNA clone IMAGE: 4067421 5', mRNA sequence. | 0.638 | BF542107 | 915 |
| CREG1 | Cellular repressor of E1A-stimulated genes 1 | 0.637 | NM_003851 | 916 |
| SEQ_ID_#917 | Clone IMAGE: 110436 mRNA sequence | 0.637 | BU622887 | 917 |
| TMED10 | Transmembrane trafficking protein | 0.637 | NM_006827 | 918 |
| KIAA0182 | KIAA0182 protein | 0.637 | NM_014615 | 919 |
| P53AIP1 | P53-regulated apoptosis-inducing protein 1 | 0.637 | NM_022112 | 920 |
| FTHP1 | Ferritin, heavy polypeptide pseudogene 1 | 0.636 | J04755 | 921 |
| SLC6A15 | Solute carrier family 6, member 15 | 0.635 | NM_182767 | 922 |
| GCKR | Glucokinase (hexokinase 4) regulator | 0.634 | NM_001486 | 923 |
| SAMD9 | Sterile alpha motif domain containing 9 | 0.634 | NM_017654 | 924 |
| C2orf4 | Chromosome 2 open reading frame 4 | 0.634 | NM_015955 | 925 |
| FLJ10826 | | 0.633 | NM_001031707 | 926 |
| FLJ25952 | Zinc finger, DHHC-type containing 20 | 0.633 | NM_153251 | 927 |
| RFFL | Rififylin | 0.633 | NM_001017368 | 928 |
| BAIAP2L1 | BAI1-associated protein 2-like 1 | 0.633 | NM_018842 | 929 |
| LOC286052 | *Homo sapiens* cDNA FLJ37785 fis, clone BRHIP2028330. | 0.632 | AK095104 | 930 |
| ANKRD15 | Ankyrin repeat domain 15 | 0.632 | NM_015158 | 931 |
| KA36 | Type I hair keratin KA36 | 0.632 | NM_182497 | 932 |
| CKAP4 | Cytoskeleton-associated protein 4 | 0.632 | NM_006825 | 933 |
| 13CDNA73 | Hypothetical protein CG003 | 0.632 | NM_023037 | 934 |
| EPS15L1 | Epidermal growth factor receptor pathway substrate 15-like 1 | 0.632 | NM_021235 | 935 |
| CYP2C9 | Cytochrome P450, family 2, subfamily C, polypeptide 9 | 0.632 | NM_000771 | 936 |
| ADAMTS17 | A disintegrin-like and metalloprotease (reprolysin type) with thrombospondin type 1 motif, 17 | 0.631 | AK057529 | 937 |
| SCEL | Sciellin | 0.631 | NM_003843 | 938 |
| PDK1 | Pyruvate dehydrogenase kinase, isoenzyme 1 | 0.631 | NM_002610 | 939 |
| FBXL10 | F-box and leucine-rich repeat protein 10 | 0.631 | NM_001005366 | 940 |
| ZNF539 | Zinc finger protein 254 | 0.631 | NM_203282 | 941 |
| CES1 | Carboxylesterase 1 (monocyte/macrophage serine esterase 1) | 0.631 | NM_016280 | 942 |
| SEQ_ID_#943 | *Homo sapiens* cDNA FLJ36869 fis, clone ASTRO2016819. | 0.631 | AK094188 | 943 |
| HOOK1 | Hook homolog 1 (*Drosophila*) | 0.63 | NM_015888 | 944 |
| CLCN3 | Chloride channel 3 | 0.63 | NM_001829 | 945 |
| SGPL1 | Sphingosine-1-phosphate lyase 1 | 0.63 | NM_003901 | 946 |
| CXCL14 | Chemokine (C-X-C motif) ligand 14 | 0.629 | NM_004887 | 947 |
| SEQ_ID_#948 | CDNA FLJ20486 fis, clone KAT08039 | 0.629 | AK000493 | 948 |
| DIO2 | Deiodinase, iodothyronine, type II | 0.629 | NM_000793 | 949 |
| PRLR | Prolactin receptor | 0.628 | NM_000949 | 950 |
| RANBP9 | RAN binding protein 9 | 0.628 | NM_005493 | 951 |
| TSPAN12 | Tetraspanin 12 | 0.628 | NM_012338 | 952 |
| SEQ_ID_#953 | Transcribed locus, weakly similar to XP_428540.1 PREDICTED: similar to putative 40S ribosomal protein 20S protein, partial [*Gallus gallus*] | 0.627 | BM987621 | 953 |
| LOC286170 | Hypothetical protein LOC286170 | 0.627 | AK055620 | 954 |
| C3orf4 | Chromosome 3 open reading frame 4 | 0.627 | NM_019895 | 955 |
| QSCN6 | Quiescin Q6 | 0.627 | NM_002826 | 956 |
| KCTD6 | Potassium channel tetramerisation domain containing 6 | 0.627 | NM_153331 | 957 |
| MAPT | Microtubule-associated protein tau | 0.626 | NM_005910 | 958 |
| MAP1LC3A | Microtubule-associated protein 1 light chain 3 alpha | 0.625 | NM_032514 | 959 |
| IFRD1 | Interferon-related developmental regulator 1 | 0.625 | NM_001007245 | 960 |

TABLE 1-continued

The EE transcriptome

| Common Name | Description | Fold Change | Genbank Accession number | SEQ ID NO |
|---|---|---|---|---|
| ARHGEF4 | Rho guanine nucleotide exchange factor (GEF) 4 | 0.625 | NM_015320 | 961 |
| TIGA1 | TIGA1 | 0.624 | NM_053000 | 962 |
| ZBTB5 | Zinc finger and BTB domain containing 5 | 0.624 | NM_014872 | 963 |
| C20orf22 | Chromosome 20 open reading frame 22 | 0.624 | NM_015600 | 964 |
| LOC400451 | Hypothetical gene supported by AK075564; BC060873 | 0.623 | NM_207446 | 965 |
| PTPN21 | Protein tyrosine phosphatase, non-receptor type 21 | 0.622 | NM_007039 | 966 |
| SH3BP5 | SH3-domain binding protein 5 (BTK-associated) | 0.622 | NM_001018009 | 967 |
| FLJ32028 | Hypothetical protein FLJ32028 | 0.622 | NM_152680 | 968 |
| ABCC1 | ATP-binding cassette, sub-family C (CFTR/MRP), member 1 | 0.622 | NM_004996 | 969 |
| LOC196264 | Hypothetical protein LOC196264 | 0.621 | NM_198275 | 970 |
| BSPRY | B-box and SPRY domain containing | 0.621 | NM_017688 | 971 |
| PRDM1 | PR domain containing 1, with ZNF domain | 0.621 | NM_001198 | 972 |
| GAS7 | Growth arrest-specific 7 | 0.621 | NM_003644 | 973 |
| TAX1BP1 | Tax1 (human T-cell leukemia virus type I) binding protein 1 | 0.621 | NM_006024 | 974 |
| HIPK3 | Homeodomain interacting protein kinase 3 | 0.621 | NM_005734 | 975 |
| TUBA1 | Tubulin, alpha 1 (testis specific) | 0.621 | NM_006000 | 976 |
| PIGN | Phosphatidylinositol glycan, class N | 0.62 | NM_012327 | 977 |
| SEQ_ID_#978 | CDNA: FLJ22256 fis, clone HRC02860 | 0.62 | AK025909 | 978 |
| SERPINB1 | Serine (or cysteine) proteinase inhibitor, clade B (ovalbumin), member 1 | 0.62 | NM_030666 | 979 |
| BCL2L10 | BCL2-like 10 (apoptosis facilitator) | 0.62 | NM_020396 | 980 |
| PLAGL1 | Pleiomorphic adenoma gene-like 1 | 0.62 | NM_006718 | 981 |
| MAPK13 | Mitogen-activated protein kinase 13 | 0.619 | NM_002754 | 982 |
| PSCA | Prostate stem cell antigen | 0.619 | NM_005672 | 983 |
| DOCK9 | Dedicator of cytokinesis 9 | 0.618 | NM_015296 | 984 |
| M6PRBP1 | Mannose-6-phosphate receptor binding protein 1 | 0.618 | NM_005817 | 985 |
| CCNG2 | Cyclin G2 | 0.617 | NM_004354 | 986 |
| BNC2 | Basonuclin 2 | 0.617 | BX641030 | 987 |
| OSBPL10 | Oxysterol binding protein-like 10 | 0.616 | NM_017784 | 988 |
| SEQ_ID_#989 | CDNA FLJ41623 fis, clone CTONG3009227 | 0.616 | AK123617 | 989 |
| PTK6 | PTK6 protein tyrosine kinase 6 | 0.615 | NM_005975 | 990 |
| MGC13159 | Hypothetical protein MGC13159 | 0.615 | NM_032927 | 991 |
| KNS2 | Kinesin 2 60/70 kDa | 0.615 | NM_005552 | 992 |
| BNIPL | BCL2/adenovirus E1B 19 kD interacting protein like | 0.615 | NM_138278 | 993 |
| OCA2 | Oculocutaneous albinism II (pink-eye dilution homolog, mouse) | 0.614 | NM_000275 | 994 |
| TRPC1 | Transient receptor potential cation channel, subfamily C, member 1 | 0.614 | NM_003304 | 995 |
| TMEM61 | Transmembrane protein 61 | 0.613 | NM_182532 | 996 |
| MAFB | V-maf musculoaponeurotic fibrosarcoma oncogene homolog B (avian) | 0.612 | NM_005461 | 997 |
| MTERFD2 | MTERF domain containing 2 | 0.612 | NM_182501 | 998 |
| FBXL16 | F-box and leucine-rich repeat protein 16 | 0.612 | NM_153350 | 999 |
| TAB3 | TAK1-binding protein 3 | 0.612 | NM_152787 | 1000 |
| FLJ32001 | Chromosome 1 open reading frame 71 | 0.612 | NM_152609 | 1001 |
| SEQ_ID_#1002 | *Homo sapiens*, clone IMAGE: 2960615, mRNA | 0.612 | BC033124 | 1002 |
| SEQ_ID_#1003 | CDNA FLJ41489 fis, clone BRTHA2004582 | 0.611 | AK123483 | 1003 |
| SEQ_ID_#1004 | Similar to RIKEN cDNA 9930021J17 | 0.611 | XM_373035 | 1004 |
| SEQ_ID_#1005 | Full-length cDNA clone CS0DF012YD09 of Fetal brain of *Homo sapiens* (human) | 0.61 | BX460266 | 1005 |
| ABHD6 | Abhydrolase domain containing 6 | 0.609 | NM_020676 | 1006 |
| SMURF1 | SMAD specific E3 ubiquitin protein ligase 1 | 0.609 | NM_020429 | 1007 |
| SNAPC3 | Small nuclear RNA activating complex, polypeptide 3, 50 kDa | 0.608 | NM_003084 | 1008 |
| AADAT | Aminoadipate aminotransferase | 0.608 | NM_016228 | 1009 |
| VDP | Vesicle docking protein p115 | 0.607 | NM_003715 | 1010 |
| TOB1 | Transducer of ERBB2, 1 | 0.607 | NM_005749 | 1011 |
| TJP1 | Tight junction protein 1 (zona occludens 1) | 0.607 | NM_003257 | 1012 |
| RHOB | Ras homolog gene family, member B | 0.607 | NM_004040 | 1013 |
| C1orf128 | Chromosome 1 open reading frame 128 | 0.606 | NM_020362 | 1014 |
| PLD1 | Phospholipase D1, phosphatidylcholine-specific | 0.606 | NM_002662 | 1015 |
| TUBB3 | Tubulin, beta 3 | 0.605 | NM_006086 | 1016 |
| RALA | V-ral simian leukemia viral oncogene homolog A (ras related) | 0.604 | NM_005402 | 1017 |

TABLE 1-continued

The EE transcriptome

| Common Name | Description | Fold Change | Genbank Accession number | SEQ ID NO |
|---|---|---|---|---|
| GNAI3 | Guanine nucleotide binding protein (G protein), alpha inhibiting activity polypeptide 3 | 0.604 | NM_006496 | 1018 |
| CPNE8 | Copine VIII | 0.603 | NM_153634 | 1019 |
| PPID | Peptidylprolyl isomerase D (cyclophilin D) | 0.603 | NM_005038 | 1020 |
| HIF1A | Hypoxia-inducible factor 1, alpha subunit (basic helix-loop-helix transcription factor) | 0.603 | NM_001530 | 1021 |
| RASAL1 | RAS protein activator like 1 (GAP1 like) | 0.602 | NM_004658 | 1022 |
| RINT-1 | Rad50-interacting protein 1 | 0.602 | NM_021930 | 1023 |
| RHOF | Ras homolog gene family, member F (in filopodia) | 0.602 | NM_019034 | 1024 |
| MAL | Mal, T-cell differentiation protein | 0.601 | NM_002371 | 1025 |
| PTDSR | Phosphatidylserine receptor | 0.601 | NM_015167 | 1026 |
| SC5DL | Sterol-C5-desaturase (ERG3 delta-5-desaturase homolog, fungal)-like | 0.6 | NM_001024956 | 1027 |
| ANKRD6 | Ankyrin repeat domain 6 | 0.6 | NM_014942 | 1028 |
| UCHL5 | Ubiquitin carboxyl-terminal hydrolase L5 | 0.6 | NM_015984 | 1029 |
| LOC163590 | Torsin A interacting protein 2 | 0.6 | NM_145034 | 1030 |
| C8orf61 | | 0.6 | NM_001034061 | 1031 |
| FHOD3 | Formin homology 2 domain containing 3 | 0.6 | NM_025135 | 1032 |
| NCOA1 | Nuclear receptor coactivator 1 | 0.599 | NM_003743 | 1033 |
| PLA2G12A | Phospholipase A2, group XIIA | 0.599 | NM_030821 | 1034 |
| ELOVL6 | ELOVL family member 6, elongation of long chain fatty acids (FEN1/Elo2, SUR4/Elo3-like, yeast) | 0.599 | NM_024090 | 1035 |
| RAB2 | RAB2, member RAS oncogene family | 0.599 | NM_002865 | 1036 |
| C17orf39 | Chromosome 17 open reading frame 39 | 0.598 | NM_024052 | 1037 |
| FLJ20582 | Hypothetical protein FLJ20582 | 0.598 | NM_014106 | 1038 |
| AOX1 | Aldehyde oxidase 1 | 0.597 | NM_001159 | 1039 |
| MALT1 | Mucosa associated lymphoid tissue lymphoma translocation gene 1 | 0.596 | NM_006785 | 1040 |
| CSNK1E | Casein kinase 1, epsilon | 0.595 | NM_152221 | 1041 |
| MTPN | Myotrophin | 0.595 | NM_145808 | 1042 |
| SLIC1 | Selectin ligand interactor cytoplasmic-1 | 0.594 | NM_153337 | 1043 |
| C20orf133 | | 0.593 | NM_001033086 | 1044 |
| EMP1 | Epithelial membrane protein 1 | 0.593 | NM_001423 | 1045 |
| C1orf58 | Chromosome 1 open reading frame 58 | 0.593 | NM_144695 | 1046 |
| BCOR | BCL6 co-repressor | 0.593 | NM_017745 | 1047 |
| CA12 | Carbonic anhydrase XII | 0.592 | AK022350 | 1048 |
| C10orf12 | Chromosome 10 open reading frame 12 | 0.592 | NM_015652 | 1049 |
| ACOX2 | Acyl-Coenzyme A oxidase 2, branched chain | 0.592 | NM_003500 | 1050 |
| C20orf111 | Chromosome 20 open reading frame 111 | 0.591 | NM_016470 | 1051 |
| RNF11 | Ring finger protein 11 | 0.591 | NM_014372 | 1052 |
| SEQ_ID_#1055 | CDNA FLJ39000 fis, clone NT2RI2022468 | 0.591 | BX538337 | 1053 |
| PAQR5 | Progestin and adipoQ receptor family member V | 0.591 | NM_017705 | 1054 |
| LATS2 | LATS, large tumor suppressor, homolog 2 (Drosophila) | 0.59 | NM_014572 | 1055 |
| FABP5 | Fatty acid binding protein 5 (psoriasis-associated) | 0.59 | NM_001444 | 1056 |
| FALZ | Fetal Alzheimer antigen | 0.589 | NM_182641 | 1057 |
| SEQ_ID_#1058 | CDNA clone IMAGE: 4800262 | 0.589 | BC040182 | 1058 |
| PIM1 | Pim-1 oncogene | 0.589 | NM_002648 | 1059 |
| SEQ_ID_#1060 | MRNA; cDNA DKFZp564O0862 (from clone DKFZp564O0862) | 0.589 | AL080095 | 1060 |
| SYNE2 | Spectrin repeat containing, nuclear envelope 2 | 0.589 | NM_015180 | 1061 |
| COL4A3BP | Collagen, type IV, alpha 3 (Goodpasture antigen) binding protein | 0.589 | NM_005713 | 1062 |
| ACADL | Acyl-Coenzyme A dehydrogenase, long chain | 0.588 | NM_001608 | 1063 |
| LOC286297; bA251O17.4 | Hypothetical protein LOC286297 | 0.588 | AK097152 | 1064 |
| SEQ_ID_#1065 | | 0.588 | NM_032835 | 1065 |
| TM4SF13 | Tetraspanin 13 | 0.588 | NM_014399 | 1066 |
| NSE1 | NSE1 | 0.588 | NM_145175 | 1067 |
| KIF1B | Kinesin family member 1B | 0.587 | NM_015074 | 1068 |
| SEQ_ID_#1069 | | 0.587 | BC036262 | 1069 |
| RAP1GDS1 | RAP1, GTP-GDP dissociation stimulator 1 | 0.587 | NM_021159 | 1070 |
| SMCX | Smcy homolog, X-linked (mouse) | 0.587 | NM_004187 | 1071 |
| KIAA1991 | Hypothetical protein KIAA1991 | 0.586 | XM_495886 | 1072 |
| TYRO3 | TYRO3 protein tyrosine kinase | 0.586 | NM_006293 | 1073 |
| NFE2L2 | Nuclear factor (erythroid-derived 2)-like 2 | 0.586 | NM_006164 | 1074 |

TABLE 1-continued

The EE transcriptome

| Common Name | Description | Fold Change | Genbank Accession number | SEQ ID NO |
|---|---|---|---|---|
| SEQ_ID_#1075 | 603615533F1 NIH_MGC_110 *Homo sapiens* cDNA clone IMAGE: 5421225 5', mRNA sequence. | 0.586 | BM006561 | 1075 |
| GALNT12 | UDP-N-acetyl-alpha-D-galactosamine: polypeptide N-acetylgalactosaminyltransferase 12 (GalNAc-T12) | 0.586 | NM_024642 | 1076 |
| CHP | Calcium binding protein P22 | 0.586 | NM_007236 | 1077 |
| SESN2 | Sestrin 2 | 0.586 | NM_031459 | 1078 |
| MGC9913 | Hypothetical protein MGC9913 | 0.585 | XM_378178 | 1079 |
| HTR3B | 5-hydroxytryptamine (serotonin) receptor 3B | 0.585 | NM_006028 | 1080 |
| ACOT11 | Thioesterase, adipose associated | 0.585 | NM_147161 | 1081 |
| LOC221362 | Hypothetical protein LOC221362 | 0.584 | AK091117 | 1082 |
| SEC14L1 | SEC14-like 1 (*S. cerevisiae*) | 0.584 | NM_003003 | 1083 |
| MYOZ1 | Myozenin 1 | 0.584 | NM_021245 | 1084 |
| FBXW11 | F-box and WD-40 domain protein 11 | 0.584 | NM_012300 | 1085 |
| CHMP2B | Chromatin modifying protein 2B | 0.584 | NM_014043 | 1086 |
| CRYL1 | Crystallin, lambda 1 | 0.583 | NM_015974 | 1087 |
| FLJ10178 | Hypothetical protein FLJ10178 | 0.583 | NM_018015 | 1088 |
| LOC126295 | Hypothetical protein LOC126295 | 0.583 | NM_173480 | 1089 |
| LGMN | Legumain | 0.583 | NM_001008530 | 1090 |
| MCFD2 | Multiple coagulation factor deficiency 2 | 0.583 | NM_139279 | 1091 |
| GRK4 | G protein-coupled receptor kinase 4 | 0.582 | L34408 | 1092 |
| PGM1 | Phosphoglucomutase 1 | 0.581 | NM_002633 | 1093 |
| FER | Fer (fps/fes related) tyrosine kinase (phosphoprotein NCP94) | 0.581 | NM_005246 | 1094 |
| ZDHHC21 | Zinc finger, DHHC-type containing 21 | 0.581 | NM_178566 | 1095 |
| DOCK3 | Dedicator of cytokinesis 3 | 0.58 | NM_004947 | 1096 |
| PI4KII | Phosphatidylinositol 4-kinase type II | 0.58 | NM_018425 | 1097 |
| RUSC2 | RUN and SH3 domain containing 2 | 0.58 | NM_014806 | 1098 |
| SEQ_ID_#1099 | CDNA FLJ35001 fis, clone OCBBF2011887 | 0.579 | AK123847 | 1099 |
| WDFY3 | WD repeat and FYVE domain containing 3 | 0.578 | NM_014991 | 1100 |
| TRERF1 | Transcriptional regulating factor 1 | 0.578 | NM_033502 | 1101 |
| NAGK | N-acetylglucosamine kinase | 0.578 | NM_017567 | 1102 |
| RBM25; S164; RNPC7 | *Homo sapiens* mRNA; cDNA DKFZp667O2119 (from clone DKFZp667O2119). | 0.578 | AL832314 | 1103 |
| FAM62B | Family with sequence similarity 62 (C2 domain containing) member B | 0.577 | NM_020728 | 1104 |
| ANKH | Ankylosis, progressive homolog (mouse) | 0.577 | NM_054027 | 1105 |
| SEQ_ID_#1106 | | 0.576 | XM_379938 | 1106 |
| SLC13A4 | Solute carrier family 13 (sodium/sulfate symporters), member 4 | 0.576 | NM_012450 | 1107 |
| CDS1 | CDP-diacylglycerol synthase (phosphatidate cytidylyltransferase) 1 | 0.576 | NM_001263 | 1108 |
| KDELR3 | KDEL (Lys-Asp-Glu-Leu) endoplasmic reticulum protein retention receptor 3 | 0.576 | NM_006855 | 1109 |
| HIPK2 | synonym: PRO0593; homeodomain-interacting protein kinase 2; go_component: cytoplasm [goid 0005737] [evidence ISS]; go_component: nucleus [goid 0005634] [evidence IDA] [pmid 12220523]; go_component: nuclear body [goid 0016604] [evidence TAS] [pmid 14626429]; go_function: ATP binding [goid 0005524] [evidence IEA]; go_function: virion binding [goid 0046790] [evidence IPI] [pmid 14990717]; go_function: protein binding [goid 0005515] [evidence IPI] [pmid 12220523]; go_function: transferase activity [goid 0016740] [evidence IEA]; go_function: transcription corepressor activity [goid 0003714] [evidence TAS] [pmid 9748262]; go_function: protein serine/threonine kinase activity [goid 0004674] [evidence IEA]; go_process: apoptosis [goid 0006915] [evidence IEA]; go_process: transcription [goid 0006350] [evidence IEA]; go_process: virus-host interaction [goid 0019048] [evidence NAS] [pmid 14990717]; go_process: protein amino acid phosphorylation [goid 0006468] [evidence IEA]; go_process: positive regulation of JNK cascade [goid | 0.575 | NM_014075 | 1110 |

TABLE 1-continued

The EE transcriptome

| Common Name | Description | Fold Change | Genbank Accession number | SEQ ID NO |
|---|---|---|---|---|
| | 0046330] [evidence IMP] [pmid 14678985]; go_process: regulation of transcription, DNA-dependent [goid 0006355] [evidence IEA]; go_process: regulation of progression through cell cycle [goid 0000074] [evidence NAS] [pmid 14990717]; go_process: induction of apoptosis by intracellular signals [goid 0008629] [evidence NAS] [pmid 15122315]; go_process: positive regulation of transforming growth factor beta receptor signaling pathway [goid 0030511] [evidence IMP] [pmid 14678985]; *Homo sapiens* homeodomain interacting protein kinase 2 (HIPK2), mRNA. | | | |
| PBEF1 | Pre-B-cell colony enhancing factor 1 | 0.575 | NM_005746 | 1111 |
| ZNF117 | Zinc finger protein 117 (HPF9) | 0.574 | NM_015852 | 1112 |
| CFTR | Cystic fibrosis transmembrane conductance regulator, ATP-binding cassette (sub-family C, member 7) | 0.574 | NM_000492 | 1113 |
| PER3 | Period homolog 3 (*Drosophila*) | 0.573 | NM_016831 | 1114 |
| KRTHA3A | Keratin, hair, acidic, 3A | 0.573 | NM_004138 | 1115 |
| SGEF | Src homology 3 domain-containing guanine nucleotide exchange factor | 0.573 | NM_015595 | 1116 |
| ENSA | Endosulfine alpha | 0.572 | NM_207043 | 1117 |
| WNK4 | WNK lysine deficient protein kinase 4 | 0.572 | NM_032387 | 1118 |
| SLC2A13 | Solute carrier family 2 (facilitated glucose transporter), member 13 | 0.572 | NM_052885 | 1119 |
| ZZANK1 | Mindbomb homolog 2 (*Drosophila*) | 0.572 | NM_080875 | 1120 |
| CYYR1 | Cysteine/tyrosine-rich 1 | 0.572 | NM_052954 | 1121 |
| TRIB3 | Tribbles homolog 3 (*Drosophila*) | 0.571 | NM_021158 | 1122 |
| C1orf108 | Chromosome 1 open reading frame 108 | 0.571 | NM_024595 | 1123 |
| SEQ_ID_#1024 | | 0.571 | AL031723 | 1124 |
| RNF24 | Ring finger protein 24 | 0.571 | NM_007219 | 1125 |
| H2BFS | H2B histone family, member S | 0.571 | NM_017445 | 1126 |
| DKK4 | Dickkopf homolog 4 (*Xenopus laevis*) | 0.569 | NM_014420 | 1127 |
| MXI1 | MAX interactor 1 | 0.569 | NM_001008541 | 1128 |
| CABLES1 | Cdk5 and Abl enzyme substrate 1 | 0.569 | NM_138375 | 1129 |
| HECTD1 | HECT domain containing 1 | 0.568 | NM_015382 | 1130 |
| MAF | | 0.567 | NM_001031804 | 1131 |
| PCGF2 | Polycomb group ring finger 2 | 0.567 | BM695150 | 1132 |
| PLXDC2 | Plexin domain containing 2 | 0.567 | AK127644 | 1133 |
| WDR41 | WD repeat domain 41 | 0.567 | NM_018268 | 1134 |
| TSPYL4 | TSPY-like 4 | 0.566 | NM_021648 | 1135 |
| UPP1 | Uridine phosphorylase 1 | 0.565 | NM_003364 | 1136 |
| TMEM37 | Transmembrane protein 37 | 0.565 | NM_183240 | 1137 |
| FBXW7 | F-box and WD-40 domain protein 7 (archipelago homolog, *Drosophila*) | 0.565 | NM_001013415 | 1138 |
| RPIB9 | Rap2-binding protein 9 | 0.565 | NM_138290 | 1139 |
| SLC1A3 | Solute carrier family 1 (glial high affinity glutamate transporter), member 3 | 0.564 | NM_004172 | 1140 |
| FAM3D | Family with sequence similarity 3, member D | 0.564 | NM_138805 | 1141 |
| TSC22D2 | TSC22 domain family, member 2 | 0.563 | NM_014779 | 1142 |
| DSC1 | Desmocollin 1 | 0.563 | NM_004948 | 1143 |
| SRPX2 | Sushi-repeat-containing protein, X-linked 2 | 0.563 | NM_014467 | 1144 |
| GRB14 | Growth factor receptor-bound protein 14 | 0.563 | NM_004490 | 1145 |
| COBL | Cordon-bleu homolog (mouse) | 0.563 | NM_015198 | 1146 |
| HIST1H2BF | Histone 1, H2bf | 0.563 | NM_003522 | 1147 |
| C10orf57 | Chromosome 10 open reading frame 57 | 0.563 | NM_025125 | 1148 |
| SEQ_ID_#1149 | Transcribed locus | 0.562 | BM993105 | 1149 |
| MELL1 | Mel transforming oncogene-like 1 | 0.562 | NM_033467 | 1150 |
| SHMT1 | Serine hydroxymethyltransferase 1 (soluble) | 0.562 | NM_004169 | 1151 |
| SEQ_ID_#1152 | | 0.562 | NM_032751 | 1152 |
| C14orf78 | Chromosome 14 open reading frame 78 | 0.561 | XM_290629 | 1153 |
| DRCTNNB1A | Down-regulated by Ctnnb1, a | 0.433 | NM_032581 | 1154 |
| SLC24A3 | Solute carrier family 24 (sodium/potassium/calcium exchanger), member 3 | 0.56 | NM_020689 | 1155 |
| RC3H1 | | 0.56 | NM_172071 | 1156 |
| SEQ_ID_#1157 | CDNA: FLJ23573 fis, clone LNG12520 | 0.559 | AK027226 | 1157 |
| SYAP1 | Synapse associated protein 1, SAP47 homolog (*Drosophila*) | 0.559 | NM_032796 | 1158 |

TABLE 1-continued

The EE transcriptome

| Common Name | Description | Fold Change | Genbank Accession number | SEQ ID NO |
|---|---|---|---|---|
| D4S234E | DNA segment on chromosome 4 (unique) 234 expressed sequence | 0.559 | NM_014392 | 1159 |
| SEQ_ID_#1160 | 602540462F1 NIH_MGC_59 *Homo sapiens* cDNA clone IMAGE: 4671519 5', mRNA sequence. | 0.559 | BG495068 | 1160 |
| B3GNT5 | UDP-GlcNAc: betaGal beta-1,3-N-acetylglucosaminyltransferase 5 | 0.559 | NM_032047 | 1161 |
| SCGB2A1 | Secretoglobin, family 2A, member 1 | 0.558 | NM_002407 | 1162 |
| ZNF416 | Zinc finger protein 416 | 0.558 | NM_017879 | 1163 |
| LOC146174 | Chromosome 16 open reading frame 52 | 0.557 | NM_173501 | 1164 |
| TPM4 | Tropomyosin 4 | 0.556 | NM_003290 | 1165 |
| KRTHA2 | Keratin, hair, acidic, 2 | 0.556 | NM_002278 | 1166 |
| CPVL | Carboxypeptidase, vitellogenic-like | 0.555 | NM_019029 | 1167 |
| GADD45B | Growth arrest and DNA-damage-inducible, beta | 0.555 | NM_015675 | 1168 |
| SEQ_ID_#1169 | BX109361 NCI_CGAP_Lu5 *Homo sapiens* cDNA clone IMAGp998B174679; IMAGE: 1908400, mRNA sequence. | 0.554 | BX109361 | 1169 |
| SLC5A1 | Solute carrier family 5 (sodium/glucose cotransporter), member 1 | 0.554 | NM_000343 | 1170 |
| HNMT | Histamine N-methyltransferase | 0.554 | NM_001024074 | 1171 |
| SEQ_ID_#1172 | CDNA FLJ31407 fis, clone NT2NE2000137 | 0.554 | AK055969 | 1172 |
| SNX24 | Sorting nexing 24 | 0.554 | NM_014035 | 1173 |
| CPD | Carboxypeptidase D | 0.553 | NM_001304 | 1174 |
| SEQ_ID_#1175 | Transcribed locus | 0.553 | BX116062 | 1175 |
| LOC162993 | Hypothetical protein LOC162993 | 0.553 | XM_091914 | 1176 |
| CUL4B | Cullin 4B | 0.552 | NM_003588 | 1177 |
| H41 | Hypothetical protein H41 | 0.551 | NM_017548 | 1178 |
| SEQ_ID_#1179 | CDNA clone IMAGE: 4830452 | 0.551 | BC034636 | 1179 |
| SNX14 | Sorting nexin 14 | 0.551 | NM_153816 | 1180 |
| ZNRF1 | Zinc and ring finger 1 | 0.551 | NM_032268 | 1181 |
| AHCY | S-adenosylhomocysteine hydrolase | 0.551 | NM_000687 | 1182 |
| SEQ_ID_#1183 | Transcribed locus, strongly similar to XP_517083.1 PREDICTED: similar to hypothetical protein MGC13159 [*Pan troglodytes*] | 0.551 | BF510602 | 1183 |
| CSTB | Cystatin B (stefin B) | 0.551 | NM_000100 | 1184 |
| RASAL2 | RAS protein activator like 2 | 0.549 | NM_004841 | 1185 |
| ITPR2 | Inositol 1,4,5-triphosphate receptor, type 2 | 0.548 | NM_002223 | 1186 |
| CORO1C | Coronin, actin binding protein, 1C | 0.547 | NM_014325 | 1187 |
| IL22RA1 | Interleukin 22 receptor, alpha 1 | 0.546 | NM_021258 | 1188 |
| IMPA2 | Inositol(myo)-1(or 4)-monophosphatase 2 | 0.545 | NM_014214 | 1189 |
| PTN | Pleiotrophin (heparin binding growth factor 8, neurite growth-promoting factor 1) | 0.545 | NM_002825 | 1190 |
| SEQ_ID_#1191 | Transcribed locus | 0.545 | BX327653 | 1191 |
| PBX3 | Pre-B-cell leukemia transcription factor 3 | 0.545 | NM_006195 | 1192 |
| ST7L | Suppression of tumorigenicity 7 like | 0.544 | AK128799 | 1193 |
| FLJ20674 | Hypothetical protein FLJ20674 | 0.544 | NM_019086 | 1194 |
| JARID1B | Jumonji, AT rich interactive domain 1B (RBP2-like) | 0.543 | NM_006618 | 1195 |
| UNC13B | Unc-13 homolog B (*C. elegans*) | 0.543 | NM_006377 | 1196 |
| SEC24A | SEC24 related gene family, member A (*S. cerevisiae*) | 0.542 | XM_094581 | 1197 |
| MXD1 | MAX dimerization protein 1 | 0.541 | NM_002357 | 1198 |
| ROR1 | Receptor tyrosine kinase-like orphan receptor 1 | 0.541 | NM_005012 | 1199 |
| SLC22A15 | Solute carrier family 22 (organic cation transporter), member 15 | 0.54 | NM_018420 | 1200 |
| GDPD3 | | 0.54 | NM_001031718 | 1201 |
| LOC285671 | Ring finger protein 180 | 0.539 | NM_178532 | 1202 |
| COL21A1 | Collagen, type XXI, alpha 1 | 0.538 | NM_030820 | 1203 |
| SEQ_ID_#1204 | 602540462F1 NIH_MGC_59 *Homo sapiens* cDNA clone IMAGE: 4671519 5', mRNA sequence. | 0.538 | BG495068 | 1204 |
| EHBP1 | EH domain binding protein 1 | 0.537 | NM_015252 | 1205 |
| FTH1 | Ferritin, heavy polypeptide 1 | 0.537 | NM_002032 | 1206 |
| LOC159090 | Similar to hypothetical protein MGC17347 | 0.537 | NM_145284 | 1207 |
| COQ6 | synonym: CGI-10; isoform a is encoded by transcript variant 1; go_function: FAD binding [goid 0050660] [evidence IEA]; go_function: monooxygenase activity [goid 0004497] [evidence IEA]; go_function: ubiquinone biosynthesis monooxygenase activity [goid 0015997] [evidence IEA]; go_process: metabolism [goid 0008152] [evidence IEA]; | 0.537 | NM_015940 | 1208 |

TABLE 1-continued

The EE transcriptome

| Common Name | Description | Fold Change | Genbank Accession number | SEQ ID NO |
|---|---|---|---|---|
| | go_process: electron transport [goid 0006118] [evidence IEA]; go_process: ubiquinone biosynthesis [goid 0006744] [evidence IEA]; go_process: aromatic compound metabolism [goid 0006725] [evidence IEA]; Homo sapiens coenzyme Q6 homolog (yeast) (COQ6), transcript variant 1, mRNA. | | | |
| SEQ_ID_#1209 | UI-CF-DU1-adq-o-11-0-UI.s1 UI-CF-DU1 Homo sapiens cDNA clone UI-CF-DU1-adq-o-11-0-UI 3', mRNA sequence. | 0.537 | BM978616 | 1209 |
| SFT2D2 | SFT2 domain containing 2 | 0.536 | NM_199344 | 1210 |
| DEGS2 | Degenerative spermatocyte homolog 2, lipid desaturase (Drosophila) | 0.536 | BE512716 | 1211 |
| ERO1L | ERO1-like (S. cerevisiae) | 0.536 | NM_014584 | 1212 |
| FLJ32421 | Chromosome 1 open reading frame 58 | 0.535 | NM_144695 | 1213 |
| MTHFD2L | Methylenetetrahydrofolate dehydrogenase (NADP+ dependent) 2-like | 0.534 | NM_001004346 | 1214 |
| PHC1 | Polyhomeotic-like 1 (Drosophila) | 0.533 | NM_004426 | 1215 |
| IL13RA1 | Interleukin 13 receptor, alpha 1 | 0.533 | NM_001560 | 1216 |
| MINA | MYC induced nuclear antigen | 0.533 | NM_032778 | 1217 |
| UBE2H | Ubiquitin-conjugating enzyme E2H (UBC8 homolog, yeast) | 0.533 | NM_003344 | 1218 |
| SEQ_ID_#1219 | Homo sapiens, clone IMAGE: 4413555, mRNA | 0.532 | BG034859 | 1219 |
| C14orf45 | Chromosome 14 open reading frame 45 | 0.532 | NM_025057 | 1220 |
| ABTB2 | Ankyrin repeat and BTB (POZ) domain containing 2 | 0.532 | NM_145804 | 1221 |
| SLC35F2 | Solute carrier family 35, member F2 | 0.532 | NM_017515 | 1222 |
| GMPPB | GDP-mannose pyrophosphorylase B | 0.531 | NM_013334 | 1223 |
| INADL | InaD-like (Drosophila) | 0.531 | NM_170605 | 1224 |
| ANKRD46 | Ankyrin repeat domain 46 | 0.531 | NM_198401 | 1225 |
| WDR26 | WD repeat domain 26 | 0.531 | NM_025160 | 1226 |
| ZYG11A | Zyg-11 homolog A (C. elegans) | 0.53 | NM_001004339 | 1227 |
| ELL2 | Elongation factor, RNA polymerase II, 2 | 0.53 | NM_012081 | 1228 |
| ARRDC3 | Arrestin domain containing 3 | 0.53 | NM_020801 | 1229 |
| MBD2 | Apoptosis-inducing factor (AIF)-like mitochondrion-associated inducer of death | 0.529 | NM_032797 | 1230 |
| VARSL | Valyl-tRNA synthetase 2-like | 0.529 | NM_020442 | 1231 |
| UBE2E2 | Ubiquitin-conjugating enzyme E2E 2 (UBC 4/5 homolog, yeast) | 0.529 | NM_152653 | 1232 |
| C1orf168 | Chromosome 1 open reading frame 168 | 0.529 | NM_001004303 | 1233 |
| TFCP2L1 | Transcription factor CP2-like 1 | 0.528 | NM_014553 | 1234 |
| LOC284825 | Hypothetical protein LOC284825 | 0.528 | AI311303 | 1235 |
| CAPN5 | Calpain 5 | 0.528 | NM_004055 | 1236 |
| VIT | Vitrin | 0.528 | NM_053276 | 1237 |
| SEQ_ID_#1238 | | 0.528 | NM_032746 | 1238 |
| DKFZp434C0328 | Hypothetical protein DKFZp434C0328 | 0.528 | NM_017577 | 1239 |
| PLEKHG1 | synonyms: FLJ31738, KIAA1209; Homo sapiens pleckstrin homology domain containing, family G (with RhoGef domain) member 1 (PLEKHG1), mRNA. | 0.527 | NM_001029884 | 1240 |
| CD207 | CD207 antigen, langerin | 0.526 | NM_015717 | 1241 |
| NOV | Nephroblastoma overexpressed gene | 0.526 | NM_002514 | 1242 |
| LRFN5 | Leucine rich repeat and fibronectin type III domain containing 5 | 0.526 | NM_152447 | 1243 |
| 7-Mar | Membrane-associated ring finger (C3HC4) 7 | 0.525 | NM_022826 | 1244 |
| RAB6B | RAB6B, member RAS oncogene family | 0.524 | NM_016577 | 1245 |
| MYEOV | Myeloma overexpressed gene (in a subset of t(11; 14) positive multiple myelomas) | 0.524 | NM_138768 | 1246 |
| MDFIC | MyoD family inhibitor domain containing | 0.524 | NM_199072 | 1247 |
| SLC38A2 | Solute carrier family 38, member 2 | 0.524 | NM_018976 | 1248 |
| SEQ_ID_#1249 | Transcribed locus | 0.523 | BM712901 | 1249 |
| MRPS10 | Mitochondrial ribosomal protein S10 | 0.523 | NM_018141 | 1250 |
| FLJ13910 | Hypothetical protein FLJ13910 | 0.523 | NM_022780 | 1251 |
| ZNF92 | Zinc finger protein 92 (HTF12) | 0.521 | NM_007139 | 1252 |
| SEQ_ID_#1253 | CDNA FLJ30885 fis, clone FEBRA2004987 | 0.52 | AK055447 | 1253 |
| ST6GALNAC1 | ST6 (alpha-N-acetyl-neuraminyl-2,3-beta-galactosyl-1,3)-N-acetylgalactosaminide alpha-2,6-sialyltransferase 1 | 0.52 | NM_018414 | 1254 |
| DSC2 | Desmocollin 2 | 0.518 | NM_004949 | 1255 |
| PNMA1 | Paraneoplastic antigen MA1 | 0.518 | NM_006029 | 1256 |
| MGC40368 | Hypothetical protein MGC40368 | 0.517 | NM_152772 | 1257 |
| PDLIM5 | PDZ and LIM domain 5 | 0.516 | NM_001011515 | 1258 |

TABLE 1-continued

The EE transcriptome

| Common Name | Description | Fold Change | Genbank Accession number | SEQ ID NO |
|---|---|---|---|---|
| SH3D19 | SH3 domain protein D19 | 0.516 | NM_001009555 | 1259 |
| C1orf181 | Hypothetical protein FLJ20729 | 0.515 | NM_017953 | 1260 |
| LTB4DH | Leukotriene B4 12-hydroxydehydrogenase | 0.515 | NM_012212 | 1261 |
| WDR5B | WD repeat domain 5B | 0.514 | NM_019069 | 1262 |
| TSCOT | Thymic stromal co-transporter | 0.514 | NM_033051 | 1263 |
| C1orf21 | Chromosome 1 open reading frame 21 | 0.514 | NM_030806 | 1264 |
| SLC27A6 | Solute carrier family 27 (fatty acid transporter), member 6 | 0.513 | NM_001017372 | 1265 |
| FLJ25179 | C3 and PZP-like, alpha-2-macroglobulin domain containing 9 | 0.513 | NM_144670 | 1266 |
| EGLN1 | Egl nine homolog 1 (*C. elegans*) | 0.512 | NM_022051 | 1267 |
| PHTF2 | Putative homeodomain transcription factor 2 | 0.511 | NM_020432 | 1268 |
| GP1BB | Glycoprotein Ib (platelet), beta polypeptide | 0.511 | NM_000407 | 1269 |
| BCAR3 | Breast cancer anti-estrogen resistance 3 | 0.51 | NM_003567 | 1270 |
| LNX2 | Ligand of numb-protein X 2 | 0.508 | NM_153371 | 1271 |
| RPL23AP7; RPL23AL1; bA395L14.9 | *Homo sapiens* cDNA FLJ30702 fis, clone FCBBF2001001. | 0.507 | AK055264 | 1272 |
| CLEC3B | C-type lectin domain family 3, member B | 0.507 | NM_003278 | 1273 |
| C18orf9 | Chromosome 18 open reading frame 9 | 0.507 | NM_024899 | 1274 |
| CRTAC1 | Cartilage acidic protein 1 | 0.507 | NM_018058 | 1275 |
| C18orf19 | Chromosome 18 open reading frame 19 | 0.506 | NM_152352 | 1276 |
| CNFN | Cornifelin | 0.506 | NM_032488 | 1277 |
| HIST2H2BE | Histone 2, H2be | 0.506 | NM_003528 | 1278 |
| WASL | Wiskott-Aldrich syndrome-like | 0.506 | NM_003941 | 1279 |
| FLRT2 | Fibronectin leucine rich transmembrane protein 2 | 0.505 | NM_013231 | 1280 |
| SASH1 | SAM and SH3 domain containing 1 | 0.505 | NM_015278 | 1281 |
| GPSM2 | G-protein signalling modulator 2 (AGS3-like, *C. elegans*) | 0.504 | NM_013296 | 1282 |
| PLK2 | Polo-like kinase 2 (*Drosophila*) | 0.504 | NM_006622 | 1283 |
| SPRR3 | Small proline-rich protein 3 | 0.504 | NM_005416 | 1284 |
| CAST | Calpastatin | 0.503 | NM_001750 | 1285 |
| RNMT | RNA (guanine-7-) methyltransferase | 0.503 | NM_003799 | 1286 |
| K5B | Keratin 5b | 0.503 | NM_173352 | 1287 |
| TM4SF12 | Tetraspanin 12 | 0.503 | NM_012338 | 1288 |
| RRAGD | Ras-related GTP binding D | 0.503 | NM_021244 | 1289 |
| MT1F | Metallothionein 1F (functional) | 0.503 | NM_005949 | 1290 |
| RBM35A | | 0.502 | NM_001034915 | 1291 |
| LYNX1 | Ly6/neurotoxin 1 | 0.501 | NM_023946 | 1292 |
| HK2 | Hexokinase 2 | 0.5 | NM_000189 | 1293 |
| C8orf48 | Hypothetical protein FLJ25402 | 0.5 | NM_001007090 | 1294 |
| MOSPD1 | Motile sperm domain containing 1 | 0.5 | NM_019556 | 1295 |
| PMAIP1 | Phorbol-12-myristate-13-acetate-induced protein 1 | 0.499 | NM_021127 | 1296 |
| TRPS1 | Trichorhinophalangeal syndrome I | 0.499 | NM_014112 | 1297 |
| FLJ14054 | Hypothetical protein FLJ14054 | 0.499 | NM_024563 | 1298 |
| SLITL2 | Slit-like 2 (*Drosophila*) | 0.498 | NM_138440 | 1299 |
| CTTNBP2 | Cortactin binding protein 2 | 0.498 | NM_033427 | 1300 |
| UBE2G1 | Ubiquitin-conjugating enzyme E2G 1 (UBC7 homolog, *C. elegans*) | 0.497 | NM_003342 | 1301 |
| SEQ_ID_#1302 | UI-E-EJ1-ajs-c-01-0-UI.r1 UI-E-EJ1 *Homo sapiens* cDNA clone UI-E-EJ1-ajs-c-01-0-UI 5', mRNA sequence. | 0.497 | BQ185835 | 1302 |
| CDKN2B | Cyclin-dependent kinase inhibitor 2B (p15, inhibits CDK4) | 0.496 | NM_004936 | 1303 |
| KIAA0232 | KIAA0232 gene product | 0.496 | NM_014743 | 1304 |
| LRRC20 | Leucine rich repeat containing 20 | 0.495 | NM_018205 | 1305 |
| SOCS6 | Suppressor of cytokine signaling 6 | 0.495 | NM_004232 | 1306 |
| KLK13 | Kallikrein 13 | 0.495 | NM_015596 | 1307 |
| ZDHHC15 | Zinc finger, DHHC-type containing 15 | 0.494 | NM_144969 | 1308 |
| UNC84A | Unc-84 homolog A (*C. elegans*) | 0.494 | NM_025154 | 1309 |
| LOC147645 | Hypothetical protein LOC147645 | 0.494 | XM_085831 | 1310 |
| FLJ14011 | Zinc finger protein 667 | 0.494 | NM_022103 | 1311 |
| HIST1H3D | Histone 1, H3d | 0.493 | NM_003530 | 1312 |
| TIMP2 | Tissue inhibitor of metalloproteinase 2 | 0.492 | NM_003255 | 1313 |
| ETNK2 | Ethanolamine kinase 2 | 0.492 | NM_018208 | 1314 |
| SLC6A1 | Solute carrier family 6 (neurotransmitter transporter, GABA), member 1 | 0.492 | NM_003042 | 1315 |
| MARCKS | Myristoylated alanine-rich protein kinase C substrate | 0.491 | NM_002356 | 1316 |
| MRCL3 | Myosin regulatory light chain MRCL3 | 0.489 | NM_006471 | 1317 |
| Gcom1 | GRINL1A combined protein | 0.488 | NM_001018100 | 1318 |
| C21orf5 | Chromosome 21 open reading frame 5 | 0.488 | NM_005128 | 1319 |

TABLE 1-continued

The EE transcriptome

| Common Name | Description | Fold Change | Genbank Accession number | SEQ ID NO |
|---|---|---|---|---|
| FUT11 | Fucosyltransferase 11 (alpha (1,3) fucosyltransferase) | 0.486 | NM_173540 | 1320 |
| CYP2C18 | Cytochrome P450, family 2, subfamily C, polypeptide 18 | 0.486 | NM_000772 | 1321 |
| CTH | Cystathionase (cystathionine gamma-lyase) | 0.485 | NM_001902 | 1322 |
| CYP2C9 | Cytochrome P450, family 2, subfamily C, polypeptide 9 | 0.485 | NM_000771 | 1323 |
| FLJ11151 | Hypothetical protein FLJ11151 | 0.484 | NM_018340 | 1324 |
| LOC387758 | Similar to RIKEN cDNA 1110018M03 | 0.482 | NM_203371 | 1325 |
| KIAA1345 | KIAA1345 protein | 0.481 | XM_106386 | 1326 |
| GNG12 | Guanine nucleotide binding protein (G protein), gamma 12 | 0.48 | NM_018841 | 1327 |
| SHRM | Shroom | 0.48 | NM_020859 | 1328 |
| SEQ_ID_#1329 | Transcribed locus | 0.48 | BG191459 | 1329 |
| PHACTR2 | Phosphatase and actin regulator 2 | 0.48 | NM_014721 | 1330 |
| USP13 | Ubiquitin specific protease 13 (isopeptidase T-3) | 0.479 | NM_003940 | 1331 |
| CIDEA | Cell death-inducing DFFA-like effector a | 0.479 | NM_001279 | 1332 |
| ETV1 | Ets variant gene 1 | 0.478 | NM_004956 | 1333 |
| MAP3K4 | Mitogen-activated protein kinase kinase kinase 4 | 0.476 | NM_005922 | 1334 |
| HIC | MyoD family inhibitor domain containing | 0.476 | NM_199072 | 1335 |
| LOC96610 | Hypothetical protein similar to KIAA0187 gene product | 0.476 | NM_080926 | 1336 |
| DEGS1 | Degenerative spermatocyte homolog 1, lipid desaturase (Drosophila) | 0.475 | NM_003676 | 1337 |
| SEQ_ID_#1338 | CDNA: FLJ22256 fis, clone HRC02860 | 0.474 | AK025909 | 1338 |
| HPSE | Heparanase | 0.473 | NM_006665 | 1339 |
| KCNAB1 | Potassium voltage-gated channel, shaker-related subfamily, beta member 1 | 0.473 | NM_003471 | 1340 |
| BNIP3L | BCL2/adenovirus E1B 19 kDa interacting protein 3-like | 0.473 | NM_004331 | 1341 |
| NPR3 | Natriuretic peptide receptor C/guanylate cyclase C (atrionatriuretic peptide receptor C) | 0.473 | NM_000908 | 1342 |
| LOC388727 | Hypothetical LOC388727 | 0.471 | XM_373881 | 1343 |
| CYP26B1 | Cytochrome P450, family 26, subfamily B, polypeptide 1 | 0.471 | NM_019885 | 1344 |
| SLC38A4 | Solute carrier family 38, member 4 | 0.47 | NM_018018 | 1345 |
| LNX1 | Ligand of numb-protein X | 0.47 | NM_032622 | 1346 |
| CFLAR | CASP8 and FADD-like apoptosis regulator | 0.469 | NM_003879 | 1347 |
| MT1X | Metallothionein 1X | 0.468 | NM_005952 | 1348 |
| PELI1 | Pellino homolog 1 (Drosophila) | 0.468 | NM_020651 | 1349 |
| CNKSR3 | CNKSR family member 3 | 0.468 | NM_173515 | 1350 |
| SEQ_ID_#1351 | AGENCOURT_7760686 NIH_MGC_92 Homo sapiens cDNA clone IMAGE: 6016357 5', mRNA sequence. | 0.468 | BQ421887 | 1351 |
| ITM2A | Integral membrane protein 2A | 0.467 | NM_004867 | 1352 |
| DGAT2 | Diacylglycerol O-acyltransferase homolog 2 (mouse) | 0.467 | NM_032564 | 1353 |
| DKFZp434N2030 | Hypothetical protein DKFZp434N2030 | 0.466 | NM_001009894 | 1354 |
| WASF3 | WAS protein family, member 3 | 0.466 | NM_006646 | 1355 |
| LOC400960 | Hypothetical gene supported by BC040598 | 0.466 | AK056822 | 1356 |
| TTC22 | Hypothetical protein FLJ20619 | 0.465 | NM_017904 | 1357 |
| CHI3L1 | Chitinase 3-like 1 (cartilage glycoprotein-39) | 0.465 | NM_001276 | 1358 |
| RBP7 | Retinol binding protein 7, cellular | 0.464 | NM_052960 | 1359 |
| EGFL5 | EGF-like-domain, multiple 5 | 0.464 | XM_376905 | 1360 |
| PHLDA1 | Pleckstrin homology-like domain, family A, member 1 | 0.464 | NM_007350 | 1361 |
| CRIP2 | Cysteine-rich protein 2 | 0.464 | NM_001312 | 1362 |
| MYBBP1A | MYB binding protein (P160) 1a | 0.464 | NM_014520 | 1363 |
| CPA4 | Carboxypeptidase A4 | 0.462 | NM_016352 | 1364 |
| PTP4A1 | Protein tyrosine phosphatase type IVA, member 1 | 0.462 | NM_003463 | 1365 |
| RBMS1 | RNA binding motif, single stranded interacting protein 1 | 0.461 | NM_002897 | 1366 |
| FZD7 | Frizzled homolog 7 (Drosophila) | 0.461 | NM_003507 | 1367 |
| CLDN17 | Claudin 17 | 0.46 | NM_012131 | 1368 |
| FCER1A | Fc fragment of IgE, high affinity I, receptor for; alpha polypeptide | 0.46 | NM_002001 | 1369 |
| PDZK8 | PDZ domain containing 8 | 0.459 | NM_173791 | 1370 |
| SPTLC1 | Serine palmitoyltransferase, long chain base subunit 1 | 0.459 | NM_178324 | 1371 |

TABLE 1-continued

The EE transcriptome

| Common Name | Description | Fold Change | Genbank Accession number | SEQ ID NO |
|---|---|---|---|---|
| EPB41L4A | Erythrocyte membrane protein band 4.1 like 4A | 0.458 | NM_022140 | 1372 |
| FLJ39501 | Cytochrome P450, family 2, subfamily E, polypeptide 2 homolog | 0.458 | NM_173483 | 1373 |
| ZNF430 | Zinc finger protein 430 | 0.457 | NM_025189 | 1374 |
| SEQ_ID_#1375 | CDNA clone IMAGE: 4838152 | 0.457 | BC034596 | 1375 |
| AGR2 | Anterior gradient 2 homolog (*Xenopus laevis*) | 0.456 | NM_006408 | 1376 |
| RIOK3 | RIO kinase 3 (yeast) | 0.456 | NM_003831 | 1377 |
| SNX9 | Sorting nexin 9 | 0.456 | NM_016224 | 1378 |
| SEQ_ID_#1379 | Transcribed locus, strongly similar to NP_080835.1 thioredoxin-like 5 [*Mus musculus*] | 0.454 | AW510697 | 1379 |
| BCL10 | B-cell CLL/lymphoma 10 | 0.453 | NM_003921 | 1380 |
| AK3 | Adenylate kinase 3-like 1 | 0.453 | NM_013410 | 1381 |
| SEQ_ID_#1382 | | 0.452 | NM_014688 | 1382 |
| CMAS | Cytidine monophosphate N-acetylneuraminic acid synthetase | 0.452 | NM_018686 | 1383 |
| SEQ_ID_#1384 | Transcribed locus | 0.451 | AI632692 | 1384 |
| MYO6 | Myosin VI | 0.45 | NM_004999 | 1385 |
| FLJ31153 | Hypothetical protein FLJ31153 | 0.45 | NM_144600 | 1386 |
| PPP1R2 | Protein phosphatase 1, regulatory (inhibitor) subunit 2 | 0.449 | NM_006241 | 1387 |
| LPIN1 | Lipin 1 | 0.448 | NM_145693 | 1388 |
| XK | Kell blood group precursor (McLeod phenotype) | 0.448 | NM_021083 | 1389 |
| ACOT4 | Peroxisomal acyl-CoA thioesterase 2B | 0.448 | NM_152331 | 1390 |
| CHAC2 | Similar to RIKEN cDNA 2510006C20 gene | 0.447 | NM_001008708 | 1391 |
| ENC1 | Ectodermal-neural cortex (with BTB-like domain) | 0.447 | NM_003633 | 1392 |
| UBL3 | Ubiquitin-like 3 | 0.446 | NM_007106 | 1393 |
| ACPP | Acid phosphatase, prostate | 0.446 | NM_001099 | 1394 |
| SLC7A5 | Solute carrier family 7 (cationic amino acid transporter, y+ system), member 5 | 0.445 | NM_003486 | 1395 |
| C15orf29 | Chromosome 15 open reading frame 29 | 0.444 | NM_024713 | 1396 |
| WDR37 | WD repeat domain 37 | 0.443 | NM_014023 | 1397 |
| ZNF662 | Zinc finger protein 662 | 0.442 | NM_207404 | 1398 |
| LOC152831 | Klotho beta like | 0.442 | NM_175737 | 1399 |
| FN5 | B-cell CLL/lymphoma 7B | 0.441 | NM_020179 | 1400 |
| KIF21A | Kinesin family member 21A | 0.44 | NM_017641 | 1401 |
| SPIRE1 | Spire homolog 1 (*Drosophila*) | 0.44 | NM_020148 | 1402 |
| SLC7A11 | Solute carrier family 7, (cationic amino acid transporter, y+ system) member 11 | 0.439 | NM_014331 | 1403 |
| TEAD1 | TEA domain family member 1 (SV40 transcriptional enhancer factor) | 0.438 | NM_021961 | 1404 |
| SH3BGRL2 | SH3 domain binding glutamic acid-rich protein like 2 | 0.437 | NM_031469 | 1405 |
| PDZRN3 | PDZ domain containing RING finger 3 | 0.436 | NM_015009 | 1406 |
| PHGDH | Phosphoglycerate dehydrogenase | 0.435 | NM_006623 | 1407 |
| CAP2 | CAP, adenylate cyclase-associated protein, 2 (yeast) | 0.435 | NM_006366 | 1408 |
| PARP11 | Poly (ADP-ribose) polymerase family, member 11 | 0.435 | NM_020367 | 1409 |
| ALS2CR2 | Amyotrophic lateral sclerosis 2 (juvenile) chromosome region, candidate 2 | 0.433 | NM_018571 | 1410 |
| LOC168850 | Hypothetical protein LOC168850 | 0.433 | NM_176814 | 1411 |
| SMPDL3A | Sphingomyelin phosphodiesterase, acid-like 3A | 0.433 | NM_006714 | 1412 |
| C1orf9 | Chromosome 1 open reading frame 9 | 0.432 | NM_014283 | 1413 |
| HLA-DQB2 | Major histocompatibility complex, class II, DQ beta 2 | 0.432 | NM_182549 | 1414 |
| ZA20D2 | Zinc finger, A20 domain containing 2 | 0.431 | NM_006007 | 1415 |
| SNX16 | Sorting nexin 16 | 0.431 | NM_022133 | 1416 |
| ITCH | Itchy homolog E3 ubiquitin protein ligase (mouse) | 0.431 | NM_031483 | 1417 |
| MAMDC2 | MAM domain containing 2 | 0.431 | NM_153267 | 1418 |
| BEAN | Brain expressed, associated with Nedd4 | 0.43 | XM_375359 | 1419 |
| ABHD5 | Abhydrolase domain containing 5 | 0.43 | NM_016006 | 1420 |
| AGA | Aspartylglucosaminidase | 0.429 | NM_000027 | 1421 |
| SPAG1 | Sperm associated antigen 1 | 0.429 | NM_003114 | 1422 |
| BOC | Brother of CDO | 0.428 | NM_033254 | 1423 |
| MGST1 | Microsomal glutathione S-transferase 1 | 0.428 | NM_020300 | 1424 |
| C5orf13 | Chromosome 5 open reading frame 13 | 0.427 | NM_004772 | 1425 |
| PLEKHA5 | Pleckstrin homology domain containing, family A member 5 | 0.426 | NM_019012 | 1426 |

TABLE 1-continued

The EE transcriptome

| Common Name | Description | Fold Change | Genbank Accession number | SEQ ID NO |
|---|---|---|---|---|
| ZNF555 | Zinc finger protein 555 | 0.426 | NM_152791 | 1427 |
| TADA3L | Transcriptional adaptor 3 (NGG1 homolog, yeast)-like | 0.425 | NM_133480 | 1428 |
| PRKACB | Protein kinase, cAMP-dependent, catalytic, beta | 0.424 | NM_002731 | 1429 |
| HIST1H2BG | Histone 1, H2bg | 0.424 | NM_003518 | 1430 |
| PALMD | Palmdelphin | 0.423 | NM_017734 | 1431 |
| LOC136288 | Hypothetical protein LOC136288 | 0.421 | XM_059832 | 1432 |
| CALB2 | Calbindin 2, 29 kDa (calretinin) | 0.419 | NM_001740 | 1433 |
| PLA2G4A | Phospholipase A2, group IVA (cytosolic, calcium-dependent) | 0.417 | NM_024420 | 1434 |
| MT1H | Metallothionein 1H | 0.417 | NM_005951 | 1435 |
| SEQ_ID_#1436 | | 0.417 | AL031602 | 1436 |
| SEQ_ID_#1437 | Full-length cDNA clone CS0DD009YB17 of Neuroblastoma Cot 50-normalized of Homo sapiens (human) | 0.417 | AK000776 | 1437 |
| PFKFB3 | 6-phosphofructo-2-kinase/fructose-2,6-biphosphatase 3 | 0.415 | NM_004566 | 1438 |
| C10orf45 | Chromosome 10 open reading frame 45 | 0.415 | AK096685 | 1439 |
| BPGM | 2,3-bisphosphoglycerate mutase | 0.415 | NM_001724 | 1440 |
| EML1 | Echinoderm microtubule associated protein like 1 | 0.193 | NM_001008707 | 1441 |
| AKR1C1 | Aldo-keto reductase family 1, member C1 (dihydrodiol dehydrogenase 1; 20-alpha (3-alpha)-hydroxysteroid dehydrogenase) | 0.414 | NM_001353 | 1442 |
| TBC1D10 | TBC1 domain family, member 10A | 0.414 | NM_031937 | 1443 |
| MN1 | Meningioma (disrupted in balanced translocation) 1 | 0.414 | NM_002430 | 1444 |
| LOC120379 | Hypothetical protein BC019238 | 0.414 | NM_138789 | 1445 |
| IL18 | Interleukin 18 (interferon-gamma-inducing factor) | 0.414 | NM_001562 | 1446 |
| GSTA4 | Glutathione S-transferase A4 | 0.413 | NM_001512 | 1447 |
| LOC93622 | Hypothetical protein BC006130 | 0.412 | NM_138699 | 1448 |
| TNFRSF19 | Tumor necrosis factor receptor superfamily, member 19 | 0.412 | NM_148957 | 1449 |
| TMOD3 | Tropomodulin 3 (ubiquitous) | 0.41 | NM_014547 | 1450 |
| C10orf99 | Chromosome 10 open reading frame 99 | 0.406 | NM_207373 | 1451 |
| ACAA2 | Acetyl-Coenzyme A acyltransferase 2 (mitochondrial 3-oxoacyl-Coenzyme A thiolase) | 0.404 | NM_006111 | 1452 |
| SEQ_ID_#1453 | CDNA FLJ39842 fis, clone SPLEN2014293 | 0.404 | AK097161 | 1453 |
| CNN3 | Calponin 3, acidic | 0.404 | NM_001839 | 1454 |
| RPESP | RPE-spondin | 0.403 | NM_153225 | 1455 |
| SLC16A9 | Solute carrier family 16 (monocarboxylic acid transporters), member 9 | 0.402 | NM_194298 | 1456 |
| FLJ42117 | FLJ42117 protein | 0.398 | NM_198463 | 1457 |
| SYTL5 | Synaptotagmin-like 5 | 0.398 | NM_138780 | 1458 |
| WNK1 | WNK lysine deficient protein kinase 1 | 0.397 | NM_018979 | 1459 |
| TncRNA | Trophoblast-derived noncoding RNA | 0.395 | AF001893 | 1460 |
| UACA | Uveal autoantigen with coiled-coil domains and ankyrin repeats | 0.395 | NM_001008224 | 1461 |
| FRAS1 | Fraser syndrome 1 | 0.394 | NM_025074 | 1462 |
| KLHL24 | DRE1 protein | 0.393 | NM_017644 | 1463 |
| RFK | Riboflavin kinase | 0.392 | NM_018339 | 1464 |
| LOC92196 | Similar to death-associated protein | 0.392 | NM_001017920 | 1465 |
| MT1E | Metallothionein 1E (functional) | 0.392 | NM_175617 | 1466 |
| AKR1C3 | Aldo-keto reductase family 1, member C3 (3-alpha hydroxysteroid dehydrogenase, type II) | 0.392 | NM_003739 | 1467 |
| RAP2A | RAP2A, member of RAS oncogene family | 0.39 | NM_021033 | 1468 |
| ZNF76 | Zinc finger protein 76 (expressed in testis) | 0.389 | NM_003427 | 1469 |
| CHAC1 | Hypothetical protein MGC4504 | 0.389 | NM_024111 | 1470 |
| GATM | Glycine amidinotransferase (L-arginine: glycine amidinotransferase) | 0.386 | NM_001482 | 1471 |
| NHLH2 | Nescient helix loop helix 2 | 0.386 | NM_005599 | 1472 |
| H-plk | Zinc finger protein 117 (HPF9) | 0.386 | NM_015852 | 1473 |
| PANK1 | Pantothenate kinase 1 | 0.385 | NM_138316 | 1474 |
| RORA | RAR-related orphan receptor A | 0.384 | NM_002943 | 1475 |
| AFF4 | AF4/FMR2 family, member 4 | 0.383 | NM_014423 | 1476 |
| MGC39372 | Hypothetical protein MGC39372 | 0.383 | XM_376463 | 1477 |
| TP53INP2 | Tumor protein p53 inducible nuclear protein 2 | 0.383 | NM_021202 | 1478 |
| GGTA1 | Glycoprotein, alpha-galactosyltransferase 1 | 0.382 | AF378123 | 1479 |
| SEQ_ID_#1480 | Transcribed locus | 0.381 | BI757437 | 1480 |

TABLE 1-continued

The EE transcriptome

| Common Name | Description | Fold Change | Genbank Accession number | SEQ ID NO |
|---|---|---|---|---|
| DUSP5 | Dual specificity phosphatase 5 | 0.381 | NM_004419 | 1481 |
| NAP1L2 | Nucleosome assembly protein 1-like 2 | 0.381 | NM_021963 | 1482 |
| HBA2 | Hemoglobin, alpha 2 | 0.38 | NM_000517 | 1483 |
| SEQ_ID_#1484 | Homo sapiens, clone IMAGE: 5199401, mRNA | 0.38 | BC027846 | 1484 |
| PFN2 | Profilin 2 | 0.38 | NM_002628 | 1485 |
| GPX3 | Glutathione peroxidase 3 (plasma) | 0.377 | NM_002084 | 1486 |
| SEQ_ID_#1487 | CDNA FLJ14188 fis, clone NT2RP2005980 | 0.376 | AK024250 | 1487 |
| PKIB | Protein kinase (cAMP-dependent, catalytic) inhibitor beta | 0.373 | NM_032471 | 1488 |
| DHRS1 | Dehydrogenase/reductase (SDR family) member 1 | 0.372 | NM_138452 | 1489 |
| AMFR | Autocrine motility factor receptor | 0.371 | NM_001144 | 1490 |
| PDGFRA | Platelet-derived growth factor receptor, alpha polypeptide | 0.368 | NM_006206 | 1491 |
| TSPAN7 | Tetraspanin 7 | 0.367 | NM_004615 | 1492 |
| ARG2 | Arginase, type II | 0.367 | NM_001172 | 1493 |
| AMACR | Alpha-methylacyl-CoA racemase | 0.366 | NM_014324 | 1494 |
| ABLIM1 | Actin binding LIM protein 1 | 0.363 | NM_001003407 | 1495 |
| SEQ_ID_#1496 | Full length insert cDNA clone ZD63G05 | 0.361 | AF088051 | 1496 |
| CEACAM7 | Carcinoembryonic antigen-related cell adhesion molecule 7 | 0.361 | NM_006890 | 1497 |
| TP53I3 | Tumor protein p53 inducible protein 3 | 0.357 | NM_004881 | 1498 |
| OXR1 | Oxidation resistance 1 | 0.356 | NM_181354 | 1499 |
| NUCB2 | Nucleobindin 2 | 0.356 | NM_005013 | 1500 |
| SEQ_ID_#1501 | Transcribed locus | 0.356 | BF508966 | 1501 |
| ATP6V1C2 | ATPase, H+ transporting, lysosomal 42 kDa, V1 subunit C isoform 2 | 0.356 | NM_144583 | 1502 |
| C1orf71 | Chromosome 1 open reading frame 71 | 0.355 | NM_152609 | 1503 |
| SEQ_ID_#1504 | Transcribed locus | 0.354 | BI757437 | 1504 |
| GJA1 | Gap junction protein, alpha 1, 43 kDa (connexin 43) | 0.353 | NM_000165 | 1505 |
| IGSF11 | Immunoglobulin superfamily, member 11 | 0.353 | NM_001015887 | 1506 |
| PER1 | Period homolog 1 (*Drosophila*) | 0.352 | NM_002616 | 1507 |
| C1orf42 | Chromosome 1 open reading frame 42 | 0.351 | NM_019060 | 1508 |
| RGC32 | Response gene to complement 32 | 0.351 | NM_014059 | 1509 |
| A2ML1 | C3 and PZP-like, alpha-2-macroglobulin domain containing 9 | 0.35 | NM_144670 | 1510 |
| CAB39L | Calcium binding protein 39-like | 0.35 | NM_030925 | 1511 |
| ASAH3 | N-acylsphingosine amidohydrolase (alkaline ceramidase) 3 | 0.348 | NM_133492 | 1512 |
| SOSTDC1 | Sclerostin domain containing 1 | 0.346 | NM_015464 | 1513 |
| ABCG2 | ATP-binding cassette, sub-family G (WHITE), member 2 | 0.346 | NM_004827 | 1514 |
| AADACL2 | Arylacetamide deacetylase-like 2 | 0.346 | NM_207365 | 1515 |
| DPCR1 | Diffuse panbronchiolitis critical region 1 | 0.346 | NM_080870 | 1516 |
| C18orf25 | Chromosome 18 open reading frame 25 | 0.343 | NM_001008239 | 1517 |
| AKR1C2 | Aldo-keto reductase family 1, member C2 (dihydrodiol dehydrogenase 2; bile acid binding protein; 3-alpha hydroxysteroid dehydrogenase, type III) | 0.342 | NM_001354 | 1518 |
| TUBB2A | Tubulin, beta 2 | 0.341 | NM_001069 | 1519 |
| RASGEF1B | RasGEF domain family, member 1B | 0.341 | NM_152545 | 1520 |
| CST6 | Cystatin E/M | 0.334 | NM_001323 | 1521 |
| ARHGAP5 | synonyms: p190-B, RhoGAPS; isoform a is encoded by transcript variant 1; p105 RhoGAP; Rho GTPase-activating protein; p100 RasGAP-associated p105 protein; go_component: membrane [goid 0016020] [evidence IEA]; go_component: cytoplasm [goid 0005737] [evidence TAS] [pmid 8537347]; go_function: GTPase activity [goid 0003924] [evidence TAS] [pmid 8537347]; go_function: Rho GTPase activator activity [goid 0005100] [evidence TAS] [pmid 8537347]; go_process: cell adhesion [goid 0007155] [evidence TAS] [pmid 8537347]; go_process: Rho protein signal transduction [goid 0007266] [evidence TAS] [pmid 8537347]; *Homo sapiens* Rho GTPase activating protein 5 (ARHGAP5), transcript variant 1, mRNA. | 0.331 | NM_001030055 | 1522 |

TABLE 1-continued

The EE transcriptome

| Common Name | Description | Fold Change | Genbank Accession number | SEQ ID NO |
|---|---|---|---|---|
| C21orf81 | Chromosome 21 open reading frame 81 | 0.329 | NM_153750 | 1523 |
| CCDC6 | Coiled-coil domain containing 6 | 0.328 | NM_005436 | 1524 |
| ANKRD37 | Ankyrin repeat domain 37 | 0.326 | NM_181726 | 1525 |
| NQO1 | NAD(P)H dehydrogenase, quinone 1 | 0.324 | NM_000903 | 1526 |
| AKR1B10 | Aldo-keto reductase family 1, member B10 (aldose reductase) | 0.323 | NM_020299 | 1527 |
| ATP6V0A4 | ATPase, H+ transporting, lysosomal V0 subunit a isoform 4 | 0.322 | NM_020632 | 1528 |
| LOC339400 | Hypothetical protein LOC339400 | 0.321 | AK056431 | 1529 |
| GNA14 | Guanine nucleotide binding protein (G protein), alpha 14 | 0.32 | NM_004297 | 1530 |
| TFAP2B | Transcription factor AP-2 beta (activating enhancer binding protein 2 beta) | 0.319 | NM_003221 | 1531 |
| C9orf58 | Chromosome 9 open reading frame 58 | 0.318 | NM_001002260 | 1532 |
| RDH12 | Retinol dehydrogenase 12 (all-trans and 9-cis) | 0.316 | NM_152443 | 1533 |
| BLZF1 | Basic leucine zipper nuclear factor 1 (JEM-1) | 0.315 | NM_003666 | 1534 |
| GRPEL2 | GrpE-like 2, mitochondrial (*E. coli*) | 0.312 | NM_152407 | 1535 |
| LOC389432 | *Homo sapiens* SAM domain containing 1 (LOC389432), mRNA. | 0.31 | NM_001030060 | 1536 |
| YOD1 | YOD1 OTU deubiquinating enzyme 1 homolog (yeast) | 0.309 | NM_018566 | 1537 |
| ARG1 | Arginase, liver | 0.176 | NM_000045 | 1538 |
| KRT6B | Keratin 6B | 0.309 | NM_005555 | 1539 |
| SDR-O | Orphan short-chain dehydrogenase/reductase | 0.301 | NM_148897 | 1540 |
| BEXL1 | Brain expressed X-linked-like 1 | 0.301 | XM_043653 | 1541 |
| FAM43A | Family with sequence similarity 43, member A | 0.3 | NM_153690 | 1542 |
| IL1F5 | Interleukin 1 family, member 5 (delta) | 0.295 | NM_012275 | 1543 |
| CITED2 | Cbp/p300-interacting transactivator, with Glu/Asp-rich carboxy-terminal domain, 2 | 0.295 | NM_006079 | 1544 |
| FLJ10980 | Hypothetical protein FLJ10980 | 0.295 | BQ277484 | 1545 |
| RNASE7 | Ribonuclease, RNase A family, 7 | 0.292 | NM_032572 | 1546 |
| SEQ_ID_#1547 | Similar to ankyrin repeat domain 20A | 0.292 | BC016022 | 1547 |
| DEPDC6 | DEP domain containing 6 | 0.292 | NM_022783 | 1548 |
| PADI1 | Peptidyl arginine deiminase, type I | 0.287 | NM_013358 | 1549 |
| SEQ_ID_#1550 | Full length insert cDNA clone YI40A07 | 0.287 | AI819863 | 1550 |
| SPRR2D | Small proline-rich protein 2D | 0.286 | NM_006945 | 1551 |
| S100A12 | S100 calcium binding protein A12 (calgranulin C) | 0.286 | NM_005621 | 1552 |
| GHR | Growth hormone receptor | 0.286 | NM_000163 | 1553 |
| SEQ_ID_#1554 | *Homo sapiens* hypothetical LOC441178 (LOC441178), mRNA. | 0.286 | XM_379456 | 1554 |
| ZDHHC20 | Zinc finger, DHHC-type containing 20 | 0.283 | NM_153251 | 1555 |
| LOC115749 | Hypothetical protein LOC115749 | 0.281 | XM_056680 | 1556 |
| NGEF | Neuronal guanine nucleotide exchange factor | 0.279 | NM_019850 | 1557 |
| LOC56901 | NADH: ubiquinone oxidoreductase MLRQ subunit homolog | 0.278 | NM_020142 | 1558 |
| SORBS1 | | 0.277 | NM_001034954 | 1559 |
| HCG22 | HLA complex group 22 | 0.276 | XM_496804 | 1560 |
| FLJ40432 | Hypothetical protein FLJ40432 | 0.275 | NM_152523 | 1561 |
| SBSN | Suprabasin | 0.274 | NM_198538 | 1562 |
| TNFAIP3 | Tumor necrosis factor, alpha-induced protein 3 | 0.273 | BG218400 | 1563 |
| ZNF101 | Zinc finger protein 101 | 0.27 | NM_033204 | 1564 |
| ZBED2 | Zinc finger, BED-type containing 2 | 0.269 | NM_024508 | 1565 |
| DDAH1 | Dimethylarginine dimethylaminohydrolase 1 | 0.266 | NM_012137 | 1566 |
| SLC16A6 | Solute carrier family 16 (monocarboxylic acid transporters), member 6 | 0.263 | NM_004694 | 1567 |
| SH3GL3 | SH3-domain GRB2-like 3 | 0.262 | NM_003027 | 1568 |
| SEQ_ID_#1569 | *Homo sapiens* hypothetical LOC441178 (LOC441178), mRNA. | 0.259 | XM_379456 | 1569 |
| FNDC4 | Fibronectin type III domain containing 4 | 0.259 | NM_022823 | 1570 |
| PAQR8 | Progestin and adipoQ receptor family member VIII | 0.255 | NM_133367 | 1571 |
| SEQ_ID_#1572 | Similar to ankyrin repeat domain 20A | 0.248 | AK092114 | 1572 |
| IL8RB | Interleukin 8 receptor, beta | 0.244 | NM_001557 | 1573 |
| HIST1H2BC | Histone 1, H2bc | 0.243 | NM_003526 | 1574 |
| RGS17 | Regulator of G-protein signalling 17 | 0.243 | NM_012419 | 1575 |
| SLURP1 | Secreted LY6/PLAUR domain containing 1 | 0.24 | NM_020427 | 1576 |

TABLE 1-continued

The EE transcriptome

| Common Name | Description | Fold Change | Genbank Accession number | SEQ ID NO |
|---|---|---|---|---|
| BBOX1 | Butyrobetaine (gamma), 2-oxoglutarate dioxygenase (gamma-butyrobetaine hydroxylase) 1 | 0.238 | NM_003986 | 1577 |
| EDN3 | Endothelin 3 | 0.229 | NM_000114 | 1578 |
| MT1G | Metallothionein 1G | 0.228 | NM_005950 | 1579 |
| LOC283824 | Hypothetical protein LOC283824 | 0.227 | BX647541 | 1580 |
| PCSK5 | Proprotein convertase subtilisin/kexin type 5 | 0.225 | NM_006200 | 1581 |
| SIAT2 | ST6 beta-galactosamide alpha-2,6-sialyltranferase 2 | 0.224 | NM_032528 | 1582 |
| SYNPO2L | Synaptopodin 2-like | 0.222 | NM_024875 | 1583 |
| PNLIPRP3 | Pancreatic lipase-related protein 3 | 0.221 | NM_001011709 | 1584 |
| ME1 | Malic enzyme 1, NADP(+)-dependent, cytosolic | 0.221 | NM_002395 | 1585 |
| TCP11L2 | Hypothetical protein MGC40368 | 0.22 | NM_152772 | 1586 |
| ZNF426 | Zinc finger protein 426 | 0.215 | NM_024106 | 1587 |
| CGNL1 | Cingulin-like 1 | 0.214 | NM_032866 | 1588 |
| MGC11324 | Hypothetical protein MGC11324 | 0.21 | NM_032717 | 1589 |
| LOC401097 | Similar to LOC166075 | 0.207 | XM_376281 | 1590 |
| KRTAP3-2 | Keratin associated protein 3-2 | 0.204 | NM_031959 | 1591 |
| TGM3 | Transglutaminase 3 (E polypeptide, protein-glutamine-gamma-glutamyltransferase) | 0.203 | NM_003245 | 1592 |
| CRYM | Crystallin, mu | 0.199 | NM_001014444 | 1593 |
| CTNNAL1 | Catenin (cadherin-associated protein), alpha-like 1 | 0.19 | NM_003798 | 1594 |
| CRYAB | Crystallin, alpha B | 0.189 | NM_001885 | 1595 |
| UPK1A | Uroplakin 1A | 0.169 | NM_007000 | 1596 |
| ECG2 | Esophagus cancer-related gene-2 | 0.166 | NM_032566 | 1597 |
| FLJ21511 | Hypothetical protein FLJ21511 | 0.162 | NM_025087 | 1598 |
| C1orf177 | Chromosome 1 open reading frame 177 | 0.161 | NM_152607 | 1599 |
| SEQ_ID_#1600 | Homo sapiens cDNA clone IMAGE: 4826738. | 0.158 | BC042588 | 1600 |
| ALOX12 | Arachidonate 12-lipoxygenase | 0.157 | NM_000697 | 1601 |
| HIG2 | Hypoxia-inducible protein 2 | 0.156 | NM_013332 | 1602 |
| C1orf161 | Chromosome 1 open reading frame 161 | 0.154 | NM_152367 | 1603 |
| SEQ_ID_#1604 | | 0.152 | NM_006518 | 1604 |
| FLG | Filaggrin | 0.147 | NM_002016 | 1605 |
| SEQ_ID_#1606 | Transcribed locus, weakly similar to XP_220549.3 PREDICTED: similar to Zinc finger protein 287 (Zfp-287) (Zinc finger protein SKAT-2) [Rattus norvegicus] | 0.145 | BM994473 | 1606 |
| MT1M | Metallothionein 1K | 0.129 | NM_176870 | 1607 |
| P11 | 26 serine protease | 0.125 | NM_006025 | 1608 |
| NP | Nucleoside phosphorylase | 0.113 | NM_000270 | 1609 |
| CRISP2 | Cysteine-rich secretory protein 2 | 0.106 | NM_003296 | 1610 |
| ZNF365 | Hypothetical protein LOC283045 | 0.106 | NM_014951 | 1611 |
| CLDN10 | Claudin 10 | 0.0968 | NM_006984 | 1612 |
| CDA | Cytidine deaminase | 0.0876 | NM_001785 | 1613 |
| EPB41L3 | Erythrocyte membrane protein band 4.1-like 3 | 0.0832 | NM_012307 | 1614 |
| SFTPG | GSGL541 | 0.0709 | NM_205854 | 1615 |
| SNX19 | Sorting nexin 19 | 0.0664 | NM_014758 | 1616 |
| GYS2 | Glycogen synthase 2 (liver) | 0.0535 | NM_021957 | 1617 |
| DSG1 | Desmoglein 1 | 0.0405 | NM_001942 | 1618 |
| CRISP3 | Cysteine-rich secretory protein 3 | 0.039 | NM_006061 | 1619 |
| SEQ_ID_#1620 | CDNA FLJ43417 fis, clone OCBBF2026025 | 0.0268 | AK125406 | 1620 |

These 1620 genes comprised an EE transcript signature, also termed an EE transcriptome. The most induced transcript in EE was eotaxin-3; levels of eotaxin-3 strongly correlated with disease severity.

In one embodiment, the EE transcriptome was used to evaluate EE patients pre- and post-treatment regimens. For example, corticosteroids are frequently administered to patients with EE, and the specific glucocorticoid fluticasone propionate has been shown to induce EE disease remission (Gastroenterology 131 (2006) 1381) and to reverse EE gene dysregulation (J. Allergy Clin. Immunol., 120 (2007) 1292; U.S. Application Ser. No. 61/118,981, filed Dec. 1, 2008), each of which is incorporated by reference herein in its entirety.

As shown in FIG. 6, treatment of EE patients with fluticasone propionate normalized greater than 99% of the EE transcriptome (1605 genes/1620 genes), while leaving less than 1% of the EE transcriptome (13 genes/1620 genes) resistant to fluticasone propionate treatment. This group of 13 non-responsive genes is SEQ ID NOS. 6, 35, 43, 61, 129, 1358, 1441, 1515, 1538, 1584, 1615, 1618, and 1620. Evaluation of these genes provides a marker of past, present, and/or future active disease, especially in the absence of overt disease. These 13 genes were resistant to therapy, however, therapy resulted in normal clinical and/or physical characteristics. Thus, these 13 genes can be used to evaluate a patients propensity to EE, particularly in the absence of clinical or physical symptoms of EE or microscopic findings typical of EE. Because the profiles of these genes, i.e., whether they were over-expressed or under-expressed, did not change when the patient was on therapy, these 13 genes can be used to evaluate whether a patient had EE in the past or currently has inactive EE. These 13 genes can be used to evaluate EE in an asymptomatic population or when past EE is suspected in a non-active EE individual at the time of endoscopy. In one embodiment, the expression level of at least one of these 13 genes is compared to control levels and under- or over-expression of one or more of these 13 genes by ≥1.5 fold, indicating that the patient is either a past EE patient and/or is susceptible to future EE disease development.

The method may evaluate treatment efficacy with different drugs within a particular group (e.g., different corticosteroids), among the same group (e.g., corticosteroids compared to non-corticosteroids), or among different groups (e.g., steroids compared to non-steroid drugs). The method may evaluate treatment efficacy at different doses, provided in different therapeutic regimens (e.g., frequency, duration, etc.).

Normalization of expression levels of 99% of the genes in the EE transcriptome by fluticasone propionate treatment permitted determination of potential pathways by which fluticasone propionate and other treatments, e.g., other glucocorticoids, treat EE. In one embodiment, the EE transcriptome was used to examine the cellular and molecular pathways of EE, and the way by which a particular therapy treated EE, provided information about the basis, attributes, and potential modifiers of EE. For example, a role of interleukin 13 (IL-13) and its signaling pathways has been implicated in the pathophysiology of EE, as described in U.S. Application Ser. No. 61/118,981, filed Dec. 1, 2008, which is incorporated by reference herein in its entirety.

The 1620 genes in the EE transcriptome are highly conserved. Their complex expression pattern delineates molecular features, cell composition, and cell activation in EE.

In one embodiment, the EE transcriptome was compared to transcriptomes in cell/tissues that had been treated with one or more compounds potentially involved with and/or efficacious against EE. By comparing the EE transcriptome to the transcriptome of, e.g., a simple in vitro or ex vivo model of a particular compound, one can assess the percentage of genes that are dysregulated in EE due to that particular compound.

For example, in ex vivo or in vitro models, a compound was used to stimulate an esophageal cell type. The genes that were dysregulated in this model, and hence exhibit an altered transcriptome, allowed one to determine the percentage of genes that were dysregulated in EE due to treatment with this compound. A transcriptome generated in esophageal epithelial cells that had been stimulated with IL-13 revealed that 20% of the genes of the EE transcriptome were potentially due to IL-13 stimulation of esophageal epithelial cells. These data permitted determination of the involvement of a compound in EE, e.g. that IL-13 was a key component in EE. These data permitted assessment of the percentage of gene(s) a compound would potentially block, e.g. that an inhibitor of the compound IL-13 would potentially reverse the expression of this same 20% of the EE transcriptome and predict the potential positive effect of the compound. These data permitted generation of a list of genes that would be expected to be down-regulated by a compound, and that thus could be used to assess the compound's efficacy on therapy and/or treatment compliance.

In one embodiment, evaluation of the EE transcriptome was used to determine efficacy of non-drug therapies. For example, having patients with EE follow a controlled diet, where some foodstuffs are limited or eliminated, normalized expression levels of many genes in the EE transcriptome, as shown in FIG. 6. Elimination diets that completely eliminate certain foodstuffs (e.g., wheat, soy, milk, peanuts, and/or seafood) and elemental diets that completely lack certain elements (e.g., liquid diets that contain only amino acids but no proteins to act as allergens) have been used with some success to treat children with EE. In one embodiment, the EE transcriptome is used to assess potential non-drug EE treatments by comparing the gene expression profile pre- and post-such treatment. For example, a child with EE may be put on an elimination diet for a defined period, and the gene expression profile compared before, during, and at the termination of the defined period to assess effect of the foodstuff that was eliminated from the child's diet during the period.

Some individuals with EE do not respond to treatment (FIG. 5). Even after they have received treatment (e.g., a particular drug, elimination diet, elemental diet, etc.), such non-responder individuals have an EE transcriptome that resembles untreated EE patients, i.e., genes that are up-regulated in EE and genes that are down-regulation in EE remain up-regulated and down-regulated, respectively, despite the individual having received a particular treatment for EE.

Analysis of the gene expression profile pre- and post-treatment allows a medical practitioner to determine whether a particular treatment method demonstrates efficacy, or whether an alternative form of treatment, or a different treatment regime (e.g., increased dosing) is warranted. In one embodiment, analysis of the EE transcriptome is used to assess whether a patient is responding to a particular treatment.

In one embodiment, analysis of the EE transcriptome is used to assess and/or monitor patient compliance. For example, a patient with EE may not respond to therapy because the patient is a non-responder, or may not respond to therapy because the patient is not complying with the complete dosage regimen and thus may have a subthreshold drug concentration.

In one embodiment, evaluation of the EE transcriptome was used to assess EE in the presence of another pathology that may confound the diagnosis of EE. While EE is commonly diagnosed using histological methods to assess the level of eosinophil infiltration into, and/or thickening of, esophageal tissue, the presence and extent of eosinophil infiltration can be affected by various factors. The esophagus is normally devoid of eosinophils. However eosinophils can infiltrate the esophagus in pathological condition such as parasitic infection, fungal infections, hypereosinophilic syndromes, inflammatory bowel disease, certain cancers, recurrent vomiting, gastroesophageal reflux disease (GERD), etc., in addition to EE, so eosinophil presence/concentration in the esophagus cannot definitively diagnose between, e.g., EE and GERD. These diseases need to be ruled out before EE can be diagnosed. Evaluation of the EE transcriptome to identify the genes specifically involved in EE, e.g., eotaxin-3, allows one to discriminate between these pathologies and rule in or rule out EE with enhanced definiteness.

The diagnosis of EE is often suspected whenever dysphagia for solid food occurs, although it is not one of the more common causes of dysphagia. Dysphagia is frequently evaluated with endoscopy (esophagogastroduodenoscopy, or EGD) to determine its cause. During EGD, a flexible viewing tube or endoscope is inserted through the mouth and into the esophagus, permitting the medical practitioner to see the inner esophageal mucosa and lumen. Certain abnormalities, such as narrowing of most of the esophagus, or a series of rings along the entire length of the esophagus, suggest EE. However, in many patients with EE, upon such visualization the esophagus appears normal or shows only minor abnormalities. Thus, an accurate diagnosis of EE using visual and/or histological methods depends on the presence of characteristics that may or may not be present. The accurate diagnosis of EE using histological evaluation of a tissue biopsy specimen depends on when the biopsy is obtained. For example, histological evaluation may differ in early-stage EE biopsy tissue compared to later-stage biopsy EE tissue. The accurate diagnosis of EE may be compromised if other pathologies are present.

Evaluation of the EE transcriptome permitted a more accurate assessment, diagnosis, determination of course, etc., of EE. Evaluation of the EE transcriptome may be performed independent of, or concomitant with, other assessment methods such as, e.g., histological evaluation of a tissue biopsy specimen. Evaluation of the EE transcriptome may be performed, e.g., when eosinophil infiltration has not reached pre-determined numbers, in disease remission, in the absence of physical characteristics, or in the presence of one or more confounding pathologies.

In one embodiment, evaluation of the EE transcriptome is used to diagnose past, present, and/or future EE disease. When a patient with EE patient is treated successfully and, upon histological evaluation of a tissue biopsy specimen, presents no pathology, the pathologist, based upon the microscopic appearance, typically reports the patient as normal with no diagnosis abnormality. However, evaluation of the EE transcriptome reveals dysregulation of the 13 non-responsive genes despite the normal histological appearance of biopsy tissues. Thus, while eosinophil tissue infiltration is a marker of active EE, evaluation of the EE transcriptome provides information of EE history, e.g., it can assess presence and/or severity of prior pathology. Such assessment is useful because the dynamic and seasonal nature of EE is known.

In one embodiment, evaluation of the EE transcriptome is used to diagnose EE in the absence of overt disease, i.e., EE variability and/or inherency. In one embodiment, the expression level of the 13 non-responsive genes is used to diagnose EE in the absence of overt or active disease. In one embodiment, the 13 non-responsive genes allow diagnosis of chronic and relapsing forms of EE, and may provide an understanding of the pathophysiology of these forms. For example, evaluation of the EE transcriptome can identify sporadic, e.g. recurring or relapsing, forms of EE. As described above, histological assessment of a tissue biopsy specimen and extent of tissue eosinophil infiltration depends on when, during the course of EE, the assessment is performed. In contrast, a sporadic form of EE that is missed by these methods would, in fact, be captured by evaluating the EE transcriptome because the under-expression or over-expression exhibited by these genes is independent of active EE.

In one embodiment, evaluation of the EE transcriptome is used to assess familial components or contributions to EE by providing a transcriptome basis of comparison among genetic family members of the EE patient. There is evidence indicating a strong familial association or aggregation for EE. Approximately 10% of parents of EE patients have a history of esophageal strictures, and approximately 8% of these have EE as established by histological evaluation of a tissue biopsy specimen.

Among the approximately 300 first pediatric probands, e.g. individuals exhibiting EE, recruited into our research databank, 26 of them have at least one sibling or parent with EE (data not provided). Three adult brothers with dysphagia were reported to have EE (Patel and Falchuk). One widely used measure of familial aggregation is the sibling recurrence risk ratio, termed $\lambda S$, that compares the risk of sibling disease recurrence versus the risk, or disease prevalence, in the general population. A value for $\lambda S>1$ indicates an increased risk of EE development among siblings of the proband, compared to the general population. The prevalence of EE in the general population is approximately 5/10,000. Based on this prevalence, the estimated sibling recurrence risk ratio, $\lambda S$, for EE is approximately 80. Compared with common allergic disorders, such as atopy or asthma where $\lambda S$ is estimated at approximately 2, the considerably high sibling recurrence risk ratio in EE indicated that genetics was likely to have a relatively large role.

In one embodiment, evaluation of the EE transcriptome is used to identify candidate genes responsible for a familiar association. The gene for eotaxin-3 gene was one candidate gene. A single nucleotide polymorphism (SNP), +2496 T>G, rs2302009) in the gene for eotaxin-3 showed association with EE by both population-based case-control comparison and family-based transmission disequilibrium testing. Thus, the evaluation of the EE transcriptome among genetic family members, some of who exhibited symptoms of EE, may provide early EE diagnosis in other family members who did not exhibit symptoms. Such information facilitates determination of hereditary factors for EE.

In one embodiment, a diagnostic assay for eosinophilic esophagitis includes an ELISA (enzyme linked immunosorbent assay) or other clinically applicable immunoassay. In another embodiment, a diagnostic assay for eosinophilic esophagitis includes a test strip containing an anti-eotaxin-3 binding substance such as an antibody to which eotaxin-3 or eotaxin-3 like protein or peptide in a patient's biological sample (e.g. blood, sputum, feces, tissue fluid, cerebrospinal fluid, etc.) would bind. The test strip may include a chromogenic, fluorogenic, or luminescent substrate, detection reagents, etc., as known to one skilled in the art. The anti-eotaxin-3 antibody may be a rodent or other animal antieotaxin-3 antibody. The assay would include at least one suitable reagent, such as an enzyme (e.g. an oxidoreductase, transferase, hydrolase, lyase, isomerase, or ligase), in one embodiment horseradish peroxidase, o-toluidine, or colloidal gold, whereby the reagent reacts with an antigen/antibody complex on the test strip. A chromogen or other detectable indicator of binding or lack of binding, depending upon the assay format (e.g. competitive, non-competitive, sandwich, etc.) indicates binding of the anti-eotaxin-3 antibody to eotaxin-3 present in a supranormal level for a qualitative test, and may indicate the degree of binding for a quantitative or semi-quantitative test. Binding typically is indicated or visually detected via the presence or absence of color, fluorescence, luminescence, etc. Such test kit components and configurations are well known to one skilled in the art and are within the scope of the invention.

An example of certain suitable substrates and a suitable reagent may include, respectively, dimethyl or diethyl analogues of p-phenylenediamine with 4-chloro-1-naphthol or 3-methyl-2-benzothiazoline hydrazone with 4-chloro-1-naphthol and horseradish peroxidase. Other exemplary substrates used with horseradish peroxidase include 3,3',5,5'-tetramethylbenzidine, 2,2'-azinobis[3-ethylbenzothiazoline-6-sulfonic acid]-diammonium salt, o-phenylenediamine dihydrochloride, and QuantaBlu.

The anti-eotaxin-3 antibody may be a monoclonal or polyclonal antibody. Methods of producing monoclonal and polyclonal antibodies are known to one skilled in the art. Anti-eotaxin-3 antibodies may be generated as disclosed in U.S. Pat. No. 6,780,973, previously expressly incorporated by reference herein in its entirety. Also, a commercially available anti-eotaxin-3 antibody may be used.

As indicated above, eotaxin-3 selectively signals through the CCR3 receptor expressed on activated eosinophils or on other cells such as mast cells. As such, eosinophilic esophagitis may be mitigated by altering an eotaxin-3 binding and/or signaling mechanism, and/or CCR3 structure, function, and/or internalization. One such example is a method to provide an inhibitor to eotaxin-3 and/or CCR3 in an eosinophil or a mast cell under conditions sufficient to inhibit eotaxin-3 binding to the receptor. For example, the inhibitor may be provided to the esophageal tissue or to the blood stream in an amount sufficient to inhibit eotaxin-3 binding to the eotaxin-3 receptor. The inhibitor may be a small molecule inhibitor and/or a CCR3 antagonist. Exemplary CCR3 antagonists may include a humanized or human antieotaxin-3 antibody, MIG, I-TAO, IP-10 (U.S. patent application Ser. No. 10/752,659, titled "Cytokine Inhibition of Eosinophils," filed on Jan. 1, 2004; Zimmermann et al., *J. Allergy Clin. ImmunoL*, (2003) 3, 227), vMIP-II (Kleidel et al., *Science*, (1997) 277, 1656), met-RANTES (Elsner et al., *Eur. J. Immunol.*, (1997) 27, 2892), carboxamide derivatives (Naya et al., *Bioorg. Med. Chem. Lett.*, (2001) 11, 1219), 2-(Benzothiazolylthio)acetamide derivatives (Naya et al., *Chem. Pharm. Bull.*, (2003) 51, 697; Saeki et al., *Biochem. Biophys. Res. Comm.*, (2001) 281, 779), piperidine derivatives including indolinopiperidines or benzylpiperidines (Wacker et al., *Bioorg. Med. Chem. Leit.*, (2002)12, 1785; Varnes et al., *Bioorg. Med. Chem. Lett.*, (2004) 14, 1645), or such other nonpeptides as UCB35625 and derivatives thereof (Sabroe et al., *J. Biol. Chem.*, (2000) 275, 25985), and SK&F-$_L$-45523 and derivatives thereof (White et al., J. Biol. Chem, (2000) 275, 36626). Certain of the above antagonists, e.g., UCB35625, may also be considered small molecule inhibitors (Sabroe et al., J. Biol. Chem., (2000) 275, 25985). Each of the references cited is expressly incorporated by reference herein in its entirety.

The inhibitor need not completely inhibit binding, signal transduction, and/or function or cause receptor internalization. As used herein, an inhibitor may cause any reduction in one or more of these properties compared to a normal level. An eotaxin-3 and/or CCR3 inhibitor may also specifically inhibit transcription and/or translation of eotaxin-3, and/or CCR3 such as by utilizing antisense oligonucleotides and transcription factor inhibitors. An inhibitor may include a glucocorticoid that can work by inhibiting eotaxin-3 promoter-driven reporter gene activity and accelerating the decay of eotaxin-3 mRNA (Zimmermann et al., J. *Allergy Clin. Immunol.*, (2003) 3, 227). An inhibitor may also induce CCR3 internalization (Zimmermann et al., *J. Biol. Chem.*, (1999) 274, 12611). Each of the references cited is expressly incorporated by reference herein in its entirety.

An inhibitor may be administered directly or with a pharmaceutically acceptable diluent, carrier, or excipient, in unit dosage form. Conventional pharmaceutical practice may be employed to provide suitable formulations or compositions to administer the inhibitor to patients with, or presymptomatic for, eosinophilic esophagitis. Any appropriate route of administration may be employed, for example, parenteral, intravenous, subcutaneous, intramuscular, intracranial, intraorbital, ophthalmic, intraventricular, intracapsular, intraspinal, intracistemal, intraperitoneal, intranasal, aerosol, or oral administration. Therapeutic formulations may be in the form of solids, liquid solutions, or suspensions; for oral administration, formulations may be in the form of tablets (chewable, dissolvable, etc.), capsules (hard or soft gel), pills, syrups, elixirs, emulsions, etc.; and for intranasal formulations, in the form of powders, nasal drops, or aerosols. In one embodiment, a CCR3 antagonist is administered parenterally and/or orally. Enteral formulations may contain thixotropic agents, flavoring agents, and other ingredients for enhancing organoleptic qualities.

Methods known in the art for making formulations are found in, for example, "Remington's Pharmaceutical Sciences." Formulations for parenteral administration may, for example, contain excipients, including but not limited to pharmaceutically acceptable buffers, emulsifiers, surfactants, and electrolytes such as sodium chloride, as well as sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Formulations for inhalation may also contain excipients, for example, lactose, or may be aqueous solutions containing, for example, polyoxyethylene-9-lauryl ether, glycocholate and deoxycholate, or may be oily solutions for administration in the form of nasal drops, or as a gel.

Applicants incorporate by reference the material contained in the accompanying computer readable Sequence Listing identified as SEQUENCE_LISTING_ST25.txt, having a file creation date of Jun. 24, 2009 3:30 P.M. and a file size of 6.98 MB.

Other variations or embodiments of the invention will also be apparent to one of ordinary skill in the art from the above figures and descriptions. Thus, the forgoing embodiments are not to be construed as limiting the scope of this invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10155985B2). An electronic copy of the "Sequence Listing" will also be available from the USPTO upon request and payment of the fee set forth in 37 CFR 1.19(b)(3).

What is claimed is:

1. A method of diagnosing and treating eosinophilic esophagitis (EE) in a human patient, the method comprising:
obtaining a sample of esophageal tissue from the patient;
isolating RNA from the sample;
performing a laboratory analysis of the RNA to determine the expression of eotaxin 3 (SEQ ID NO:1) and at least one gene of a set of genes identified by the following sequence identifiers, SEQ ID NOs: 8, 9, 14, 39, 44, 45, 61, 79, 104, 952, 1535, 1538, 1544, 1584, 1593, 1594, 1596, 1607, 1610, 1612, and 1618;
determining whether the expression of the eotaxin 3 (SEQ ID NO:1) and the at least one gene of the set of genes is
over-expressed by at least 1.5 fold compared to its expression in normal esophageal tissue for the eotaxin 3 (SEQ ID NO:1) and SEQ ID NOs: 8, 9, 14, 39, 44, 45, 61, 79, 104; or
under-expressed by at least 1.5 fold compared to its expression in normal esophageal tissue for SEQ ID NOs: 104, 952, 1535, 1538, 1544, 1584, 1593, 1594, 1596, 1607, 1610, 1612, and 1618;
diagnosing the patient as having EE when the over- or under-expression of the eotaxin 3 (SEQ ID NO:1) and the at least one gene of the set of genes exceeds 1.5-fold; and
administering an EE therapy to the patient diagnosed as having EE.

2. The method of claim 1, wherein the patient lacks at least one of the clinical, pathological, or physical symptoms of EE.

3. The method of claim 1, wherein the EE therapy is a corticosteroid.

4. The method of claim 3, wherein the corticosteroid is fluticasone propionate.

5. The method of claim 1, wherein the set of genes further comprises one or more additional genes selected from the group of the genes identified by the following sequence identifiers, SEQ ID NOs: 2-7, 11, 13, 18, 23, 25-33, 36, 38, 40-42, 45, 46, 49, 50, 53, 81, 159, 544, 1394, 1441, 1567, 1597, 1601, 1602, 1605, 1608, 1611, 1613, 1617, and 1619; and
determining whether the expression of each of the one or more additional genes is
over-expressed by at least 1.5 fold compared to its expression in normal esophageal tissue for SEQ ID NOs: 1-7, 11, 13, 18, 23, 25-33, 36, 38, 40-42, 45, 46, 49, 50, 53, 81, 159, 544; or
under-expressed by at least 1.5 fold compared to its expression in normal esophageal tissue for SEQ ID NOs: 1394, 1441, 1567, 1597, 1601, 1602, 1605, 1608, 1611, 1613, 1617, and 1619.

* * * * *